(12) United States Patent
Hammond et al.

(10) Patent No.: US 8,637,653 B2
(45) Date of Patent: Jan. 28, 2014

(54) INFECTIOUS PLANT VIRAL VECTOR AND AN ARTIFICIAL BIPARTITE PLANT VIRAL VECTOR AN INFECTIOUS PLANT VIRAL VECTOR AND AN ARTIFICIAL BIPARTITE PLANT VIRAL VECTOR

(75) Inventors: John Hammond, Laurel, MD (US); Hyoun Sub Lim, Ellicott City, MD (US); Leslie L. Domier, Urbana, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 231 days.

(21) Appl. No.: 12/645,027

(22) Filed: Dec. 22, 2009

(65) Prior Publication Data
US 2011/0154538 A1 Jun. 23, 2011

(51) Int. Cl.
| | |
|---|---|
| C12N 7/01 | (2006.01) |
| C12N 15/33 | (2006.01) |
| C12N 15/82 | (2006.01) |
| C12N 15/87 | (2006.01) |
| C12N 5/10 | (2006.01) |
| C12N 15/113 | (2010.01) |
| A01H 5/00 | (2006.01) |

(52) U.S. Cl.
USPC ............ 536/23.72; 435/320.1; 435/419; 536/24.5; 800/280; 800/285; 800/288

(58) Field of Classification Search
USPC .......................................... 800/278
See application file for complete search history.

(56) References Cited

U.S. PATENT DOCUMENTS

| | | | | |
|---|---|---|---|---|
| 6,232,099 | B1 * | 5/2001 | Chapman et al. | 435/69.3 |
| 6,759,571 | B1 * | 7/2004 | Robertson | 800/285 |
| 2010/0071084 | A1 * | 3/2010 | Marillonnet et al. | 800/278 |

OTHER PUBLICATIONS

Guo et al. Protein tolerance to random amino acid change (2004) Proc. Nat. Acad. Sci. 101: 9205-9210.*
Farah et al. Cauliflower mosaic virus P35S promoter activity in *Escherichia coli* (1990) Mol. Gen. Genet. 223: 517-520.*
Gleba et al. Engineering viral expression vectors for paints: the 'full virus' and 'deconstructed virus' strategies (2004) Curr. Opin. Plant Biol. 7: 182-188.*
Kavanaugh et al. (GenBank accession No. M95516.1).*

* cited by examiner

*Primary Examiner* — Russell Kallis
*Assistant Examiner* — Steven Bernacki
(74) *Attorney, Agent, or Firm* — John D. Fado; Evelyn M. Rabin; Gail E. Poulos

(57) ABSTRACT

We have developed a versatile plant viral vector system based on Alternanthera mosaic virus (AltMV), suitable for infection by agroinfiltration or in vivo T7 transcripts from the same clone; agroinfection is enhanced by coinfiltration of a T7 RNA polymerase construct. Variants adapted for efficient protein expression, or for virus-induced gene silencing (VIGS), are based on a specific amino acid substitution (L88P) in the triple gene block 1 (TGB1) protein affecting RNA silencing suppression. A bipartite delivery system developed for AltMV delivers replicase (RdRp) functions separately from movement and encapsidation (TGB and coat protein, CP) functions by agroinfiltration, resulting in precise recombination of RdRp and TGB-CP constructs in planta. The bipartite delivery system has potential for high throughput protein expression or VIGS with the appropriate TGB1 variant, for hosts including *Nicotiana benthamiana* and *Arabidopsis thaliana*. Equivalent TGB1 substitutions in other potexviruses also reduced RNA silencing suppression, demonstrated with Potato virus X.

16 Claims, 29 Drawing Sheets
(20 of 29 Drawing Sheet(s) Filed in Color)

Fig. 1A-B

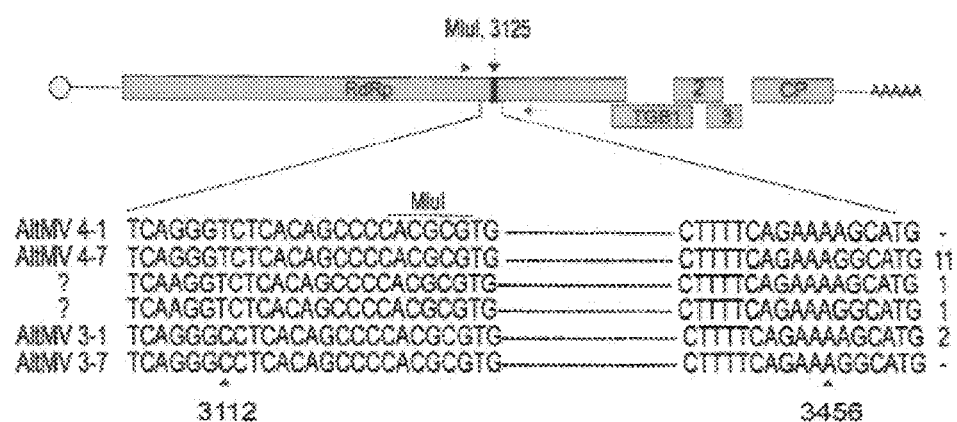
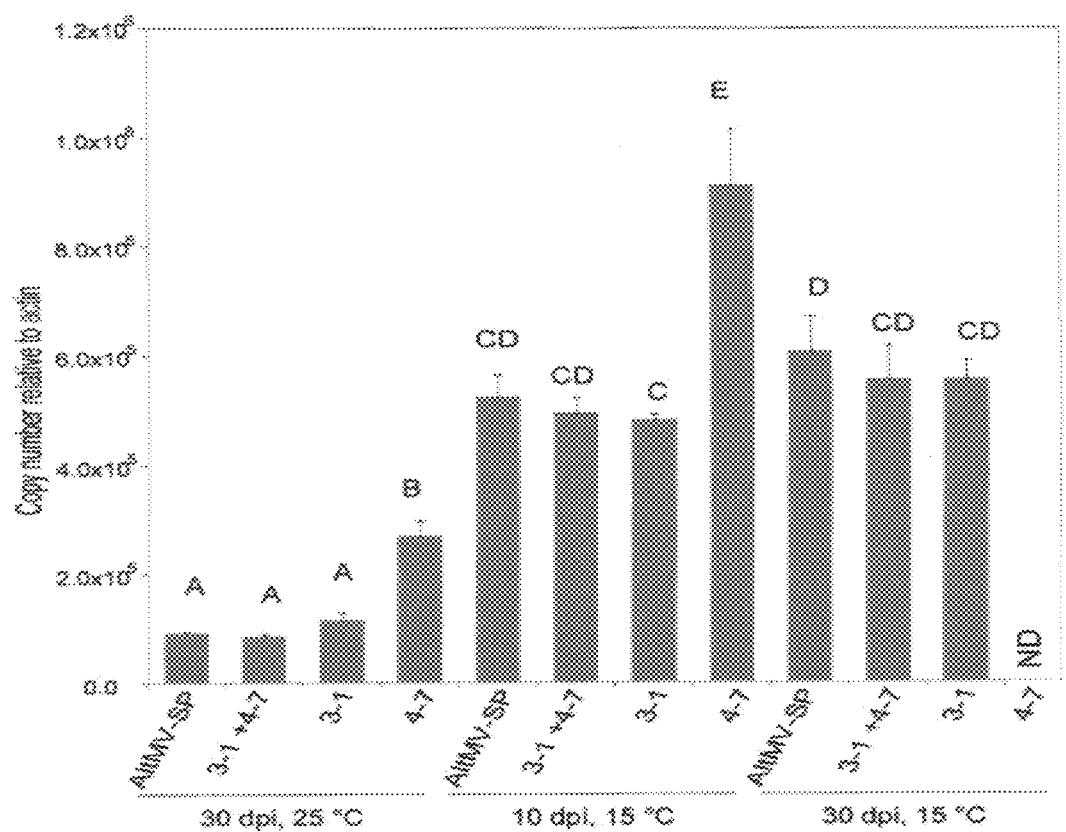
Fig. 3A-B

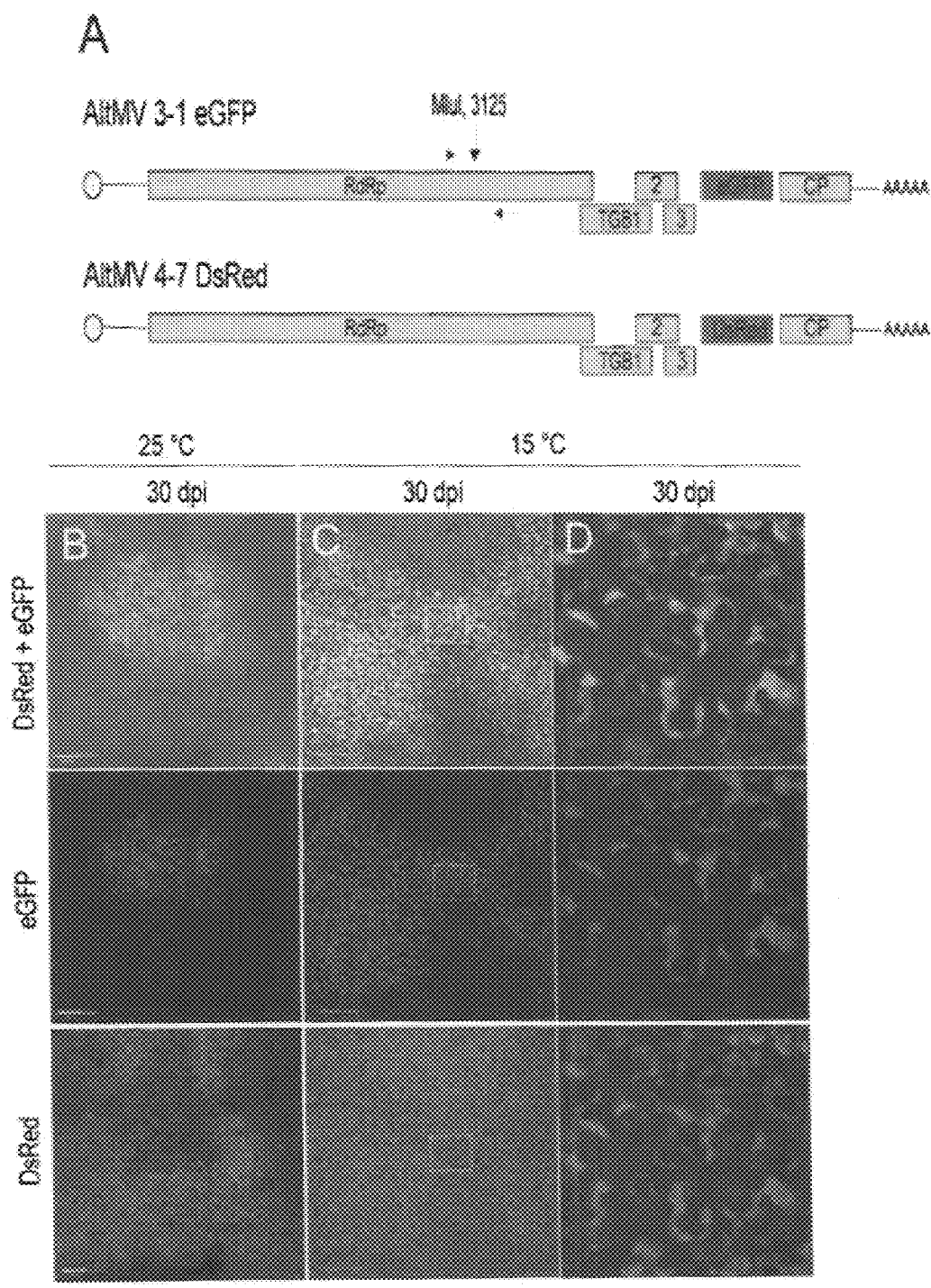
Fig. 4A-D

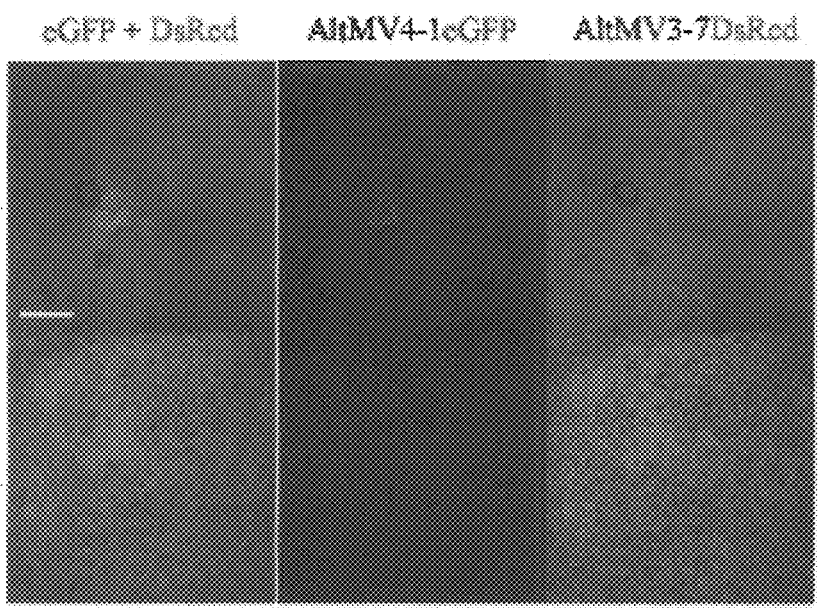
Fig. 4E-F

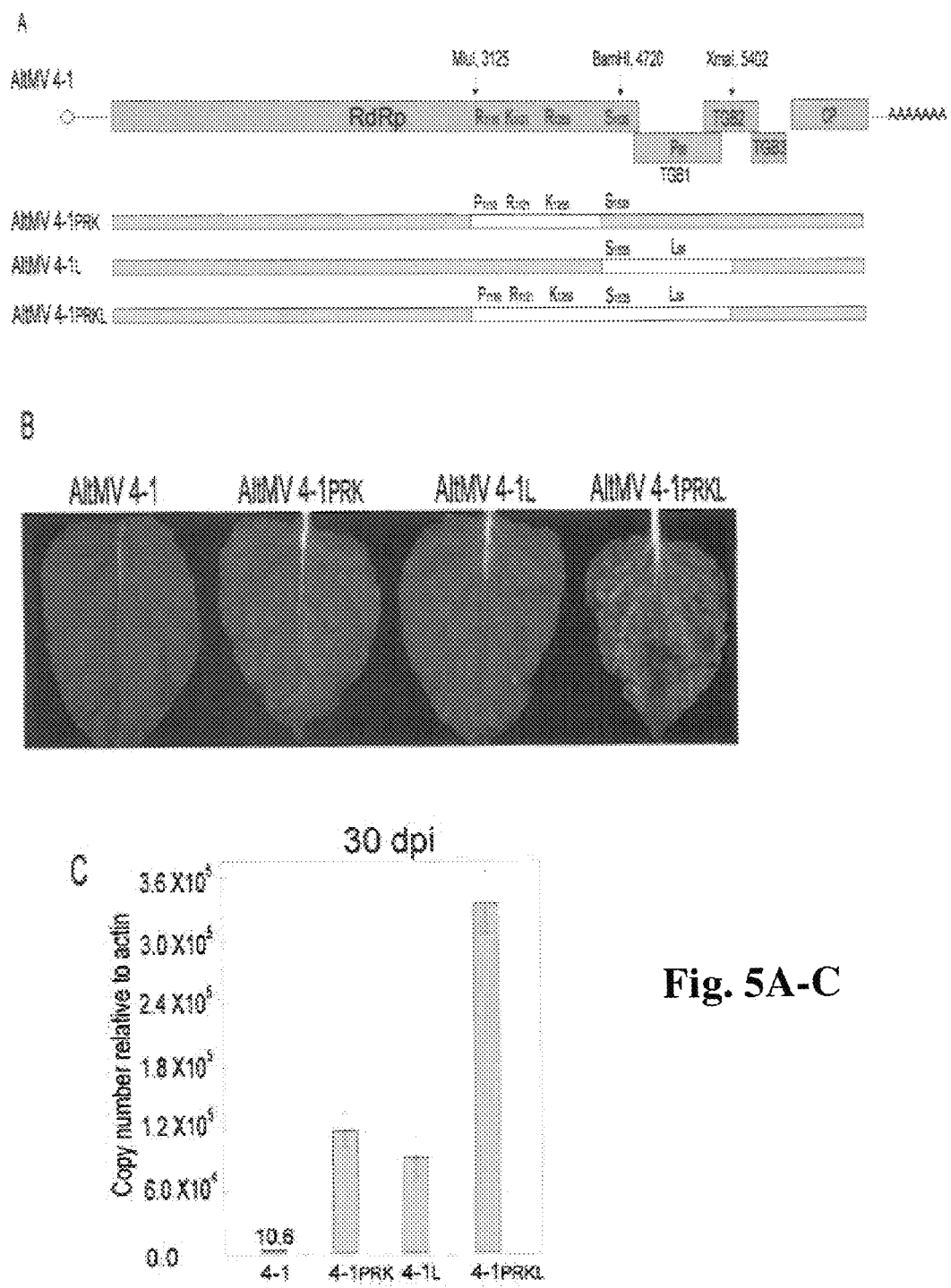
Fig. 5A-C

Fig. 6A-B

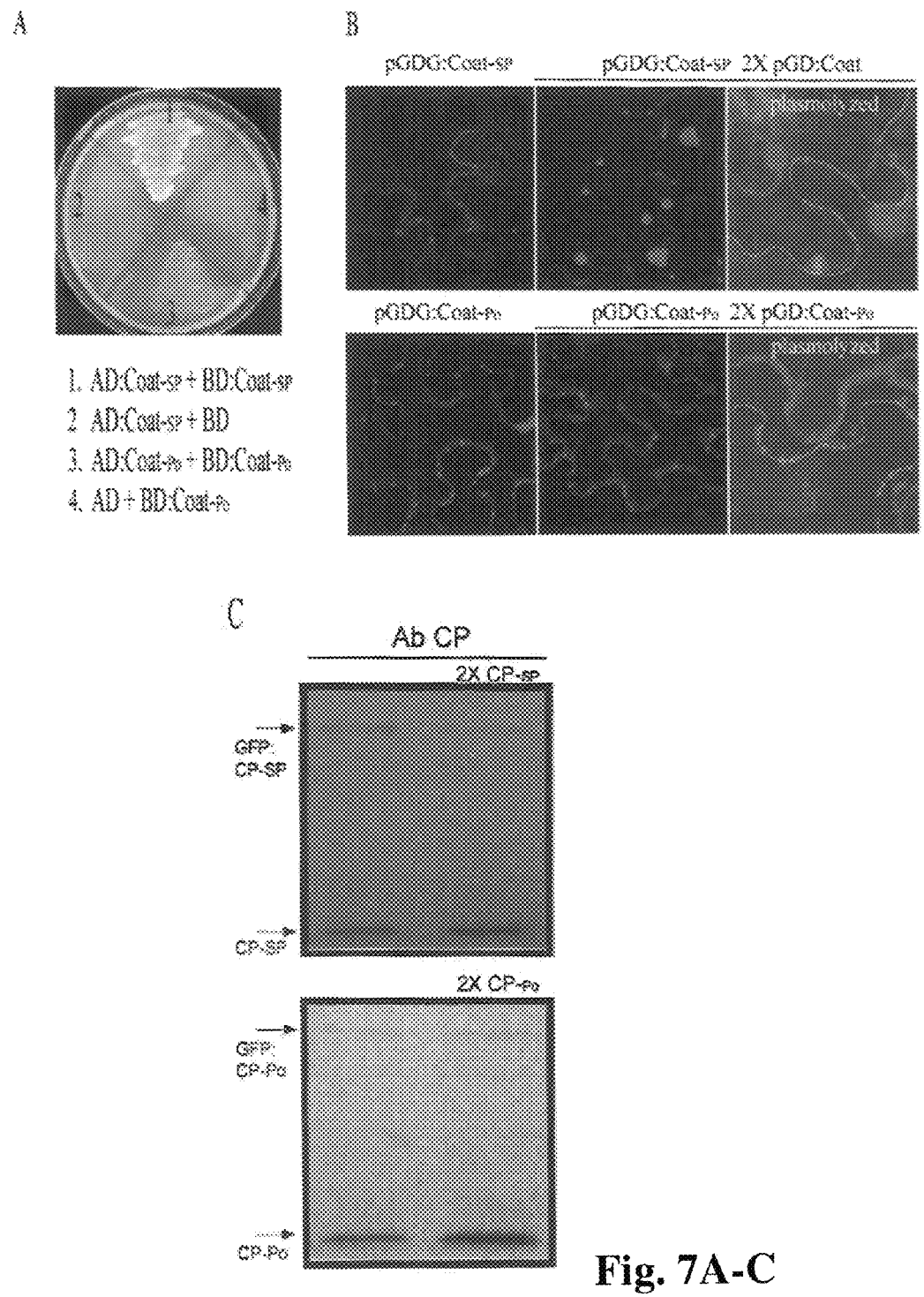
Fig. 7A-C

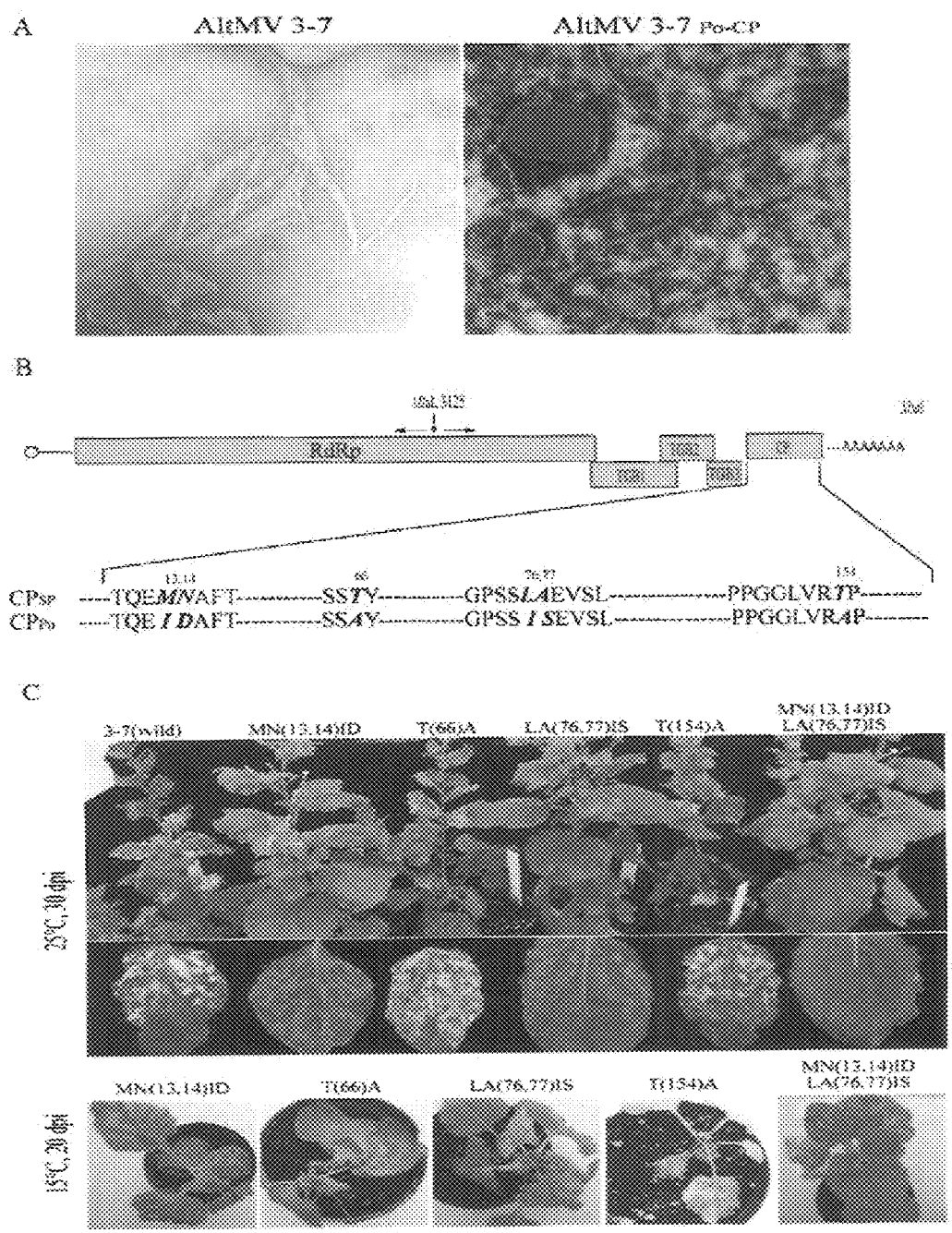
Fig. 8A-C

Fig. 9A-C

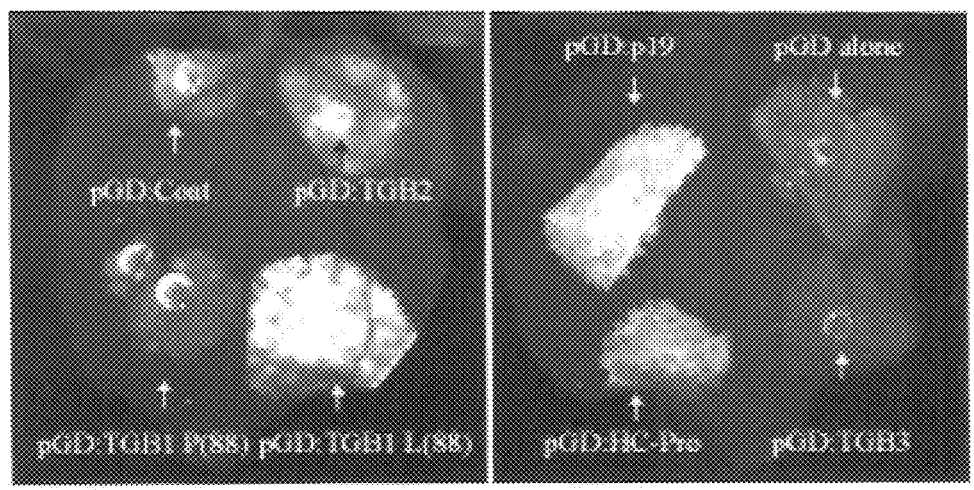
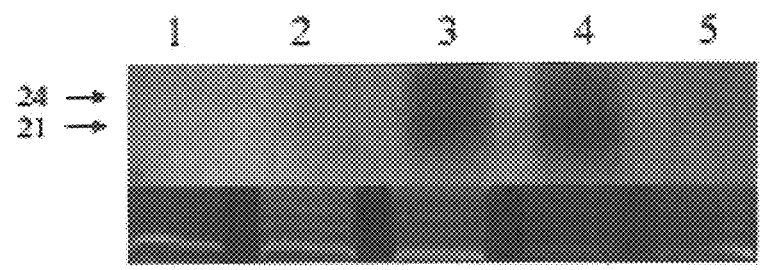
Fig. 10A-B

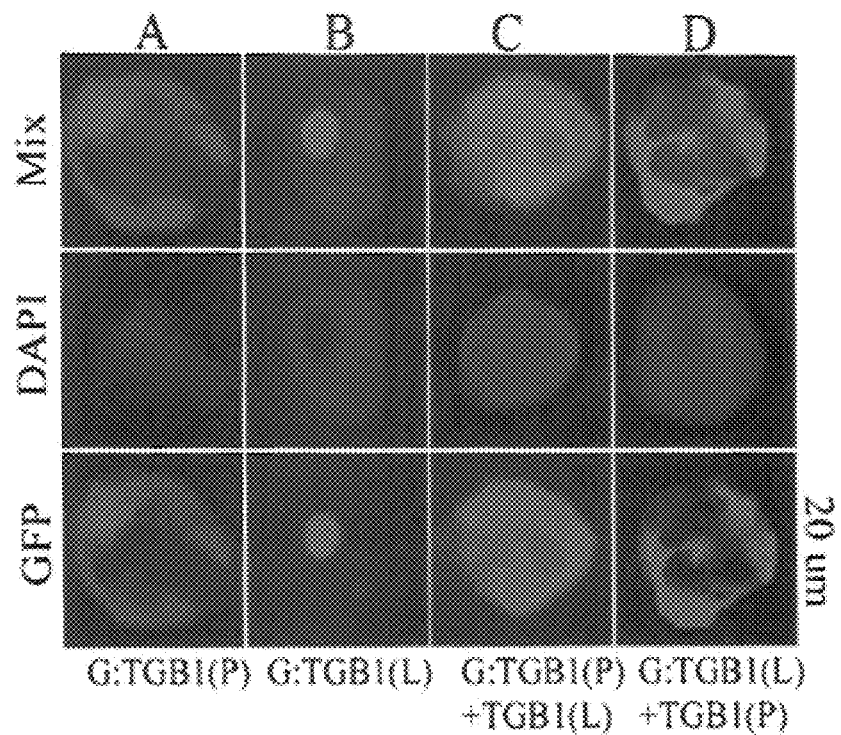
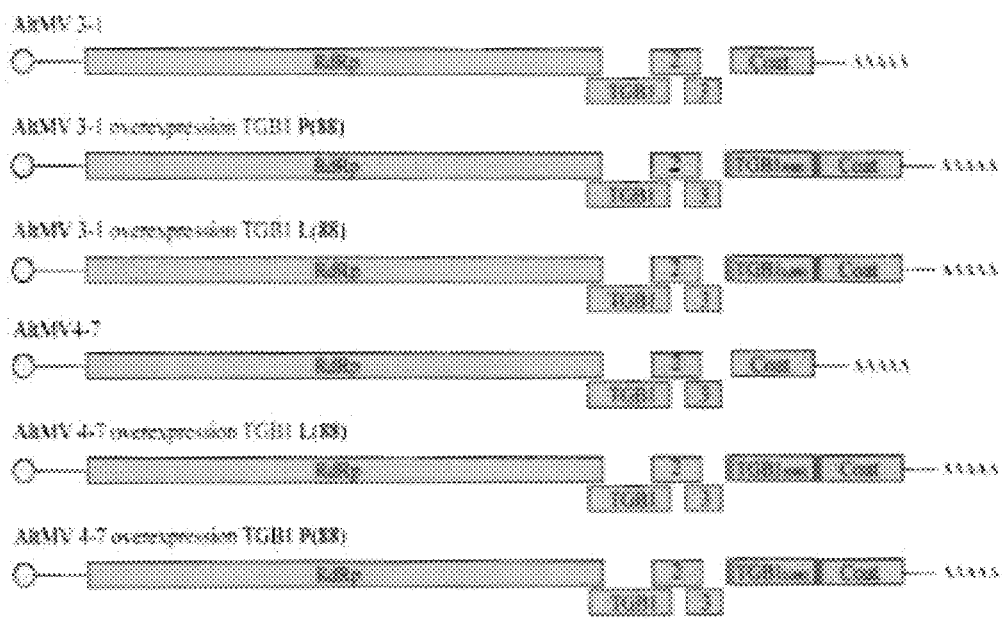
Fig. 11A-E

Fig. 11F-G

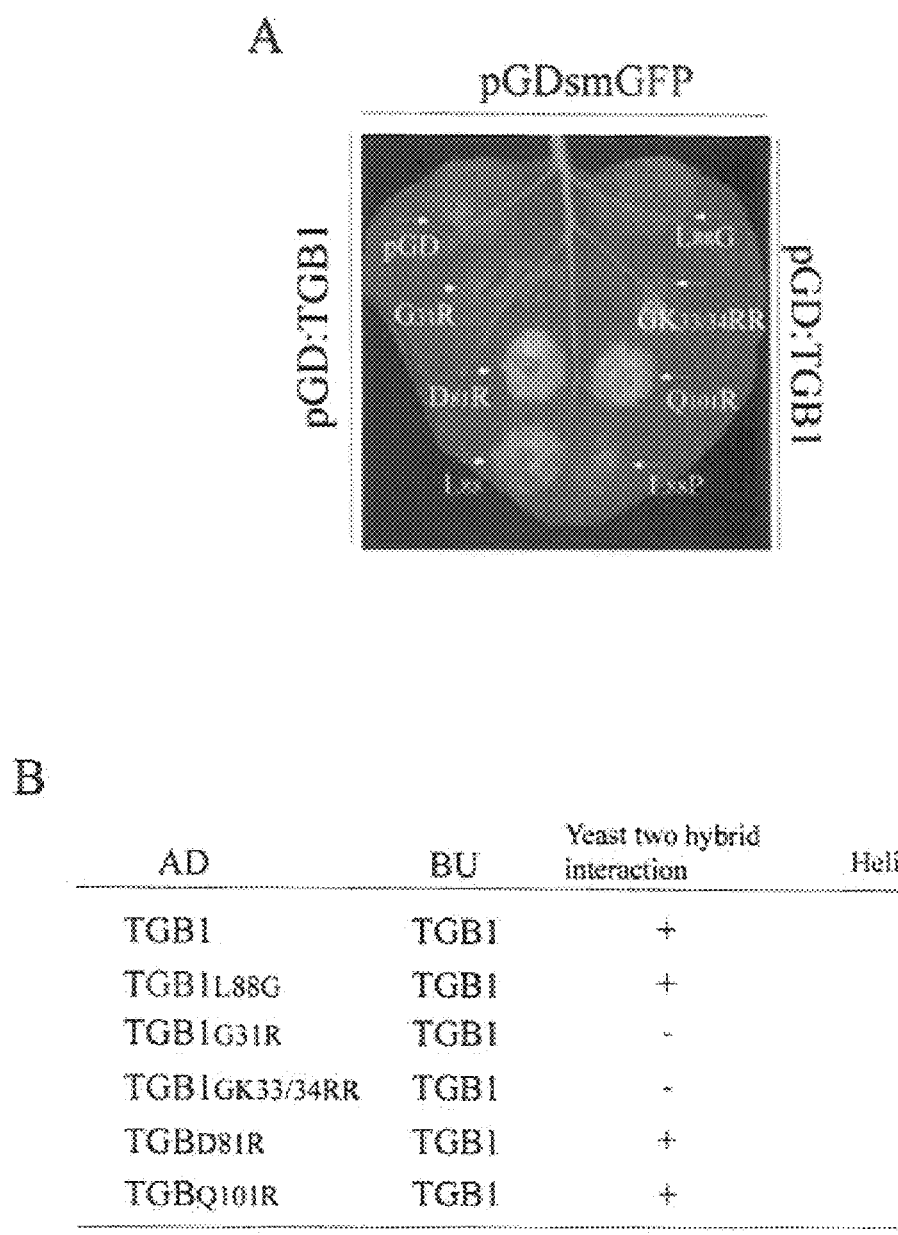
Fig. 12A-B

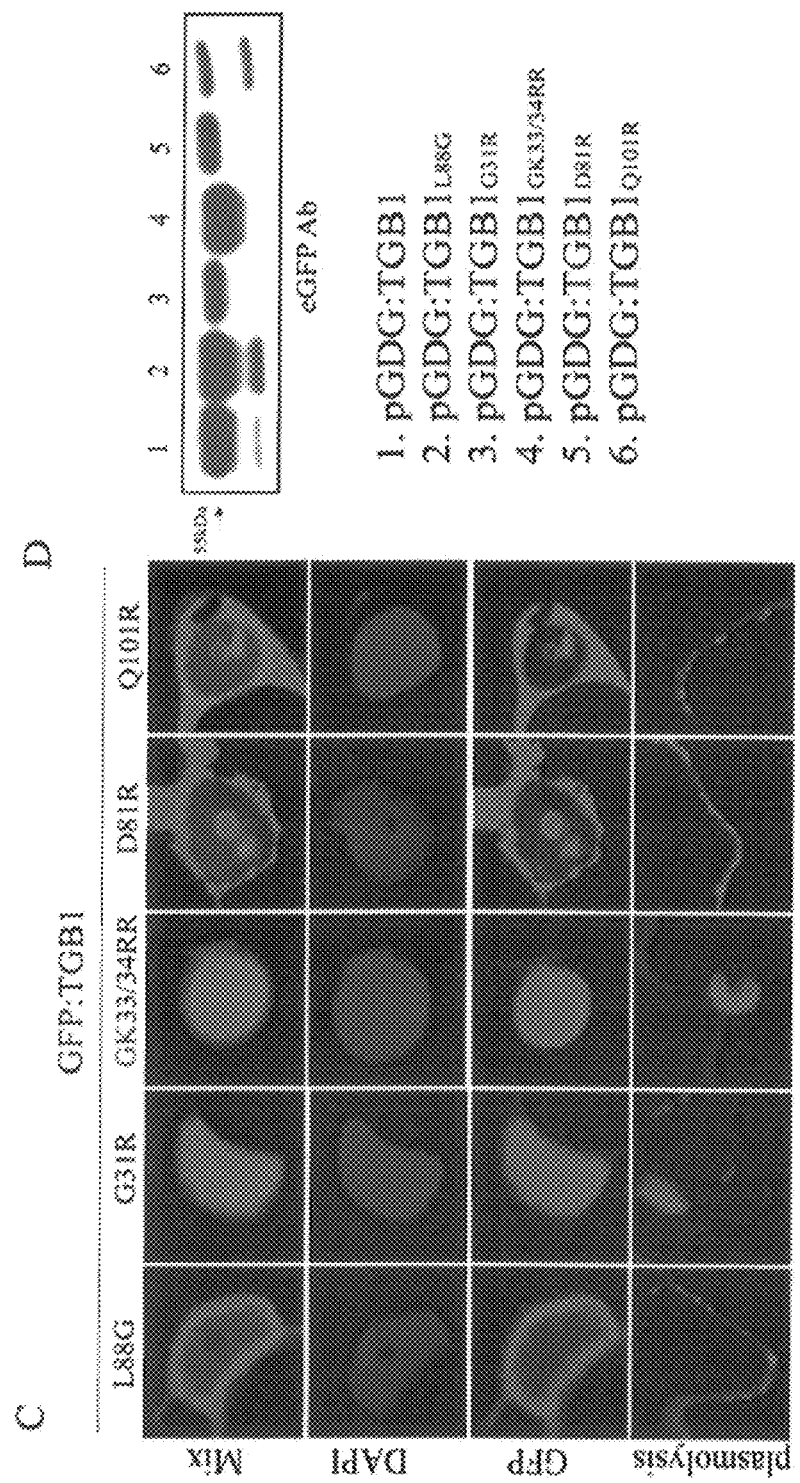
Fig. 12C-D

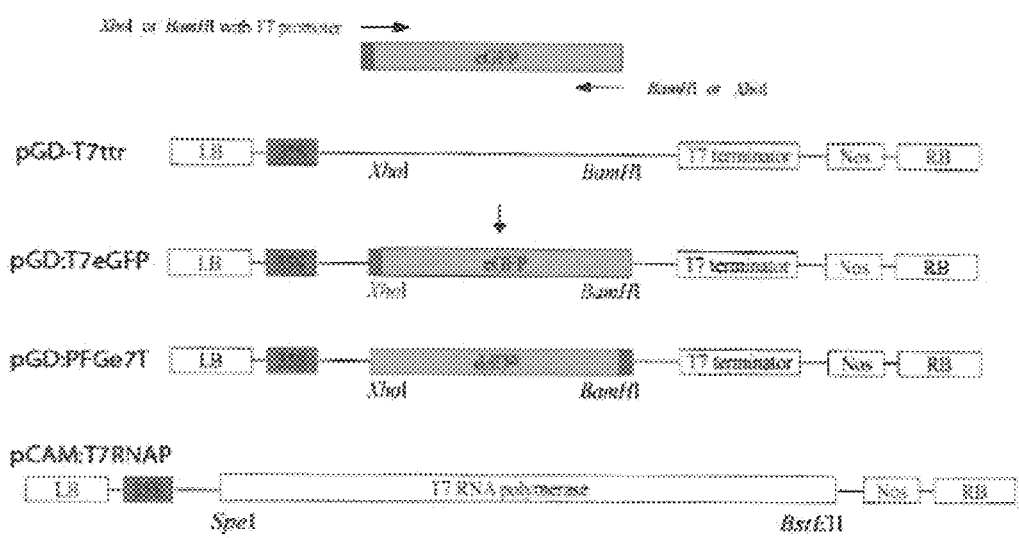
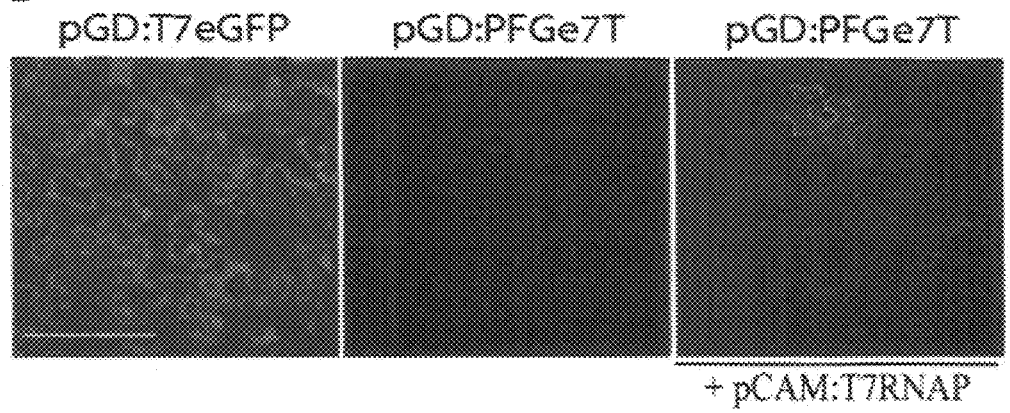
Fig. 15A-B

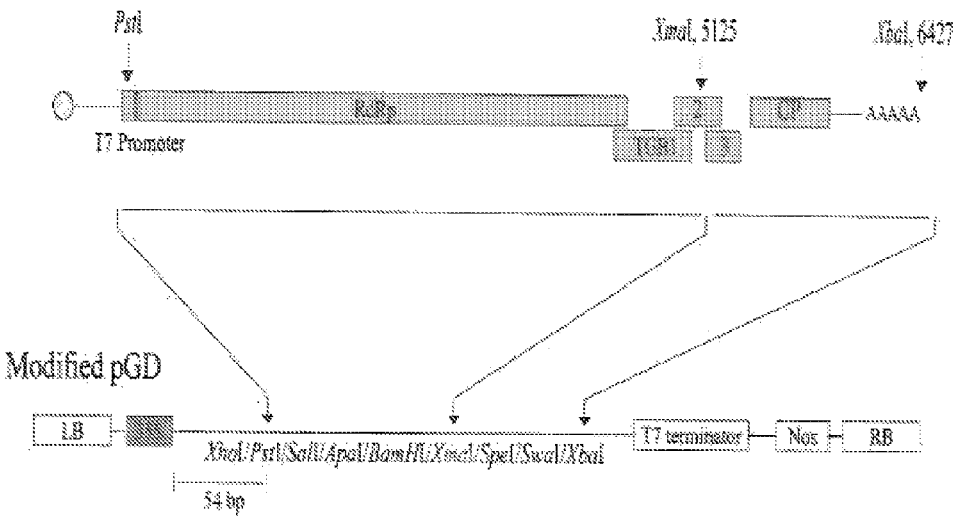
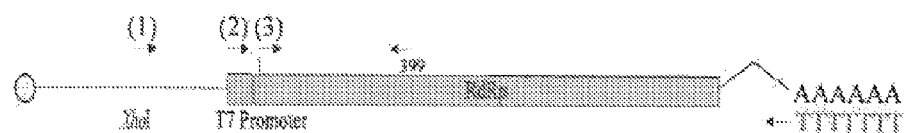
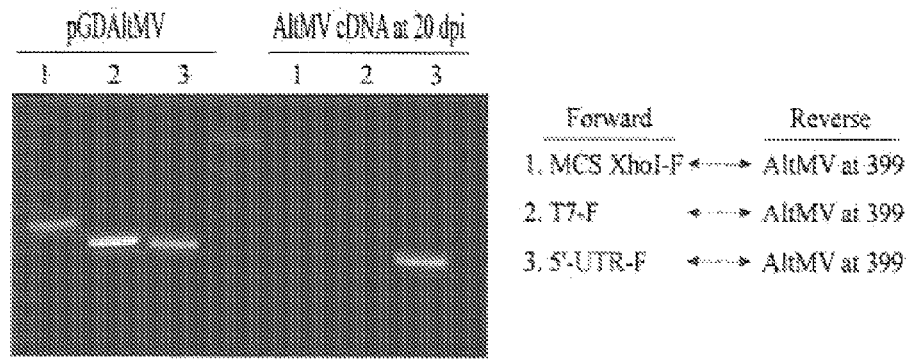
Fig. 16A-B

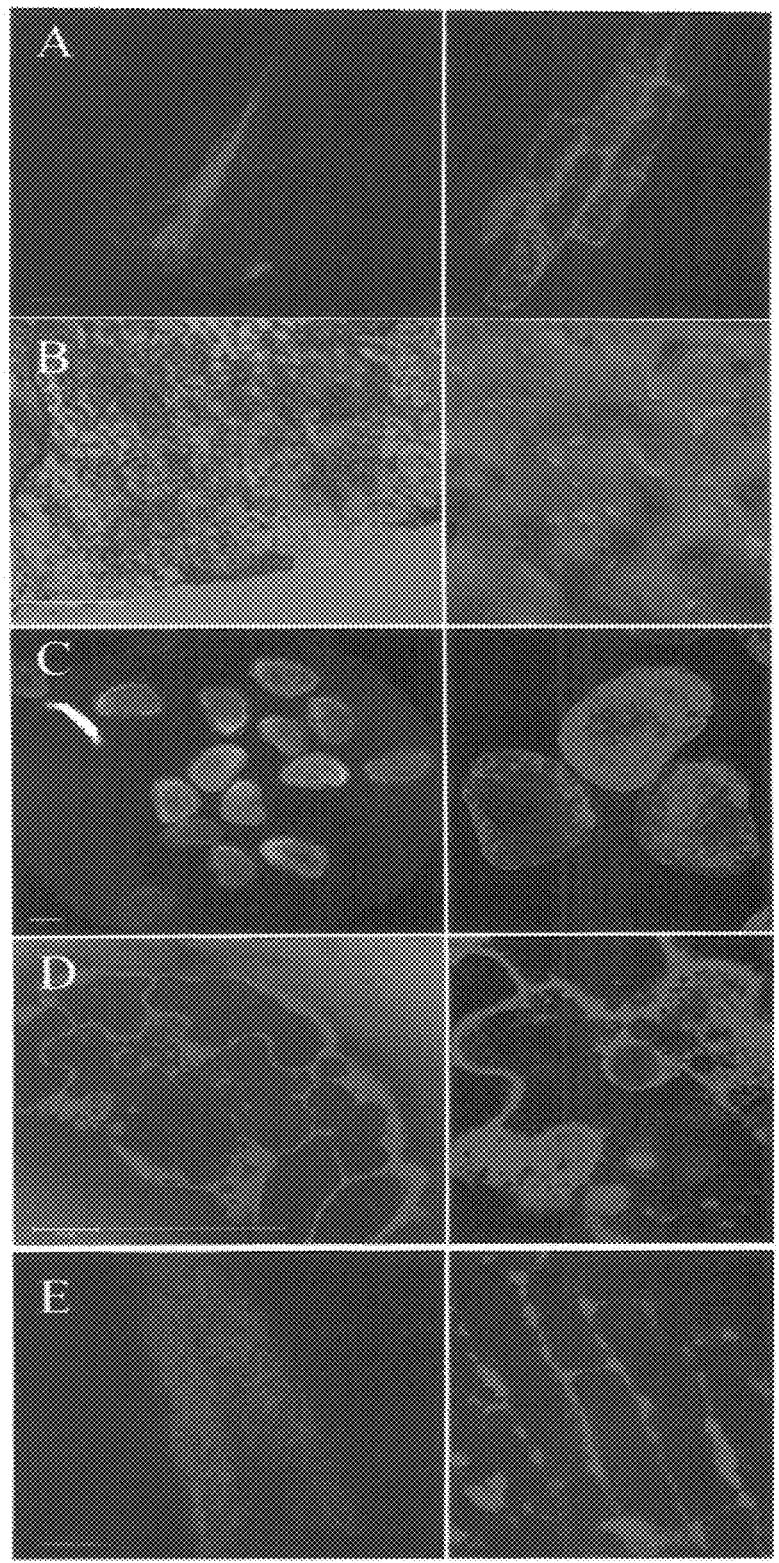
Fig. 17A-E

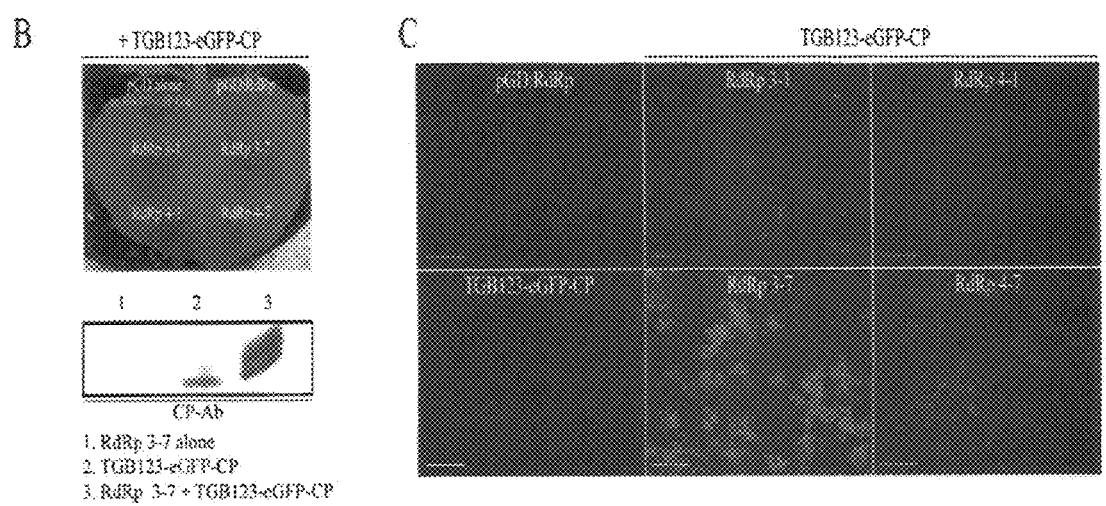
Fig. 18B-C

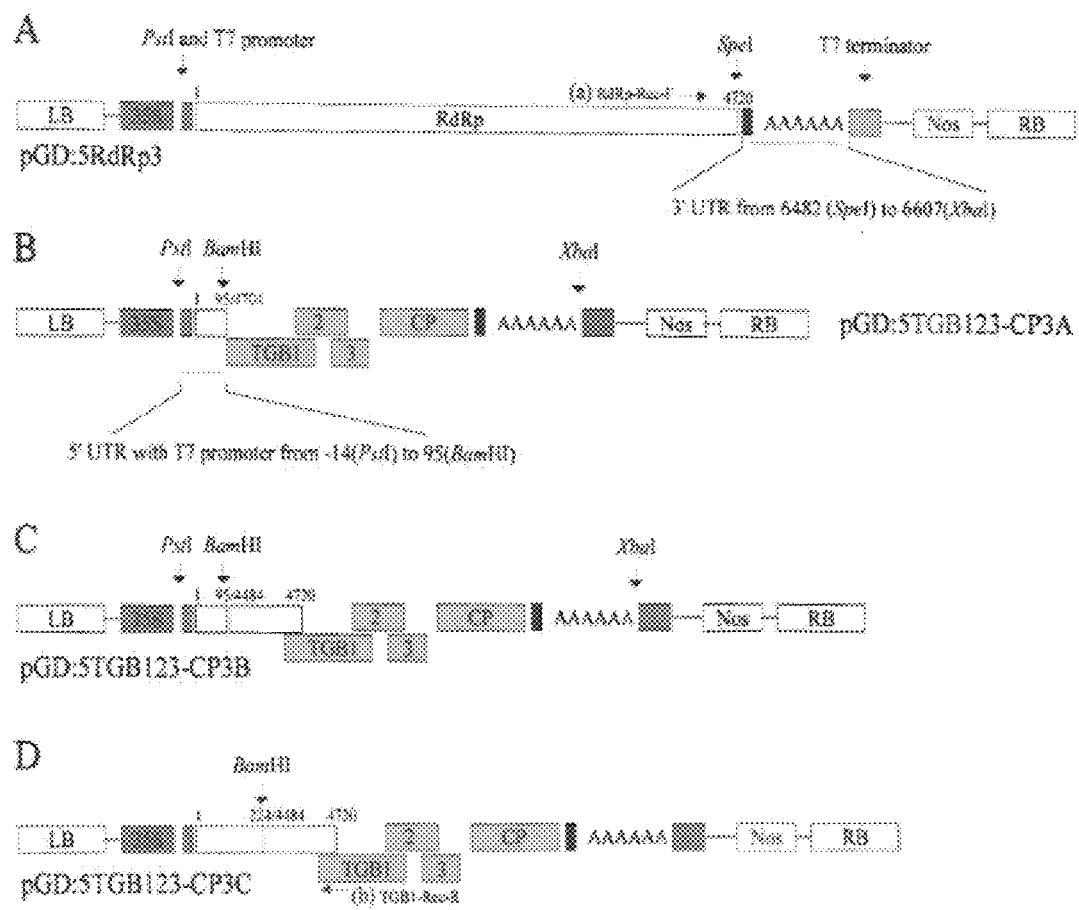
Fig. 19A-D

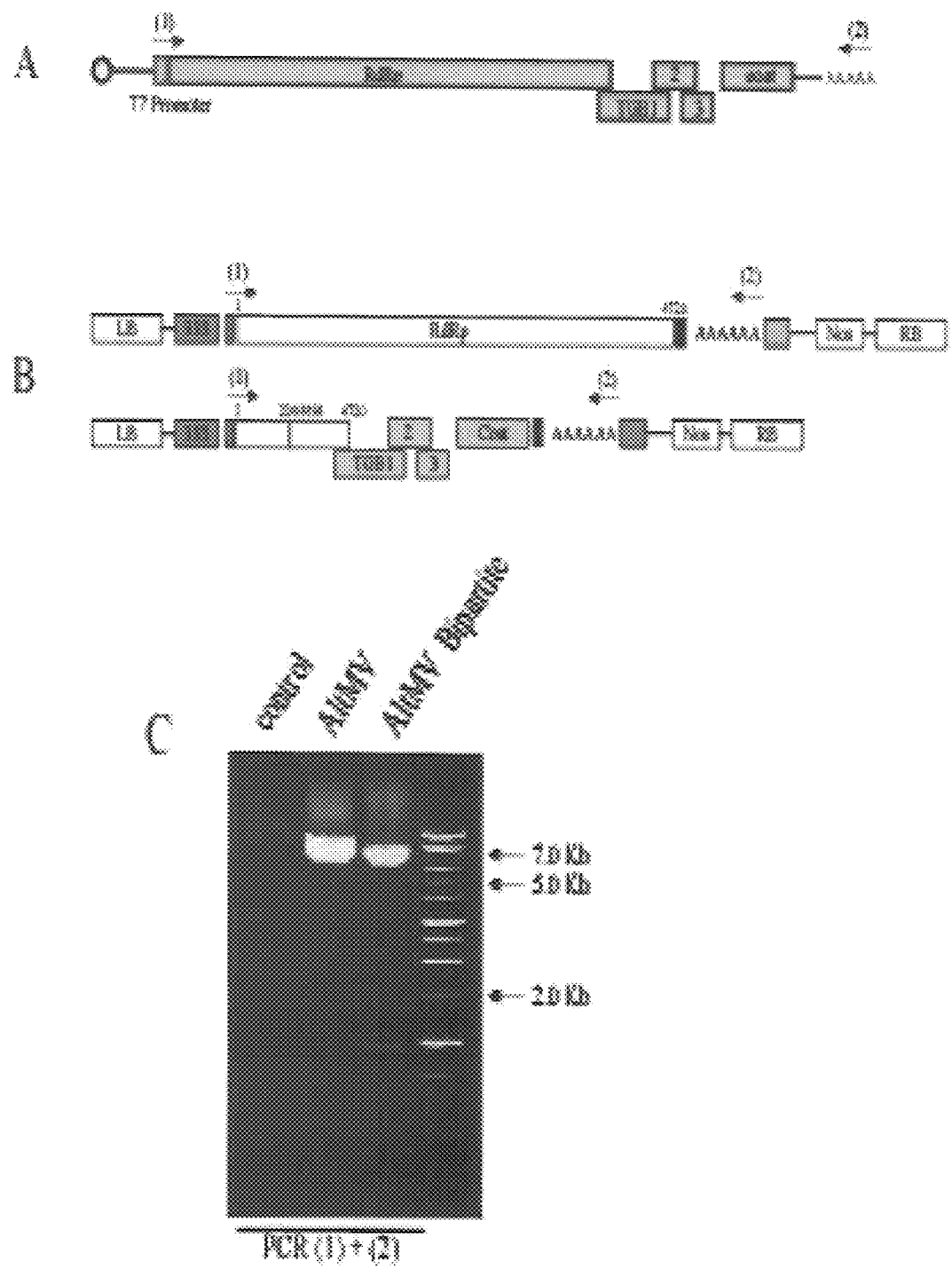
FIG. 20A-C

```
                                              Motif I                      Motif
PVX       MDILISSLKSLGYSRTSKSLDSGP[████████████████]ILRHPTFT[████████]
AltMV P88 MNHFTNLLIEEGYVRTNEIL-SUTLVVHAVA GAGK STLIRKFISQHPQARAYTHGVPDPP
          *.:   . *. .** **.;* * *..***************  ;**;* ;**    ..;* ****

IA              Motif II        Motif III         Motif IV
PVX       [████]QKPGPIPEGN[██████]LDNTTPRSN[█████][█]APEFSLKPH[████████]
AltMV P88 NLEGRFIQAFKNPDPNHFNILDEYCAEP S GGSWN-VLIADPLQHRSQALRPHYIKRESHR
          .;.  * **         .;* ****  ;.; . *.*;*** *  .  .*.**;  . *.*

PVX       [████]RKVAQLIAGCGFDFETNSPEEGHLEITGIPKGPLLGKVIAIDEESETTLSRHGV[████]
AltMV P88 LGVATCELLTRVGLPVLSNKTEG-QVSYQSIFSGPLPGTVIALDSTVRALLVEHGIPPLC
          :  ..;*;;  *;..; *..*; ;;;    ***;***;*.***;*.    .:  * ;**;  ;

Motif V             Motif VI
PVX       [████████████████]APIEEIGQ[██████████████]TVRAGP--------
AltMV P88 PARVLGSEFEQTTVVSEVPLSQVKFKNALYIALT KKSLNVRAPPLPDTPRRLL
          *.;* * **;  ,*;**  ,*;.;;   , *;* *;**  *    ;*** *.
```

B

```
PVX        TAGVPQNPTLDGAYIRKLTI-PESNKLNILDEYAAL--HPLKGSWDVVCADPLQSP-NTA
PlAMV-KNV  TAGTPQSPNLTGAFIRKLTC-PESNKINLLDEYAA S --QPH KGSWDVVLADPLQHT-GLT
ZVX        TLGTPDKPNLTPKMIREYSM-PKANHFNVLDEYCA---QPLKGSWDAVFADPLQHP-DPT
AltMV 3-1  THGVPDPPNLEGRFIQAFKN-PDPNHFNILDEYCA---EPS GGSWNVLIADPLQHR-SQA
AltMV 3-7  THGVPDPPNLEGRFIQAFKN-PDPNHFNILDEYCA---EPLGGSWNVLIADPLQHR-SQA
AltMV-PA   THGVPDPPNLEGRFIQAFKN-PDPNHFNILDEYCA---EPLSGSWNVLIADPLQHR-SQA
AltMV-RU   THGVPDPPNLEGRFIQAFKG-PDPNHFNILDEYCA---EPLGGGWNVLIADPLQHR-SQA
PapMV      THCRADPPNLEGRFIQFFKG-PCFDHFNILDEYCK---SP ISAKFQVLIADPLQYR-TQH
ClYMV      TNGPPDPPTLACTSILPFTGNPFQRTFNILDEYP IG--Q--SKGYKALFADILQHR-NNH
PVX_pP2C2S TLGVPDKVSIRTRGIQKPGPIPEGN-FAILDEYT D --NTTRNSNQALFADPYQAP-EFS
WC1MV      TLGKPDPYSLSNPTIKAFAQFKRG-TLDILDEYGQL PL TSLDSSFEPIFTDPYQAPTDNL
           *   .;   .; *      ; ;****      . ; ;*  *
```

INFECTIOUS PLANT VIRAL VECTOR AND AN ARTIFICIAL BIPARTITE PLANT VIRAL VECTOR AN INFECTIOUS PLANT VIRAL VECTOR AND AN ARTIFICIAL BIPARTITE PLANT VIRAL VECTOR

BACKGROUND OF THE INVENTION

1. Field of the Invention

This invention relates to a novel bipartite plant viral vector launch system for recombination in planta to regenerate full-length infectious virus, a viral vector advantageous for high level replication for protein expression resulting from efficient suppression of RNA silencing and also advantageous for effective virus-induced gene silencing (VIGS) when modified to incorporate weak suppression of RNA silencing, cloned from a potexvirus, Alternanthera mosaic virus (AltMV); constructs containing the required parts of the bipartite viral vectors, constructs containing the RNA-dependent RNA polymerase of AltMV infectious clones, constructs comprising the partial RdRp, TGB1, TGB2, TGB3 and CP of AltMV infectious clones, and such constructs further comprising T7 promoters, Cauliflower mosaic virus (CaMV) 35S promoters, duplicated sub-genomic RNA promoters and multiple cloning sites allowing for additional genes/sequences for expression; vectors containing exogenous T7 RNA polymerase for enhancing infectivity, variant constructs containing modifications to the efficiency of RNA silencing suppression thus enabling VIGS, a method of making a novel bipartite plant viral vector launch system comprising constructs capable of regenerating full-length infectious virus vectors advantageous for both protein expression and VIGS of exogenous genes and sequences, a method of using both the CaMV 35S promoter and the T7 promoters in the same vector making possible both DNA and RNA delivery to drive the transient expression of the infectious viral clones for efficient protein expression and VIGS, a method of ensuring early and enhanced levels of infectivity by including the addition of vectors encoding T7 RNA polymerase, and a method of manipulating the severity of infection by altering the temperature.

2. Description of the Relevant Art

Alternanthera mosaic virus (AltMV) is a potexvirus most closely related to Papaya mosaic virus, and was originally reported from a weed species, *Alternanthera pungens*, in Australia (Geering and Thomas. 1999. *Arch. Virol.* 144:577-592). AltMV has since been reported to infect various ornamental plants, including several *Phlox* species (Hammond et al. 2006a. *Arch. Virol.* 151:477-493; Hammond et al. 2006b. *Acta Horticulturae* 722:71-77), and *Portulaca* (Ciuffo and Turina. 2004. *Plant Pathol.* 53:515; Hammond et al. 2006a,b, supra; Baker et al. 2006. *Plant Disease* 90:833), *Scutellaria* and *Crossandra* (Baker et al., supra), *Angelonia* (Lockhart and Daughtrey. 2008. *Plant Dis.* 92:1473) as well as *Arabidopsis* and soybean (H-S. Lim and J. Hammond, unpublished). The full 6607 nt sequence of one phlox isolate, AltMV-PA, has been reported (GenBank accession no. AY863024), and has a 5' untranslated region (UTR) of 94 nt and a 126 nt 3' UTR excluding the poly(A) tract; there are five open reading frames which encode the RNA-dependent RNA polymerase (RdRp), the triple gene block (TGB) proteins (TGB1, TGB2, TGB3), and the coat protein (CP) (Hammond at al. 2006b, supra). Some differences in symptom expression between isolates have been reported; in *Nicotiana benthamiana*, AltMV-SP (from phlox) and AltMV-PA produce faint chlorotic lesions on the inoculated leaves, followed by systemic chlorotic mosaic, with some rugosity and distortion, while AltMV-Po (from *portulaca*) produced mild symptoms. Under low temperature conditions (<20° C.) AltMV-SP produces necrotic local lesions and severe systemic necrosis (Hammond et al. 2006a, supra) an apparent hypersensitive response. It has also been noted that two geographically distinct isolates from *portulaca* share several coat protein (CP) amino acid residues that distinguish them from *phlox* and *alternanthera* isolates (Hammond et al. 2006a, supra); the complete sequence of a third geographically distinct isolate from *portulaca* has recently become available in GenBank (FJ822136) and the CP amino acid sequence is almost identical to those of the other *portulaca* isolates.

The presence of multiple sequence types, or mixed infection of distinct isolates, within a single plant has been reported for several viruses of different taxonomic groups e.g. capilloviruses (Magome et al. 1997; *Phytopathology* 87:389-396); closteroviruses (Sentandreu et al. 2006. *Arch. Virol.* 151:875-894); potyviruses (Sáenz et al. 2001. *Mol. Plant Microbe Interact.* 14: 278-287); alfalfa mosaic virus (Hull and Plaskitt. 1970. *Virology* 42: 773-776), including potexviruses (e.g. Ozeki et al. 2006. *Arch. Virol.* 151: 2067-2075). As RNA-dependent RNA polymerase lacks a proof-reading activity, RNA virus populations tend to accumulate many minor variations around a master sequence (or multiple master sequences), and thus exist as quasispecies populations (Domingo et al. 1985. *Gene* 40:1-8). Variation within isolates arises by viral polymerase error at a constant rate, but many of the newly generated mutants are sequestered in virions and may not serve as replication templates (Hall et al. 2001. *J. Virol.* 75: 10231-10243). However, the extent of population variation is limited by selection pressure for variants that interact successfully with different host and viral proteins necessary for completion of the infection cycle (Garcia-Arenal et al. 2001. *Annu. Rev. Phytopathol.* 39:157-186; Schneider and Roossinck. 2001. *J. Virol.* 75: 6566-6571; Rico et al. 2006. *J. Virol.* 80: 8124-8132). In order to survive, a virus must be diverse enough to adapt rapidly to changing environments without losing fitness during passage from host to host (Liang et al. 2002. *J. Virol.* 76: 12320-12324). Changing environmental conditions such as temperature can affect virus RNA replication (e.g. Aldaoud et al. 1989. *Intervirology* 30:227-233; Kaper et al. 1995. *Arch. Virol.* 140: 65-74). Genetic exchange plays a role to produce population diversity in bipartite or tripartite viruses (Lin et al. 2004. *J. Virol.* 78:6666-6675); but recombination has also been reported within monopartite viruses such as the potyviruses (Revers et al. 1996. *J. Gen. Virol.* 77: 1953-1965), closteroviruses (Rubio et al. 2001. *J. Virol.* 75: 8054-8062), and between defective potyviral genomes delivered as RNA transcripts (Gal-On et al. 1998; *J. Virol.* 72:5268-5270). There is also some evidence for recombination between isolates of the potexvirus Cymbidium mosaic virus (Sherpa et al. 2007. *J. Biosci.* 32: 663-669; Vaughan et al. 2008. *Arch. Virol.* 153: 1186-1189), although others found no such evidence (Moles et al. 2007. *Arch. Virol.* 152: 705-715), and Malcuit et al. (2000, *Virus Genes* 20: 165-172) have suggested that PVX strain groups evolved through convergent evolution rather than recombination. More recently Draghici and Varrelmann (2009. *J. Virol* 83: 7761-7769) have demonstrated RNA recombination under high selective pressure between defective PVX genomes delivered by agroinfiltration; in this instance the defective genomes either lacked the 5' or the 3' viral untranslated regions (utr) such that no replication of either partial genome alone was possible. Selection may disfavor recombined strains, as a result of incompatibilities between interacting viral proteins, or between viral proteins and cis-acting viral sequences (Malcuit et al., supra). The derivation of distinct Citrus tristeza virus (CTV) lineages by evolution and/or selection from a quasispecies population aided by host passage or aphid transmission has been documented (Sentandreu et al., supra). The origin of variants from a population derived from infectious cDNA clones of Tobacco mosaic virus (Kearney et al. 1999. *Arch. Virol.* 144: 1513-1526; Schneider and Roossinck. 2000. *J. Virol.* 74:3130-3134), Cucumber mosaic virus (CMV) and Cowpea chlorotic mottle virus (Schneider and Roossinck, 2000, supra) has been documented, as has selection from a defined population of CMV variants (Li and Roossinck. 2004. *J. Virol.* 78:10582-10587).

The Potexvirus replicase is a single protein that contains methyltransferase, RNA helicase and RNA polymerase domains (Verchot-Lubicz et al. 2007. *J. Gen. Virol.* 88:1643-1655). A single amino acid change in the Pol domain of Potato virus X (PVX) or Plantago asiatica mosaic virus (PlAMV) RdRp induces systemic necrosis in *N. benthamiana* (Kagiwada et al. 2005. *Virus. Res.* 110:177-182; Ozeki et al., supra). PVX TGB1 has been reported as a suppressor of RNA silencing (Bayne et al. 2005. *Plant J.* 44: 471-482; Voinnet et al. 2000. *Cell* 103:157-167), and to block systemic spread of the silencing signal (Voinnet at al., supra). TGB1, TGB2, TGB3 and coat protein are required for movement; TGB2 and TGB3 are ER binding proteins, and TGB2 has two transmembrane domains and a central motif conserved'among potexviruses that lies in the ER lumen (Verchot-Lubicz at al., supra). PVX CP is an elicitor of the Rx resistance response, and overproduction of CP leads to Rx-mediated hypersensitive response (Bendahmane et al. 1995. *Plant J.* 8: 933-941; Tameling and Baulcombe. 2007. *Plant Cell* 19:1682-1694).

A strategy for use of RNA plant viruses as vectors was proposed by Siegel (Siegel, A. 1983. *Phytopathology* 73: 775) even before infectious clones of any plant viruses had been developed. According to this strategy, the rod-shaped plant viruses offered the greatest possibility as vectors, because the architecture of the particles does not place inherent limitations on the size of the insert; in contrast there are clear packaging constraints with viruses that have isometric particles. Several types of viral vectors have been developed among the rod-shaped and filamentous plant viruses, including gene replacement vectors, exemplified with Tobacco mosaic virus (TMV) by Takamatsu et al. (1987. *EMBO J.* 6: 307-311); gene insertion behind a duplicated subgenomic promoter from the same virus (Dawson et al. 1989. *Virology* 172: 285-292) or a related virus (Culver et al. 1993. *Proc. Natl. Acad. Sci. USA* 90: 2055-2059); translational fusions of partial or complete ORFs to either the N-terminus or C-terminus of a viral structural protein, either with or without a proteolytic cleavage site allowing processing of the fused sequence (e.g. Gopinath et al. 2000. *Virology* 267: 159-173), as a readthrough fusion such that both wild-type and modified viral proteins are produced (Hamamoto at al. 1993. *Bio/Technology* 11: 930-932); epitope display in an internal, surface-exposed loop (Porta at al. 1994. *Virology* 202: 949-955), functional complementation with multicomponent viruses such as Cucumber mosaic virus (Zhao et al. 2000. *Arch. Virol.* 145:2285-2295); functional complementation of a defective RNA by a wild-type virus (Raffo & Dawson. 1991. *Virology* 184: 277-289); chimeric viruses expressing a heterologous viral CP for peptide presentation or epitope display (Yusibov et al. 1997. *Proc. Natl. Acad. Sci. USA* 94: 5784-5788); and viral amplicons delivered from the genome of a transgenic plant (Angell & Baulcombe. 1997. *EMBO J.* 16: 3675-3684) or via agroinfiltration (Liu & Lomonossoff, 2002. *J. Virol. Methods* 105: 343-348). Mallory et al. (2002. *Nat. Biotechnol.* 20:622-625) reported the use of a viral suppressor of RNA silencing to overcome RNA silencing to increase expression from the viral amplicon. Knapp at al. (2005. *Virology* 341: 47-58) have developed a bipartite system from a defective genome of TMV lacking the CP gene, paired with a defective RNA having an internally deleted replicase gene and a functional CP gene flanked by the TMV 5' and 3' TMV utr. Although this bipartite form was maintained in systemic infections, systemic movement was significantly debilitated (Knapp et al. 2007. *Virology* 367:82-91).

Replication of defective genomes in the presence of a fully functional genome occurs in several plant viral systems; in some cases replication of a 'defective interfering" (DI) RNA inhibits replication of the functional genome (e.g. Jones et al. 1990. *Virology* 176:539-545). In other cases the DI RNA may intensify symptom expression (e.g. Li et al. 1989. *Proc Natl Acad Sci USA* 86, 9173-9177).

A further extension of hybrid viruses, combined with complementation, has been described. Marillonet et al. (2004. *Proc Natl Acad Sci USA* 101: 6852-6857) and Gleba et al. (2004. *Curr. Opin. Plant Biol.* 7: 182-188) have developed systems in which viral functions not needed for expression can be dispensed with, and complementation used to provide equivalent functions from other sources; this has been described as the 'deconstructed virus' approach; expression can be optimized by elimination of functions not needed for expression. This may also aid in biocontainment, by elimination of functions contributing to vectored transmission. An efficient means of delivery of multiple separate components by agroinfiltration, combined with in planta recombination through co-expression of a recombinase, was shown to both confer high yields, and to allow greater flexibility in comparing variants of one or more system components. One or more component may be supplied as a transgene, and induction of replication and expression may be regulated by use of either a developmentally-controlled promoter, or by application of an inducer (Gleba et al. 2004, supra).

Taschner et al. (1991. *Virology* 181: 445-450) transformed plants with the replicase functions of Alfalfa mosaic virus (AlMV), while Mori et al (1992. *J. Gen. Virol.* 73: 169-172) similarly transformed plants with the replicase functions of Brome mosaic virus; Sanchez-Navarro et al. (2001. *Arch. Virol.* 146: 923-929) engineered RNA3 of AlMV into an expression vector using the replicase-expressing plants.

Virus-Induced Gene Silencing (VIGS) has become a significant tool for discovery of gene function in both dicotyledonous (Ratcliff of al. 2001. *Plant J.* 25: 237-245; Liu et al. 2002. *Plant J.* 31: 777-786) and monocotyledonous (Holzberg et al. 2002. *Plant J.* 30: 315-327) species. Although some viral vectors have been utilized for both protein expression and VIGS, including PVX (Chapman et al. 1992. *Plant J.* 2: 549-557; Ruiz of al. 1998, *Plant Cell* 10: 937-946) and Bean pod mottle virus (BPMV; Zhang & Ghabrial. 2006. *Virology* 344: 401-411), it is generally recognized that for high level protein expression, a virus with an effective suppressor of RNA silencing is desirable, whereas for VIGS, a less effective viral suppressor of RNA silencing is preferred (Dalmay of al. 2000. *Plant Cell* 12: 369-379). Indeed, it has been noted that BPMV does not effectively suppress RNA silencing, and that expression of an effective suppressor of RNA silencing in combination with BPMV vectors may be useful for enhancing foreign protein expression, which would probably need to be expressed from a co-infecting recombinant BPMV vector (Zhang and Ghabrial 2006, supra). BPMV has either weak or no suppressor of RNA silencing (Zhang and Ghabrial 2006, supra), and is more useful as a VIGS vector (Zhang et al. 2009. *Mol. Plant—Microbe Interact.* 22:123-131). PVX may fall into a middle group, as replication of PVX is significantly enhanced in a mixed infection with a potyvirus, as a consequence of the efficient suppression of RNA silencing provided by the potyvirus HC-Pro (Pruss et al. 1997. *Plant Cell* 9: 859-868), although PVX has its own suppressor of RNA silencing in TGB1 (Voinnet et al. 2000. *Cell* 103: 157-167).

Infectious clones of potexviruses including PVX (Hemenway et al. 1990. *Virology* 175: 365-371) have been developed and used as vectors for gene expression in plants (Chapman et al. 1992, supra) and for VIGS (Ruiz et al. 1998, supra). Separate constructs of infectious PVX clones driven by the Cauliflower mosaic virus (CaMV) 35S promoter and the bacteriophage T7 promoter have been reported (Baulcombe et al. 1995. *Plant J.* 7: 1045-1053). An infectious monopartite clone of PVX has been placed into a binary *Agrobacterium* vector under the control of the CaMV 35S promoter, and further modified with unique restriction enzymes in a Multiple Cloning Site (MCS) to allow high throughput cloning and expression of suitably constructed cDNA libraries (Takken et al. 2000. *Plant J.* 24: 275-283).

The bacteriophage T7 RNA polymerase (T7RNAP) is well known, and has previously been utilized from a chromosomal insertion for high-level expression of genes in bacteria (Studier & Moffatt. 1986. *J Mol Biol.* 189:113-130); in mammalian cells when T7RNAP was itself expressed from a recombinant vaccinia virus (Fuerst at al. 1986. *Proc Natl Acad Sci USA.* 83:8122-8126); and in insect cells when T7RNAP was delivered from a recombinant baculovirus (van Poelwijk et al. 1995. *Biotechnology (NY)*. 13:261-264). The T7RNAP has also been used under the control of appropriate promoters for both tissue-specific and inducible expression in transgenic plants (Nguyen et al. 2004. *Plant Biotechnol J* 2, 301-310). Replication of the RNA of an insect virus was initiated (Ball. 1995. *J. Virol.* 69:720-727), and infectious rabies virus recovered in mammalian cells (Schnell et al. 1994. *EMBO J.* 13:4195-4203) using the vaccinia/T7 system. Infectious poliovirus was recovered from mammalian cells using the baculovirus/T7 system (Yap et al. 1997. *Virology* 231: 192-200). Reverse-genetics systems for negative-strand viruses are also often based on transcription of viral RNA by the bacteriophage T7 RNA polymerase (de Wit at al. 2007. *J Gen Virol* 88: 1281-1287). A hybrid baculovirus-T7 RNA polymerase system has been used for transient expression in mammalian cells (Yap et al. 1997, supra). The RNA minigenome system has been used for evaluating the functions of viral proteins and of sequences involved in viral RNA replication (Lohmann et al. 1999. *Science* 285: 110-113). Much of the work on the role of the 5' and 3 UTR in viral replication has been through use of the minigenome (Dumas et al. 2007. *J Virol Methods* 142: 59-66; Friebe at al. 2001. *J. Virol.* 75: 12047-12057).

In summary, agroinfiltration, biolistic delivery of plasmid or transcripts, and mechanical inoculation of either plasmids or in vitro transcripts are the main methods for delivery of viral nucleic acids into cells. Agroinfiltration is relatively easy to apply with low cost; however, not all plant species are susceptible to agroinfiltration. In contrast, most plant species can be infected by biolistic delivery or mechanical inoculation with plasmids or in vitro transcripts, but the technique is more laborious and expensive than agroinfiltration. Each method has advantages, and disadvantages, but since most virus-based vectors are constructed with a single promoter sequence, it has not typically been possible to use both DNA and RNA delivery methods with the same vector. In addition, many plant viruses have been modified, for either protein expression or gene silencing. However, a single plant virus-based vector has been unable to effectively fulfill both functions because of the conflicting requirements for strong or weak RNA silencing suppression, respectively, for protein expression and VIGS.

Thus, there is a need for the development of alternative viral vector systems which have flexibility for modification and variation and which are applicable for effective in planta transient expression of multiple genes. We show here that the genome of representative potexviruses can be manipulated to serve as new bipartite plant viral vector launch systems for recombination in planta to regenerate full length infectious viruses, viral vectors effective for high levels of protein expression, and manipulated differently, for effective virus-induced gene silencing.

SUMMARY OF THE INVENTION

We have discovered that the genome of a potexvirus, Alternanthera mosaic virus (AltMV) can be manipulated to generate a novel bipartite plant viral vector launch system for recombination in planta to regenerate full-length infectious virus and that the function of such virus-based vectors can be easily changed from protein expression to virus-induced gene silencing, that they can be introduced into plants by either agroinfiltration or, in plant species recalcitrant to *Agrobacterium*-mediated inoculation, by mechanical inoculation of in vitro transcripts, and that T7 RNA polymerase and reverse genetic systems can be applied for developing this novel viral vector applicable to *Arabidopsis* and soybean in addition to *Nicotiana benthamiana* and a number of ornamental species.

In accordance with this discovery, it is an object of the invention to provide a novel bipartite plant viral vector launch system for recombination in planta to regenerate full-length infectious virus, a viral vector advantageous for high level replication for protein expression when maintaining endogenous efficient suppression of RNA silencing and for effective virus-induced gene silencing when modified for weak suppression of RNA silencing.

It is an object of the invention to provide recombinant nucleotide sequences comprising the bipartite launch system: the 5'utr (untranslated region)-RdRp (RNA-dependent RNA polymerase)-3'utr construct plus the 5'utr-partial RdRp/TGB1 (Triple. Gene Block 1), TGB2, TGB3/sgPro (subgenomic promoter)-MCS (multiple cloning site)-sgPro/CP (coat protein)-3'utr construct, wherein the T7 promoter is present in the nucleotide sequence immediately upstream of each AltMV 5'utr, and each construct is inoculated into plants, resulting in recombination in planta to regenerate full-length infectious virus, said recombination occurring within, a short overlap of a common sequence present in both constructs of the bipartite vector system (resulting from TGB1 initiating 16 nt upstream of the RdRp termination region).

It is a further object of the invention to provide recombinant nucleotide sequences comprising the bipartite launch system: the 5'utr-RdRp-3'utr modified pGD cDNA construct plus the 5'utr-partial RdRp/TGB1, TGB2, TGB3/sgPro-MCS-sgPro/CP-3'utr modified pGD cDNA construct, wherein the T7 promoter is present in the nucleotide sequence immediately upstream of each AltMV 5'utr and in addition a CaMV 35S promoter is located upstream from each T7 promoter, each construct delivered by *Agrobacterium*-mediated inoculation, resulting in recombination in planta to regenerate full-length infectious virus.

It is an additional object of the invention to provide recombinant nucleotide sequences comprising the bipartite launch system: the 5'utr-RdRp-3'utr modified pGD cDNA construct plus the 5'utr-partial RdRp/TGB1, TGB2, TGB3/sgPro-MCS-sgPro/CP-3'utr modified pGD cDNA construct, wherein the T7 promoter is present in the nucleotide sequence immediately upstream of each AltMV 5'utr, a CaMV 35S promoter is located upstream from each T7 promoter, and in addition, a construct encoding the T7 RNA polymerase (T7RNAP) is added, each construct delivered by *Agrobacterium*-mediated inoculation, resulting in recombination in planta to regenerate full-length infectious virus.

It is another object of the invention to provide recombinant nucleotide sequences comprising the bipartite launch system: 5'utr-RdRp-3'utr plus 5'utr-partial RdRp/TGB1, TGB2, TGB3/sgPro-MCS-sgPro/CP 3'utr wherein the bipartite launch system comprises chimeric constructs having anyone; or more of the substitutions R(1110)P, K(1121)R, and R(1255)K in Pol, S(1535)P in RdRp in the RdRp C-terminal region and P(88)L in TGB1.

It is a still further object of the invention to provide recombinant nucleotide sequences comprising the bipartite launch system: 5'utr-RdRp-3'utr plus 5'utr-partial RdRp/TGB1, 2, 3/sgPro-MCS-sgPro/CP-3'utr together with RNA transcripts for the T7 polymerase in conjunction with the 35S promoter to increase efficiency of transcription via *Agrobacterium*-mediated inoculation to establish infectious virus in a shorter time and with higher efficiency.

It is still another object of the invention to provide recombinant nucleotide sequences comprising the bipartite launch system: 5'utr RdRp-3'utr plus 5'utr-partial RdRp/TGB1, 2, 3/sgPro-MCS-sgPro/CP-3'utr wherein the nucleotide sequence encoding leucine at amino acid 88 of TGB1 is maintained resulting in a vector to be used advantageously for high level protein expression.

It is another object of the invention to provide recombinant nucleotide sequences comprising the bipartite launch system: 5'utr-RdRp-3'utr plus 5'utr-partial RdRp/TGB1, 2, 3/sgPro-MCS-sgPro/CP-3'utr wherein the nucleotide sequence encoding leucine at amino acid 88 of TGB1 is maintained and an additional strong suppressor of silencing, such as tombusvirus p19, is present resulting in a vector to be used advantageously for high level protein expression.

It is an additional object of the invention to provide recombinant nucleotide sequences comprising the bipartite launch system: 5'utr RdRp-3'utr plus 5'utr-partial RdRp/TGB1,2,3/sgPro-MCS/CP 3'utr wherein the nucleotide sequence encoding amino acid 88 of TGB1 is modified resulting in the amino acid substitution of proline for leucine and thereby converting TGB1 of AltMV from an effective silencing suppressor to a weak suppressor of RNA silencing, resulting in the AltMV vector to be used advantageously for virus-induced gene silencing (VIGS).

It is a still another object of the invention to provide recombinant nucleotide sequences comprising the bipartite launch system: 5'utr-RdRp-3'utr plus 5'utr-partial RdRp/TGB1, 2,3/sgPro-MCS-sgPro/CP-3'utr wherein the nucleotide sequence of TGB1 is modified to reflect a single or dual amino acid substitution, L->P or LL->P thereby converting TGB1 of AltMV and other Flexiviridae members from effective silencing suppressors to weak suppressors of RNA silencing thus resulting in variants of the same vector to be used for high level protein expression or for virus-induced gene silencing, respectively and wherein the Flexiviridae members of the genus Potexvirus having equivalent single amino acid changes in a comparable region of TGB1 are Potato virus X (PVX), or dual amino changes in PlAMV-NMV, the Nandina mosaic virus isolate of Plantago asiatica mosaic virus.

It is a still further object of the invention to provide constructs and vectors which comprise the nucleotide sequences of the two parts of the bipartite launch system.

It is another object of the invention to provide a host cell comprising the vector containing the constructs comprising the bipartite launch system of Alternanthera mosaic virus (AltMV) and other members of the Flexiviridae.

It is an additional object of the invention to provide RdRp as a transgene without 5' and 3' UTR to serve as a biocontainment system preventing the formation of infectious virus.

It is another object of the invention to provide a method of using the nucleotide sequences of a bipartite plant viral vector launch system for recombination in planta to regenerate full-length infectious virus, viral vectors advantageous for high level replication for protein expression when efficient suppression of RNA silencing is maintained and operably linked with the promoters of the bipartite system, capable of driving expression of a gene in a plant cell.

It is another object of the invention to provide a method of using the nucleotide sequences of a bipartite plant viral vector launch system for recombination in planta to regenerate full-length infectious virus, viral vectors advantageous for effective virus-induced gene silencing when incorporating weak suppression of RNA silencing, operably linked with the promoters of the bipartite system, capable of driving expression of a gene in a plant cell.

It is still another object of the invention to provide a method of manipulating the nucleotide sequences of a bipartite plant viral vector launch system for recombination in planta to regenerate full-length infectious virus and to obtain viral vectors to affect efficiency of silencing suppression thus converting TGB1 of AltMV and other Flexiviridae from effective silencing suppressors to weak suppressors of RNA silencing resulting in a variant infectious virus or vector to be used for high level protein expression or incorporating weak suppression of RNA silencing resulting in a variant infectious virus or vector to be used for effective virus-induced gene silencing.

It is yet another object of the invention to provide plants, plant cells, and plant parts, and plant seeds which have been infected by the bipartite plant viral vector launch system of the invention.

It is an additional object of the invention to provide a method of attenuating severe symptoms by manipulating levels of protein expression by substitution of domains in TGB1, and RdRp (including the Pol domain).

It is an additional object of the invention to provide a method of reducing symptom expression and ablating necrosis without affecting replication efficiency and protein expression by substituting the CP of AltMV-Po for CP of AltMV-SP.

It is another object of the invention to provide a method of increasing replication and levels of protein expression by growing the plants at temperatures lower than 25° C.

It is still another object of the invention to provide a method of using the nucleotide sequences of a bipartite plant viral vector launch system for recombination in planta to regenerate full-length infectious virus vectors advantageous for high level protein expression of multiple genes and sequences by maintaining the original TGB1 sequence and efficiency of silencing suppression of AltMV and other Flexiviridae.

It is another object of the invention to provide a method of increasing expression still more by manipulating the system by adding additional suppressors of silencing, by adding constructs encoding T7 RNA polymerase, and by altering the temperature.

It is an additional object of the invention to provide a method of using the nucleotide sequences of a bipartite plant viral vector launch system for recombination in planta to regenerate full-length variant infectious virus vectors advantageous for effective virus-induced gene silencing when the TGB1 sequence of AltMV and other Flexiviridae has been modified to a weak suppressor of RNA silencing.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1 depicts the derivation of the full-length infectious clones 3-1, 3-7, 4-1, and 4-7 and their effects in planta. FIG. 1A depicts full-length clones derived from AltMV-SP by population cloning, including ligation at the nt3125 Mlu I site and the infectious clones 3-1, 3-7, 4-1, and 4-7. FIG. 1B shows that the symptoms produced by each clone (shown at 20 dpi) are distinct from each other and AltMV-SP. Symptoms are more severe at 15° C. (lower) than at 25° C. (upper). All clones together (Mix; 3-1+3-7+4-1+4-7) produced symptoms milder than AltMV-SP.

FIG. 3A depicts the determination of sequence variants present in AltMV-SP-infected $N.$ benthamiana. RT-PCR products across the Mlu I clone junction from nt 2709 to 3505 were cloned; 15 clones were sequenced. Numbers of clones of each type are indicated. The Mlu I site and nucleotides differentiating the sequence types are indicated; namely, the nucleotide (nt) in position 3112 of the depicted portion [nt3106-nt3130] of SEQ ID NO:4 for AltMV 4-1, of SEQ ID NO:1 for AltMV 4-7, of SEQ ID NO:2 for AltMV 3-1, of SEQ ID NO:3 for AltMV 3-7, and the nt in position 3456 of the depicted portion [nt3445-nt3461] of the same sequence; dashes indicate nucleotides identical in each viral clone and PCR product. FIG. 3B shows the results of Q-RTPCR of $N.$ benthamiana infected with AltMV-SP, 3-1, 4-7, or [3-1+4-7] normalized to actin. The average value and standard deviation of four $N.$ benthamiana is shown for: 30 dpi at 25° C. (left); 1.0 dpi at 15° C. (middle); and 30 dpi at 15° C. (right). RNA accumulation was significantly higher at 15° C. than at 25° C.; AltMV 4-7 alone killed plants prior to 30 dpi at 15° C. Values indicated by the same letter were not significantly different (LSD (P=0.05)=1.2×105).

FIG. 4A depicts the insertion of eGFP and DsRed between TGB3 and CP of AltMV 3-1 and 4-7, respectively, under control of a duplicated. CP sub-genomic promoter. AltMV 4-1 was similarly labeled with eGFP, and 3-7 with DsRed. FIG. 4B-4D shows that 3-1:eGFP and 4-7:DsRed were co-inoculated to $N.$ benthamiana at 25° C. or 15° C. The youngest expanded leaf was observed by confocal microscopy at: 30 dpi, 25° C. (FIG. 4B) and 30 dpi, 15° C. (FIG. 4C). (FIG. 4D) shows the outlined region of panel 4C at higher magnification; images shown represent: (top) overlay of GFP and DsRed, (middle) GFP alone, and (bottom) DsRed alone; Bars represent 100 µm. (FIG. 4E) shows the relative occurrence of 3-1:eGFP and 4-7:DsRed in upper leaves. PCR products of the MluI clone junction region amplified from upper leaves at 30 dpi as in 4C and 4D were cloned and sequenced to determine abundance of each sequence type: namely, the depicted portion [nt3106-nt3461] of SEQ ID NO:2 for AltMV 3-1 and of SEQ ID NO:1 for AltMV 4-7. FIG. 4F shows fluorescence of eGFP expressed from AltMV 4-1eGFP, and DsRed expressed from AltMV 3-7DsRed at 10 dpi (upper) and 30 dpi (lower) in plants inoculated with both infectious clones. Left panel, overlay of eGFP and DsRed images; center panel, eGFP image alone; right-panel, DsRed image alone. A small number of cells expressing eGFP were detected at 10 dpi, but none in upper leaves at 30 dpi, suggesting that AltMV 4-1eGFP was unable to compete and spread in the presence of 3-7DsRed.

FIG. 5 shows the effects of mild clone AltMV 4-1 substituted with [Pol], [TGB1], and [Pol+TGB1] domains of severe clone 3-7; and 3-7 substituted with [Pol], and [TgB1] of 4-1. FIG. 5A shows three of the five hybrid clones that were created: $4\text{-}1_{PRK}$, $4\text{-}1_L$, $4\text{-}1_{PRKL}$; $3\text{-}7_{RKR}$ and $3\text{-}7_P$ are the reciprocal hybrids of $4\text{-}1_{PRK}$ and $4\text{-}1_L$, respectively. FIG. 5B shows that 4-1 and each derivative clone were inoculated to $N.$ benthamiana; symptoms are shown at 30 dpi in plants inoculated with 4-1, $4\text{-}1_{PRK}$, $4\text{-}1_L$ and $4\text{-}1_{PRKL}$ FIG. 5C depicts the Q-RTPCR comparison of 4-1, $4\text{-}1_{PRK}$, $4\text{-}1_L$ and $4\text{-}1_{PRKL}$ accumulation levels at 30 dpi.

FIGS. 6A and B depict the substitution of the AltMV-Po coat protein (CP) gene into infectious AltMV clone 3-7. FIG. 6A is a cartoon of infectious clone AltMV 3-7 (upper), showing the Nco I site used to substitute the AltMV-Po CP gene (middle), creating clone AltMV $3\text{-}7_{CP\text{-}Po}$ (lower). FIG. 6B depicts symptoms of AltMV 3-7 (left) and AltMV $3\text{-}7_{CP\text{-}Po}$ (right) in Nicotiana benthamiana at 15° C. Note that 3-7 induced necrosis, whereas $3\text{-}7_{CP\text{-}Po}$ caused only mild mosaic.

FIGS. 7A and B show that AltMV-SP (3-7) and AltMV-Po coat proteins (CP) display different degrees of self-interaction. FIG. 7A depicts yeast two-hybrid self-interactions of the CP of AltMV-Sp (3-7) and AltMV-Po, demonstrating (1) strong growth indicating strong self-interaction of AltMV-SP CP; (2) lack of interaction with the Gal4 binding domain (BD) negative control; (3) weak growth resulting from weak self-interaction of AltMV-Po CP; and (4) lack of interaction with Gal4 activation domain (AD) negative control. FIG. 7B shows interactions between GFP:CP and free CP of CP-SP (3-7; upper) and CP-Po (lower) in leaves of $N.$ benthamiana agroinfiltrated with the appropriate pGDG:CP (GFP:CP) and either 1× or 2×pGD:CP (free CP) constructs. Left panel, GFP:CP with 1× free CP; Center panel, GFP:CP with 2× free CP; Right panel, GFP:CP with 2× free CP after plasmolysis. Note that AltMV-SP GFP:CP formed larger aggregates in the presence of 2× free CP as a result of strong CP self-interaction, whereas AltMV-Po GFP:CP did not form larger aggregates at increased concentration of free CP. FIG. 7C shows western blots of extracts of leaves agroinfiltrated with mixtures of [pGDG:CP+1×pGD:CP] or [pGDG:CP+2×pGD:CP] (FIG. 7B) and developed with AltMV-specific antibody, demonstrating that the levels of $CP_{SP}$ and $CP_{Po}$ in the leaves shown in FIG. 7B were equivalent.

FIG. 8 depicts the substitution of aa from AltMV-Po CP into AltMV 3-7. FIG. 8A shows electron micrographs of leaf extracts of $N.$ benthamiana infected with AltMV-3-7 (left) and AltMV $3\text{-}7_{CP\text{-}Po}$ (right). Note that the particles of AltMV 3-7 are laterally aggregated, whereas those. of AltMV $3\text{-}7_{CP\text{-}Po}$ are not aggregated. FIG. 8B shows the four mutants, MN(13,14)ID, LA(76,77)IS, T(154)A, and [MN(13,14)ID+ LA(76,77)IS] that were produced. For example, two amino acids, M and N, at position s 13 and 14 of the AltMV 3-7 amino acid sequence (SEQ ID NO:81) were substituted with amino acids I and D from position 13 and 14 of AltMV-Po amino acid sequence (SEQ ID NO: 82). FIG. 8C shows the symptoms 30 dpi of mutants at 25° C.; note lack of necrosis and milder mosaic in MN(13,14)ID and in LA(76,77)IS. Bottom panel shows symptoms at 15° C.

FIG. 9A shows that RNA transcripts were inoculated to *N. benthamiana* and *Alternanthera dentata*. By 30 dpi, AltMV 3-7 induced severe symptoms in *N. benthamiana* and *Alternanthera dentata*. AltMV 3-7$_{Po-CP}$ produced mild symptoms at 25° C., without necrosis at 15° C. in *N. benthamiana*, and mild symptoms in *A. dentata*. FIG. 9B depicts the Q-RTPCR of 3-7 and 3-7$_{Po-CP}$ at 10 dpi in *N. benthamiana* at 15° C. and 25° C., normalized to actin. Results with the same letter are not statistically different (P=0.05). FIG. 9C shows the symptoms of 3-7 and 3-7$_{Po-CP}$ on Rx-18 transgenic *N. benthamiana* and of PVX on non-transgenic plants, at 25° C. (upper, at 10 dpi) and 15° C. (lower, at 20 dpi). PVX did not infect Rx-transgenic plants; AltMV-induced symptoms were typical of those on non-transgenic plants.

FIG. 10 depicts agroinfiltration used for comparing gene silencing suppressor function. FIG. 10A shows that for silencing suppression assays, pGD:smGFP was co-infiltrated with (Left panel) pGD:Coat, pGD:TGB2, pGD:TGB1$_{L(88)}$, and pGD:TGB1$_{P(88)}$; (Right panel) pGD (empty vector), pGD:TGB3, pGD:HC-Pro, and pGD:p19. FIG. 10B shows smGFP siRNA accumulation, Lanes: (1) smGFP alone, (2) smGFP+pGD:TGB1 (P88), (3) smGFP+pGD:TGB1 (L88), (4) smGFP+pGD:HC-Pro(SMV), (5) smGFP+pGD:p19 (TBSV). Note that expression of TGB1(L88) resulted in accumulation of small RNAs similar to HC-Pro.

FIG. 11 depicts the expression of AltMV TGB1$_{L88}$ and TGB1$_{P88}$. FIGS. 11A-D show the nuclear localization of GFP:TGB1 fusion proteins [(A) GFP:TGB1$_{P88}$, (B) GFP:TGB1$_{L88}$, (C) GFP:TGB1$_{P88}$ coinfiltrated with equal concentration of free TGB1$_{L88}$ (pGD:TGB1$_{L88}$), (D) GFP:TGB1$_{L88}$ coinfiltrated with equal concentration of free TGB1$_{P88}$ (pGD:TGB1$_{P88}$)] transiently expressed in *N. benthamiana* leaves via agroinfiltration, examined by laser scanning confocal microscopy. Top: DAPI and GFP overlay; Middle: DAPI alone; Bottom: GFP alone. Each image represents 20×20 µm. FIG. 11E shows that TGB1$_{P88}$ (TGB1 AltMV 3-1; SEQ ID NO:86) and TGB1$_{L88}$ (TGB1 AltMV 4-7; SEQ ID NO:84) were separately expressed in mild (3-1) and severe (4-7) AltMV infectious clones. FIG. 11F shows the symptoms observed in the uppermost expanded leaf of infected by AltMV 3-1 mild clone variants 30 dpi; note the increased severity induced by over-expression of TGB1$_{L88}$. FIG. 11G depicts the over-expression of TGB1$_{P88}$ and TGB1$_{L88}$ from AltMV severe clone 4-7 variants, AltMV 4-7 alone, and 4-7 over-expressing TGB1$_{L88}$ induced systemic necrosis and death prior to 30 dpi at 15° C. AltMV 4-7 over-expressing TGB1$_{P88}$ did not induce necrosis, and plants showed mosaic at 40 dpi.

FIG. 12 depicts the nuclear and cell wall localization of helicase domain mutants of TGB1 assayed for gene silencing suppression. FIG. 12 A shows the use of agroinfiltration to compare gene silencing suppressor function. pGD:smGFP was coinfiltrated into *N. benthamiana* leaves with either pGD (vector without insert), pGD:TGB1$_{L88G}$, pGD:TGB1$_{G31R}$, pGD:TGB1$_{GK33/34RR}$, pGD:TGB1$_{D81R}$, pGD:TGB1$_{Q101R}$, pGD:TGB1$_{L88}$, or pGD:TGB1$_{P88}$, and fluorescence captured using a digital camera. FIG. 12B shows yeast two-hybrid interactions between TGB1$_{L88}$ and TGB1 mutants, with TGB1$_{L88}$ as the binding domain partner for all assays; "+"=interaction, "−"=no interaction observed. FIG. 12C shows nuclear localization of TGB1 helicase mutants expressed via agroinfiltration. 1$^{st}$ Row: DAPI and GFP overlay; 2$^{nd}$ Row: DAPI; 3$^{rd}$ Row: GFP; 4$^{th}$ Row: Plasmolysis was performed using 0.7 M sucrose solution; the cell wall was stained with calcofluor blue. Each image represents 20×20 µm. FIG. 12D shows the Western blot of proteins from infiltrated leaves, separated on a 12% SDS-polyacrylamide gel and developed with GFP-specific antibody.

FIG. 15 depicts the expression of an antisense eGFP with and without bacteriophage T7 RNA polymerase. FIG. 15A depicts the amplification of eGFP from pGDG using primers incorporating the T7 promoter. For insertion in the antisense orientation relative to the 35S promoter (pGD:T7eGFP), eGFP was amplified with BamHI-T7 promoter forward and XhoI reverse primers; for insertion in sense orientation (pGD:PFGe7T) XhoI-17 promoter forward and BamHI reverse primers were used. FIG. 15B shows eGFP fluorescence in *N. benthamiana* leaves agroinfiltrated with pGD:T7eGFP and pGD:PFGe7T in presence or absence of T7 polymerase from pCAM:T7RNAP; pGD:p19 was included in all infiltrations in order to suppress RNA silencing. Epidermal cells were imaged by laser-scanning confocal microscopy (LCSM) at 2 dpi. pGD:T7eGFP was expressed throughout the epidermal layer either with or without pCAM:T7RNAP (left); no fluorescence was detected from pGD:PFGe7T in the absence of T7 RNA polymerase (middle), but was observed in 19 of 200 epidermal cells in the presence of T7 RNA polymerase (right). Bars=50 µm.

FIG. 16 depicts the construction of AltMV full-length clones for in vitro transcription and agroinfiltration. FIG. 16A shows that full-length clones of AltMV genomic RNA in TOPO were digested with Pst I and Xma I and inserted into pGD:T7ttr vector cut with Pst I and Xma I. Subsequently, an Xma I and Xba I fragment from AltMV in TOPO was cloned into the pGD:AltMV PstI-XmaI subclone cleaved with the same enzymes. There are 54 nonviral nt between the 35S promoter and the T7 promoter sequence. FIG. 16B depicts PCR with three separate forward primers, each paired with reverse primer AltMV-399, used to determine if any non-viral nucleotides remain in tissues systemically infected from pGD:AltMV by agroinfiltration; lanes 1-3, PCR with the primer sets indicated to the right, with primer locations indicated on the genome. Lanes pGDAltMV, vector DNA template; lanes AltMV cDNA, cDNA template from systemically infected leaves.

FIGS. 17 A-E show that AltMV eGFP was detected in flowers and seed of infected plants. FIGS. 17A-D show *N. benthamiana* and FIG. 17E, *Arabidopsis* plants infected with AltMV:eGFP and allowed to set seed. Stigmas and styles (A), petals (B), matured ovules (C), immature seeds (D) of *N.*

*benthamiana*, and immature seed pods (E) of *A. thaliana* were visualized by laser-scanning confocal microscopy. Bars=100 µm.

Figure 18A:
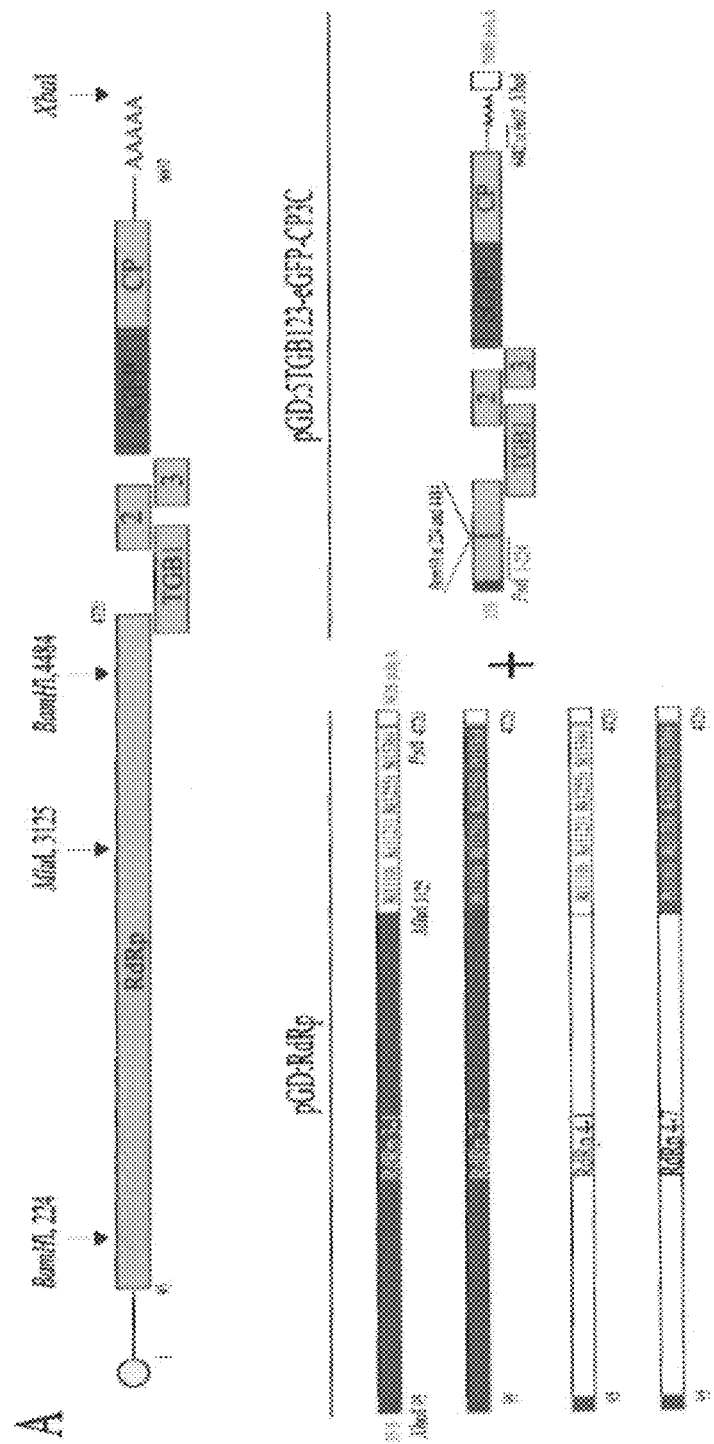

FIGS. 18 A-C depict the evaluation of replication of a defective AltMV genome in trans by RdRp expression from a pGD binary vector. FIG. 18A depicts the RdRp region amplified from each of the AltMV infectious clones 3-1, 3-7, 4-1, and 4-7 and inserted into pGD at the Xho I and Pst I sites between the 35S promoter and nopaline synthase termination region (NOS polyA) to form the respective pGD:RdRp construct. 5TGB123-eGFP-CP3C containing the AltMV 5' and 3' non-coding regions was separately cloned into pGD between the 35S promoter and NOS polyA. FIG. 18B shows that equal concentrations of each pGD:RdRp construct and pGD: 5TGB123-eGFP-CP3C were infiltrated to *N. benthamiana* leaves; (lower) a western blot of leaf extracts of: lane 1) pGD:RdRP 3-7; lane 2) pGD:5TGB123-eGFP-CP3C; and lane 3) [pGD:RdRp 3-7+pGD:5TGB123-eGFP-CP3C] developed with AltMV-specific antiserum. FIG. 18C shows laser-scanning confocal microscopy images of epidermal cells were captured using equal laser power at 3 days post infiltration. Intensity of eGFP expression reflects the efficiency of replication of the defective AltMV genome by the different RdRp constructs. Bar=100 µm.

FIGS. 19 A-D depict constructs of bipartite AltMV. FIG. 19A depicts the RdRp construct. The 3' non-coding region of AltMV from 6482 to 6607 was amplified using primers including SpeI (forward) XbaI (reverse) sites and inserted to Spe I/Xba I digested pGD:T7ttr. The T7 promoter, AltMV 3-7 5' non-coding and RdRp region was amplified using primers including Pst I (forward) and Spe I (reverse) sites, and inserted into the Pst I and Spe I digested vector containing the 3' non-coding region, creating pGD:5RdRp3; (a) RdRp-Rec-F denotes the site of the forward primer used for amplification of the region in which recombination occurs. FIG. 19B depicts the T7 promoter and AltMV 5' non-coding region (1 to 95) amplified with XhoI I (forward) and Bam HI (reverse) primers and cloned into pGD at these sites, followed by insertion of a Bam HI (from 4704) to Xba I PCR-generated fragment including the triple gene block, CP, and 3' non-coding region to create pGD:5TGB123-CP3A. FIG. 19C shows that AltMV nt 4484 (including a part of the RdRp region) to 3' non-coding region was ligated to the T7 promoter/AltMV nt 1-95 clone to produce pGD:5TGB123-CP3B. FIG. 19D shows full-length clone pGD:AltMV 3-7 was digested with Bam HI and religated, removing the region between nt224-4484 but maintaining the reading frame of the deleted RdRp, forming pGD:5TGB123-CP3C; "(b) TGB1-Rec-R" denotes the of the reverse primer used for amplification of the region in which recombination occurs.

FIGS. 20 A-C depict the detection by RT-PCR of recombination in plants infected with bipartite AltMV constructs. FIG. 20A. Arrowheads indicate the positions of primers (1) in the 5' non-coding region (NCR) and (2) at the 3' NCR/polyA tail of the 6607 nt AltMV genome. AltMV cDNA was synthesized using oligo(dT). FIG. 20B. Bipartite pGD:5RdRp3 and pGD:5TGB123-CP3C each include the 5'NCR and 3'NCR/polyA tail. Primers (1) and (2) are as in panel A. FIG. 20C: PCR using primers (1)+(2), 1% agarose gel. Lane 1, PCR product from control (uninfected) leaf; lane 2, PCR product from wild-type AltMV-infected plant; lane 3, PCR product from bipartite-infected leaf; lane 4, DNA marker ladder.

Figure 21A:
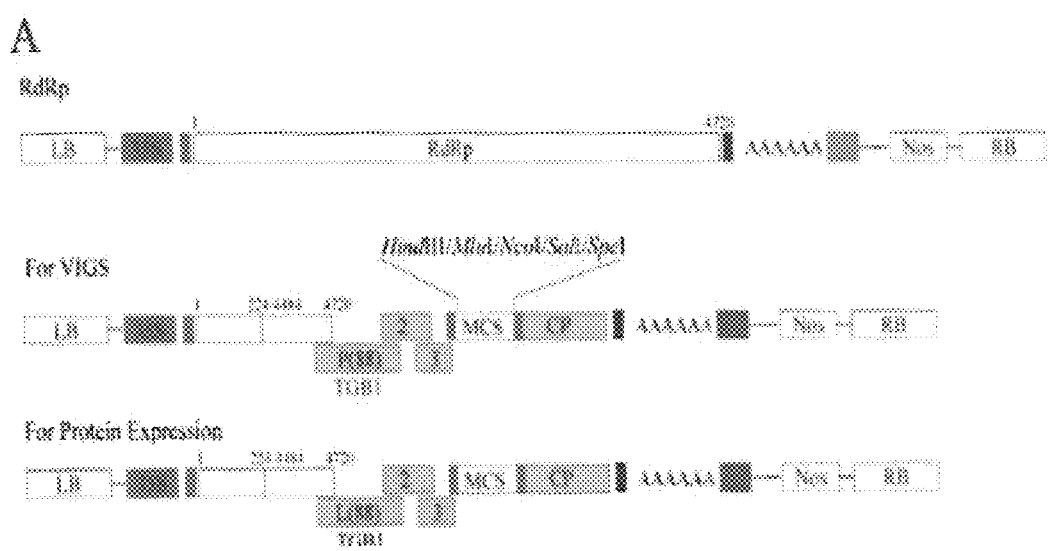
Figure 21B:
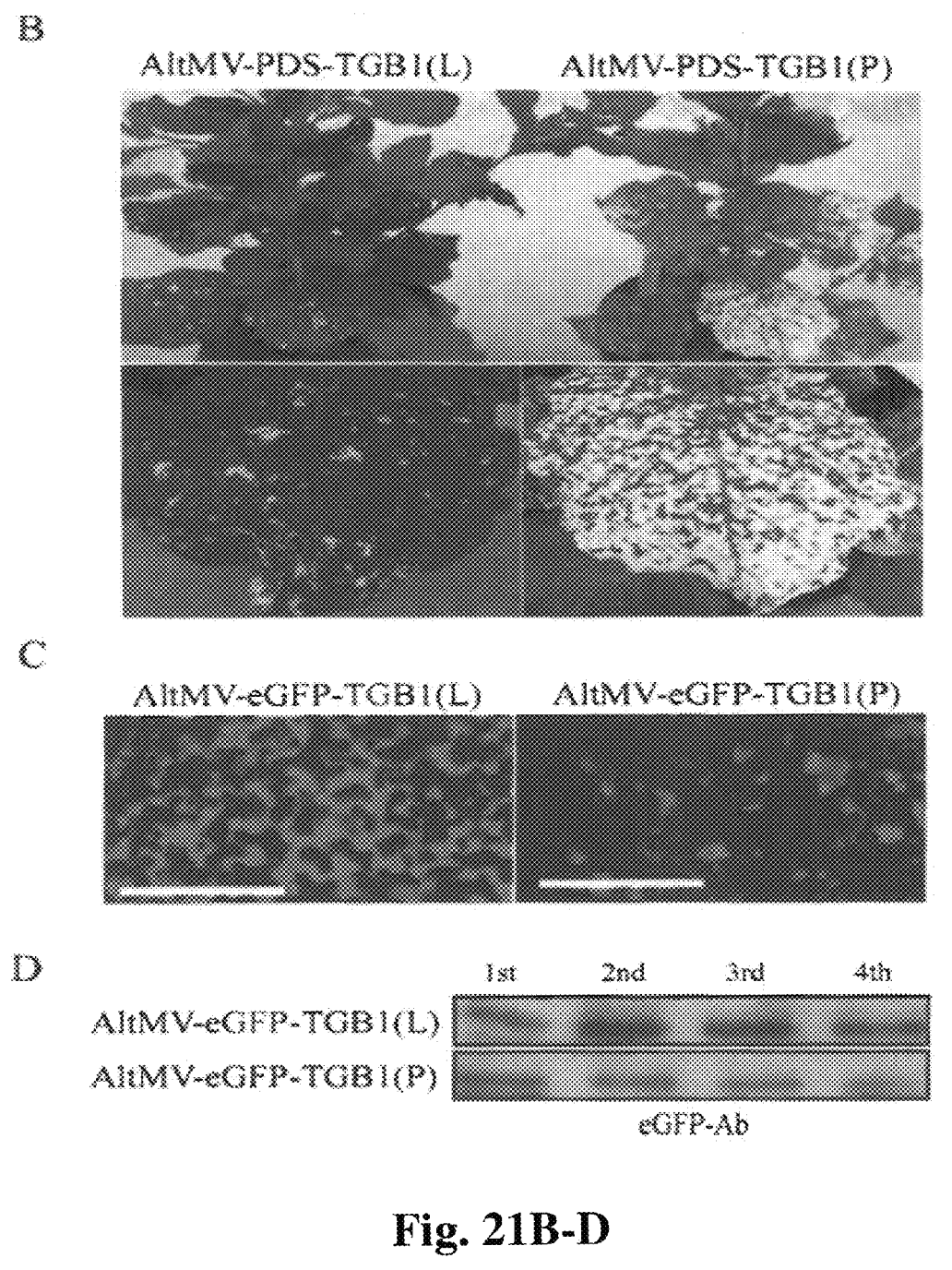

FIGS. 21A-D depict VIGS and protein expression in bipartite vector constructs. FIG. 21A shows pGD:5RdRp3 paired with derivatives of pGD:5TGB123-CP3C modified with a new MCS. For VIGS, pGD:5TGB1(P)23-MCS-CP3C has the TGB1$_{P88}$ from AltMV 3-1; for protein expression pGD: 5TGB1(L)23-MCS-CP3C has TGB1$_{L88}$ from AltMV 3-7 (as in pGD:5TGB123-CP3C). FIG. 21B: a 323 nt PDS fragment was inserted into the MCS sites of both TGB1$_{P88}$ and TGB1$_{L88}$ constructs. Each combination of pGD:5RdRp3 and pGD:TGB1(L)23-PDS-CP3C (left) or pGD:TGB1(P)23-PDS-CP3C (right) was inoculated to separate groups of *N. benthamiana* by agroinfiltration. Leaves developed a bleached phenotype caused by PDS silencing, shown at 30 dpi. FIG. 21C shows PCR-amplified eGFP was similarly inserted to both TGB1$_{P88}$ and TGB1$_{L88}$ constructs and agroinoculated to *N. benthamiana*. At 30 dpi, the youngest expanded leaf was examined by confocal microscopy. FIG. 21D is a Western blot of successive leaves from plants inoculated with TGB1$_{L88}$ (upper) and TGB1$_{P88}$ (lower) constructs expressing eGFP, developed with anti-eGFP antibody.

FIG. 22A depicts an alignment of the amino acid sequences of the TGB1 of PVX (upper; SEQ ID NO:68) and AftMV TGB1$_{P88}$ (lower; SEQ ID NO:69). The motifs I, IA, II, III, IV, V, and VI of PVX TGB1 are shaded, and six invariant residues conserved in pfam01443 (Viral helicase 1) proteins are shown in bold underline font in the AltMV TGB1 sequence. AltMV residue P88 is shown in bold font and shaded. FIG. 22B shows the CLUSTALW alignment of TGB1 amino acid sequences of AltMV isolates [AltMV 3-1 (SEQ ID NO:73); AltMV 3-7 (SEQ ID NO:74); AltMV-PA (SEQ ID NO:75); AltMV-RU (SEQ ID NO:76)] and of Tulip virus X (TVX; SEQ ID NO:70), Plantago asiatica mosaic virus Nandina mosaic virus isolate (PlAMV-NMV; SEQ ID NO:71), Zygocactus virus X (ZVX$_I$ SEQ ID NO:72), Papaya mosaic virus (PapMV; SEQ ID NO:77), Clover yellow mosaic virus (CIYMV; SEQ ID NO:78), PVX; SEQ ID NO:79, and White clover mosaic virus (WCIMV; SEQ ID NO:80). The position of AltMV TGB1 residue P88 is in bold text- and highlighted, and similarly positioned Leu or Ile residues in other sequences are underlined. The Leu residues of NMV and PVX TGB1 that were mutated to Pro are also highlighted. Key—*=conserved residues, :=conservation of strong groups, and .=conservation of weak groups.

Figure 23A:
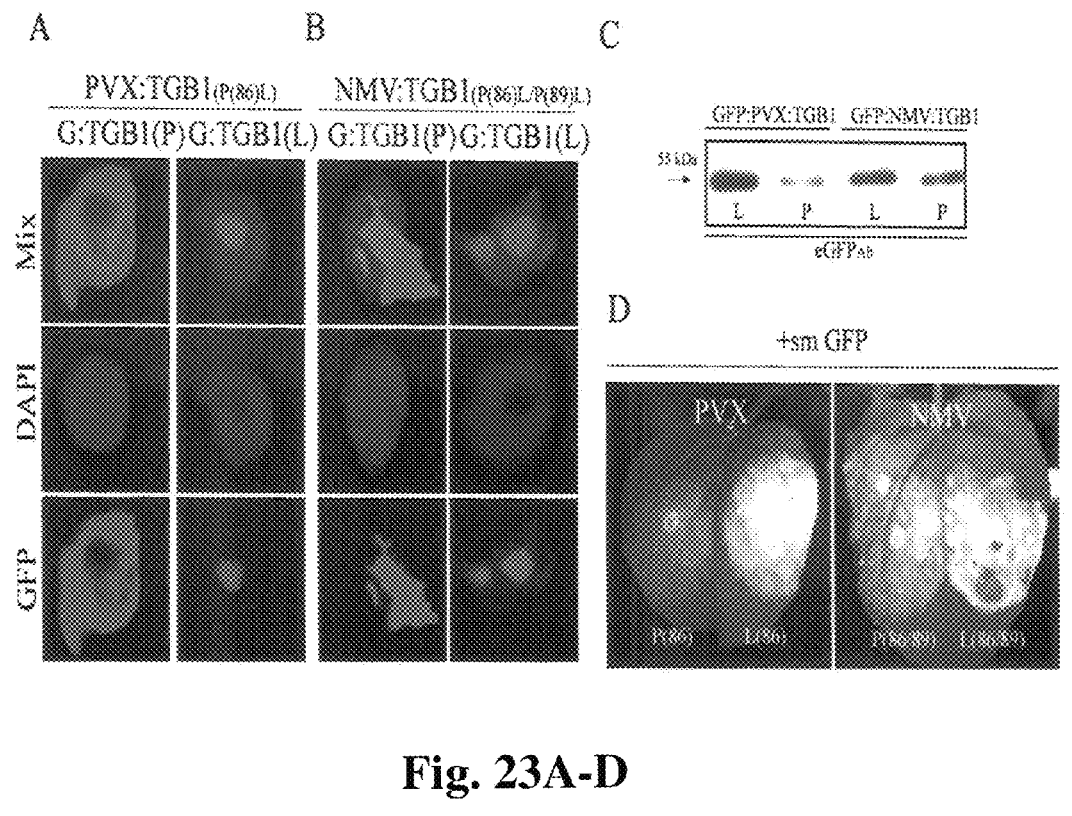
Figure 23E:
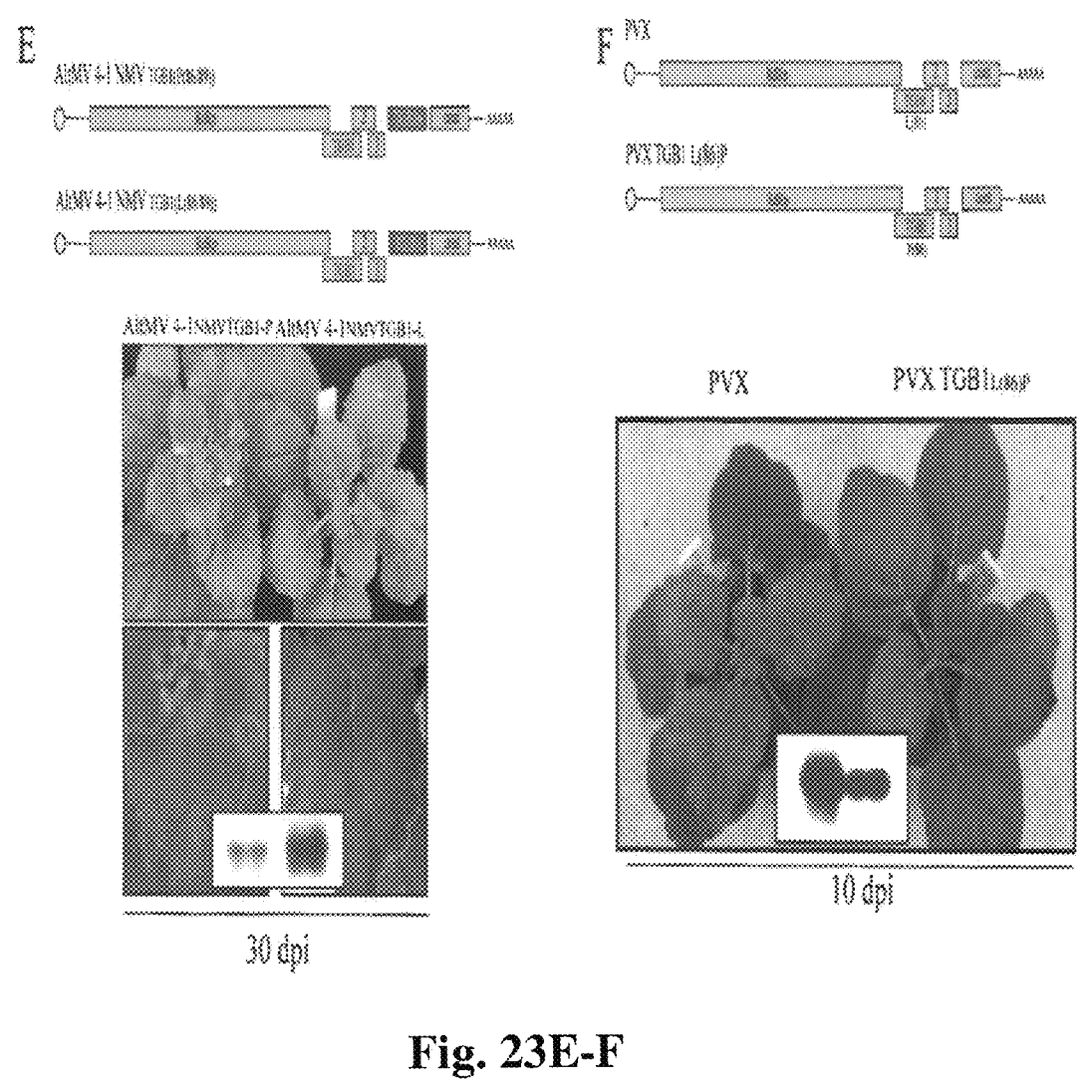

FIGS. 23 A-F depict the effects of Leu to Pro substitution in the TGB1 of PVX and NMV. FIGS. 23 A and B show a comparison of nuclear localization of PVX (A, left) and NMV (B, right) TGB1 variants expressed in *N. benthamiana* leaf via, agroinfiltration. Top: DAPI and GFP overlay; Middle: DAPI; Bottom: GFP. FIG. 23A: PVX: pGDG:PVX: TGB1$_{P86}$ (left), pGDG:PVX:TGB1$_{L86}$ (right); FIG. 23B: NMV: pGDG:NMV:TGB1$_{P86,89}$ (left), pGDG:NMV: TGB1$_{L86,89}$ (right). FIG. 23C is a Western blot of proteins from infiltrated leaves, separated on a 12% SDS-polyacrylamide gel, developed with eGFP-specific antibody; the arrow indicates the position of GFP:TGB1 variants. FIG. 23D depicts agroinfiltration used to compare gene silencing suppressor function. pGDsmGFP was coinfiltrated with pGD: PVX:TGB1$_{P86}$ and pGD:PVX:TGB1$_{L86}$ (left panel); and with pGD:NMV:TGB1$_{P86,89}$ and pGD:NMV:TGB1$_{L86,89}$ (right panel). FIG. 23E shows NMV:TGB1$_{L86,89}$ and NMV: TGB1$_{P86,89}$ overexpressed in AltMV mild clone 4-1, and agroinoculated to *N. benthamiana* (lower). At 30 dpi, symptoms were visible only in plants infected by the NMV: TGB1$_{L86,89}$-expressing clone (right). (The NMV: TGB1$_{P85,89}$-expressing clone is on the left.) The inset shows a Western blot of extracts from upper leaves developed with anti-AltMV-CP showing that both viruses did cause systemic infection. FIG. 23 F: The PVX TGB1$_{P86}$ was substituted into an infectious PVX clone, and RNA transcripts were inoculated to *N. benthamiana*. At 10 dpi, plants infected with the wild type (TGB1$_{L86}$)PVX clone developed severe symptoms (left) whereas PVX containing TGB1$_{P86}$ did not induce visible symptoms (right). The inset shows a Western blot of extracts of upper leaves developed with PVX-specific antibody, showing that both PVX variants established systemic infections.

DETAILED DESCRIPTION OF THE INVENTION

This invention concerns the creation of multiple, biologically distinct, infectious clones derived from AltMV-SP, from which we had previously obtained a partial sequence (Hammond et al., 2006b, supra), and the use of these clones and chimeric derivatives to identify some of the determinants contributing to symptom expression and replication efficiency of AltMV. These infectious clones were then developed into a viral vector system of considerable flexibility, with variants optimized for high level protein expression, or optimized for induction of Virus-Induced Gene Silencing (VIGS). The vector system was modified such that the initial full length vector constructs were suitable for delivery by either agroinfiltration (based on the CaMV 35S promoter) or in vitro RNA transcripts (based on the T7 promoter) from the same plasmid. Co-agro-infiltration of the bipartite constructs with constructs carrying the T7 RNA polymerase and the Tomato bushy stunt virus (TBSV) p19 genes significantly enhanced infection, and reduced the time to symptom expression. A further modification was to create a bipartite vector delivery system, separating the replicase (RdRp) from the movement and encapsidation functions (Triple Gene Block, TGB; and CP), allowing easier insertion of a Gene of Interest, and the potential for high throughput cloning. Co-agro-infiltration of the bipartite constructs with constructs carrying the T7 RNA polymerase and the TBSV p19 genes resulted in high efficiency of infection resulting from precise recombination of the bipartite transcripts in planta to regenerate a full length AltMV genome. While in vitro T7 transcripts, and agroinfiltration of constructs driven by the CaMV 35S or other promoters have commonly been used to initiate infections from cloned plant viruses, we are not aware of any previous utilization of transient in vivo transcription from the T7RNAP in planta; in most applications the T7 polymerase is supplied from a stably transformed chromosomal location.

The RdRp P01 domain, TGB1, and CP were all shown to contribute to symptom expression, and both the P01 domain and TGB1 appear to significantly affect replication efficiency. Unlike some other potexviruses, AltMV was not found to uniformly induce hypersensitive response; however, hypersensitive response was observed primarily at low temperature with variants that replicate with high efficiency, and correlated with particular amino acid residues. In contrast to the on-going emergence of variation and subsequent selection reported in some other systems, we report the stable co-existence of two dominant sequence types within isolate AltMV-SP over a period of several years and multiple passages in *Nicotiana benthamiana* following the original isolation from *Phlox stolonifera*. We relate this to modulation of both replication and symptoms when both sequence variants are present, and avoidance of hypersensitive response (Lim et al. 2010. *J. Gen Virol* 91: 277-287).

Figure 1A:
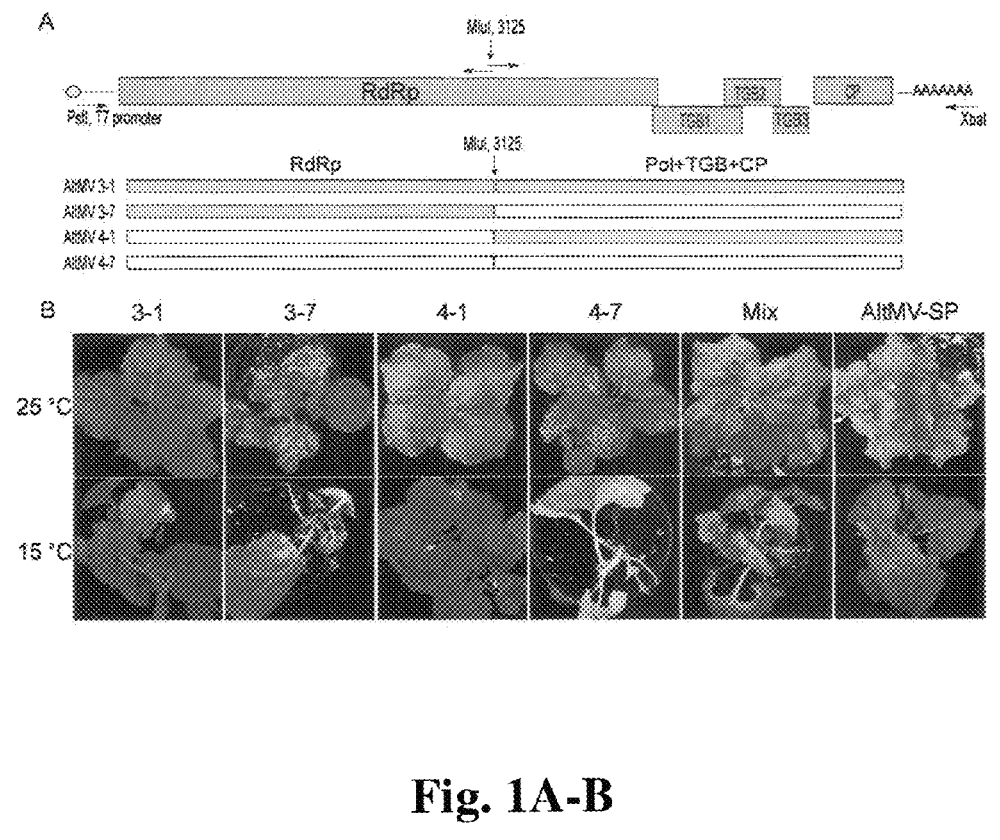

We have created four infectious clones from AltMV-SP (FIG. 1A), each of which demonstrates a distinct biological activity distinguished from that of the original AltMV-SP, and ranging from almost symptomless (AltMV 4-1) to more severe than AltMV-SP (AltMV 3-7). A mixture of all four clones resulted in symptoms similar to the parental isolate AltMV-SP (FIG. 1B). Symptom expression of all clones and combinations was more severe at 15° C. than at 25° C. (FIG. 1B). It is noteworthy that the four infectious clones were derived from all possible pairings of two clones representing each of the 5' and 3' portions of the AltMV genome, combined at a common MluI site from a population cloning experiment (Yu and Wong. 1998. *Arch. Virol.* 143:1617-1620) in which 28 potentially distinct full-length clones were obtained. In contrast, Yu and Wong observed that approximately 50% of full-length clones of Cymbidium mosaic virus (CymMV)—another potexvirus—obtained by a similar population cloning strategy were infectious.

Figure 2:
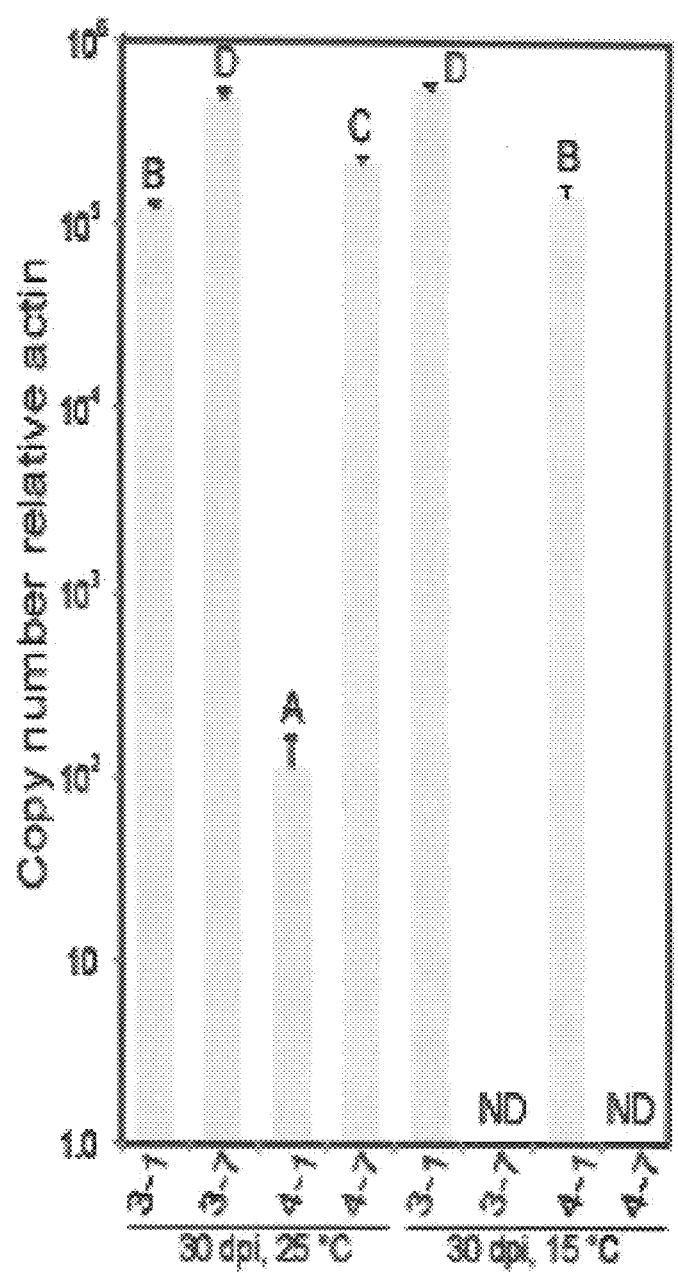
FIG. 2 shows the results of Q-RTPCR with CP-specific primers. Relative RNA accumulation of 3-1, 3-7, 4-1, and 4-7 was normalized to actin. The average value and standard deviation at 30 dpi is shown from four $N.$ benthamiana per clone at 25° C. (left) and 15° C. (right). RNA accumulation was significantly higher at 15° C. than at 25° C.; 3-7 and 4-7 killed plants prior to 30 dpi at 15° C. Values indicated by the same letter were not significantly different (LSD (P=0.05)= $6.6 \times 10^4$). RdRp primers yielded equivalent results (not shown).

There were significant differences in the level of replication of the four infectious AltMV clones at 25° C., with 3-7>4-7>3-1>4-1, whether measured by QPCR of the CP or RdRp (FIG. 2, Table 1). Efficiency of replication strongly correlated with symptom severity, It is clear that 5' [RdRp(-Pol)] clone 3 contributes to a higher rate of replication than clone 4[RdRp(-Pol)], and that 3' [Pol+TGB1/2/3+CP] clone 7 results in more efficient replication than clone 1 (FIG. 2, Table 1). There are 240 nt differences between [RdRp(-Pol)] clones 3 and 4, of which 3 nt changes are in the 5' UTR, and 237 are distributed throughout the RdRp coding region, resulting in 45 amino acid (aa) differences (Table 2). Because of the large number of changes distributed throughout this region, we did not attempt to dissect out the contribution of individual residues. There were far fewer differences between 3' [Pol+TGB1/2/3+CP] clones 1 and 7, with a total of only 21 nt (including one in the intergenic region, and one in the 3' UTR) resulting in only 5 aa differences, of which four were in the Pol domain, and one in TGB1 (Table 2).

TABLE 1

Replication of AltMV infectious clones;
copy number at 30 dpi relative to actin.

| Temperature | AltMV 3-1 | AltMV 3-7 | AltMV 4-1 | AltMV 4-7 |
|---|---|---|---|---|
| 25° C. | 122,245 b | 499,928 d | 117 a | 222,516 c |
| 15° C. | 563,529 d | ND* | 151,706 b | ND |

*ND = Not determined; plants died. Values followed by the same letter are not significantly different (P = 0.05); LSD (0.05) = 66,310

TABLE 2

Differences in sequence between the infectious clones.
Sequence Differences

| 5' [RdRp] clones 3, 4 | | 3' [Pol + TGB1/2/3 + CP] clones 1, 7 | | |
|---|---|---|---|---|
| Region | nt | aa | Region | nt | aa |
| 5' UTR | 3 | | Pol | 8 | 4 |
| RdRp | 237 | 45 | TGB1 | 6 | 1 |
| | | | TGB2 | 0 | 0 |
| | | | TGB3 | 1 | 0 |
| | | | Intergenic | 1 | — |
| | | | CP | 4 | 0 |
| | | | 3' UTR | 1 | — |
| Total | 240 | 45 | Total | 21 | 5 |

In order to determine which sequences might be present in the original isolate AltMV-SP, we amplified the region across the MluI site from an AltMV-SP infection initiated from frozen tissue, that had been stored about three years and multiple passages in *N. benthamiana* prior to the creation of the infectious clones. The amplified fragment included nucleotide positions that differ between the two clones of each region making up the infectious clones. The two dominant sequences recovered from this experiment corresponded to AltMV 4-7 (SEQ ID NO:1; severe) and AltMV 3-1 (SEQ ID NO:2; mild), in an 11:2 ratio. Two additional sequence types were recovered, sharing a A residue upstream of the MluI site where each of the infectious clones has a G, and a T residue where the infectious clones have either T or C; at a position downstream of the Mlu I site, one of these additional sequences has an A, and the other a G, residues that also differentiate 3' clones 1 and 7 (FIG. 3A). Neither the most severe (AltMV 3-7, SEQ ID NO:3) nor mildest (AltMV 4-1, SEQ ID NO:4) sequences were represented among the clones sequenced. It was thus apparent that sequences represented by clones 4-7 and 3-1 predominated in the original AltMV-SP, and that these may be regarded as representing two quasispecies clouds that coexisted through multiple passages in N. benthamiana, as has previously been reported for TMV and CMV (Schneider and Roossinck, 2001, supra).

To further examine the stability of co-infection of 4-7 and 3-1, and to examine the effects of temperature on virus replication, each isolate was inoculated singly, or in mixed infection, in parallel with original isolate AltMV-SP. Groups of plants were grown at 25° C., and separately at 15° C. Co-inoculation of 4-7 and 3-1 produced symptoms indistinguishable from AltMV-SP. Q-RTPCR showed that RNA accumulation of [3-1+4-7] was indistinguishable from 3-1 alone or from AltMV-SP at either 15° C. or 25° C.; accumulation of 4-7 alone was significantly higher. In each case accumulation was >4-fold higher at 15° C. than at 25° C. (FIG. 3B). Plants infected with 4-7 at 15° C. died before 30 dpi, while plants infected with AltMV-SP, 3-1, or [3-1+4-7] survived past 30 dpi with mosaic symptoms; at 10 dpi, accumulation of 4-7 RNA at 15° C. was >50% higher than for AltMV-SP, 3-1, or [3-1+4-7] (FIG. 3B). This demonstrated both that all isolates replicated to higher levels at the lower temperature, and that 3-1 interacted with 4-7 to modulate overall replication and symptoms.

The ability of AltMV 3-1 and 4-7 sequences to coexist was evaluated by labeling AltMV 3-1 with eGFP, and 4-7 with DsRed. When the two marked viruses were co-inoculated to N. benthamiana, approximately equal areas of GFP and DsRed expression were observed in the earliest systemically infected leaves, at 10 dpi. However, at 30 dpi, the uppermost infected leaves of plants grown at 25° C. showed approximately 10 times as large an area of DsRed as of GFP, with many co-infected cells (FIG. 4) showing both GFP and DsRed. Q-RTPCR using primers [specific for GFP and DsRed] demonstrated that AltMV 4-7 was present in approximately 10:1 excess over AltMV 3-1, as suggested by the relative areas of DsRed and GFP. In contrast, in plants grown at 15° C., approximately equal areas of GFP and DsRed were observed at both 10 and 30 dpi, and Q-RTPCR detected similar levels of each sequence.

Taken together, the ratios of the 4-7:3-1 in both the original AltMV-SP and mixed infections of the DsRed- and GFP-labeled clones, and the moderation of symptoms in the mixed infection compared to AltMV 4-7 alone, suggest that the mixed infection is maintained because the symptom amelioration is beneficial to survival of the host, and thus also to long-term propagation of the more severe sequence type represented by clone AltMV 4-7.

The influence of temperature on the ratio of 4-7[DsRed] to 3-1[eGFP] is interesting, and presumably results at least in part from the increased severity of all sequence types at lower temperature. Presumably at lower temperature there is less difference in the effects of the two sequence types on the host, and therefore AltMV 4-7 loses some of its competitive advantage.

It is noteworthy that the most severe symptoms observed were induced by AltMV 3-7, and the mildest symptom by 4-1, sequence combinations that were not detected among the PCR products from the central region of the original AltMV-SP genome (FIG. 3). While frequent recombination is observed between viruses of some viral taxa, including the potyviruses, not all recombinants are of equal fitness, and many recombinants may be eliminated from mixed populations. Recombination might also have occurred between distinct AltMV isolates, although the occurrence of recombination within potexviral species is not yet well documented. Malcuit et al. (2000. Virus Genes 20: 165-172) have suggested that PVX strain groups evolved through convergent evolution rather than recombination. Moles et al. (2007. Arch. Virol. 152:705-715) found no evidence for recombination in CymMV; however, Sherpa et al. (2007. J. Biosci. 32:663-669) and Vaughan et al. (2008. Arch. Virol. 153: 1186-1189) have identified putative recombinants of CymMV. Selection may disfavor recombined strains, as a result of incompatibilities between interacting viral proteins, or between viral proteins and cis-acting viral sequences (Malcuit et al., supra). Draghici and Varrelmann (2009, supra) have recently demonstrated recombination between defective transcripts of PVX under high selection pressure.

It has been observed previously in chimeric infectious clones of the potyvirus Potato virus A that one chimera induced a symptom phenotype distinct from either parental isolate, while a second would not infect potato systemically, suggesting that different parts of the genome function coordinately (Paalme et al. 2004. J. Gen. Virol. 85: 739-747). Although AltMV 3-7 and 4-1 are stable in single infections, it is possible that they are less fit in a mixed population. Indeed, in a mixed infection of 4-1:eGFP and 3-7:DsRed, 4-1:eGFP was barely detectable at 10 dpi, and not at all in upper leaves at 30 dpi (FIG. 4F). It is therefore unlikely that isolates as mild as AltMV 4-1 could be maintained in the population. Although neither severe sequence type AltMV 3-7 nor very mild derivative 4-1 were detected in the natural population of AltMV-SP, both may have specific applications as viral vectors.

The presence of two distinct sequence types (quasispecies clouds) in AltMV-SP could be explained either by co-infection, or by sequence divergence over many seasons in the phlox host, as phlox is a vegetatively propagated crop. Biological variants have been isolated from various citrus species infected with Citrus tristeza virus by either vectored transmission or host passage (e.g. Sentandreu et al., supra), and also from another potexvirus, PIAMV. Two biologically distinct sub-isolates (Li1 and Li6) were obtained from a lily isolate of PIAMV (Ozeki et al., supra); lily is also a vegetatively propagated crop. PIAMV sub-isolate Li1 caused a systemic hypersensitive response-like necrosis in N. benthamiana, whereas Li6 caused an asymptomatic infection; PIAMV RdRp amino acid (aa) 1154 was shown to contribute to the necrotic symptoms by substitution in infectious clones, although necrotic symptoms were not correlated with viral accumulation (Ozeki et al., supra). However, in contrast to the nine aa differences over the full genomes of Li1 and Li6 (seven in RdRp, one in TGB1, and one in TGB3; Ozeki et al., supra), AltMV 4-7 and AltMV 3-1 differ by 49 aa in RdRp, one in TGB1, and none in TGB2, TGB3, or CP. In further work, it was shown that PIAMV has high divergence within the RdRp, with seven Japanese isolates from lily and primrose sharing only 82-85% aa sequence identity with a Russian Plantago isolate and a US Nandina isolate (Komatsu of al. 2008. Arch. Virol. 153: 193-198); closer inspection shows that only 15 aa residues differ between the six Japanese lily isolates (all derived from a single plant), while 41 further positions differentiate the lily isolates from the primrose isolate, and a total of 303 aa positions differ when the RdRp sequences of all nine isolates are aligned (data not shown). The 49 aa differences between the RdRps of AltMV 3-1 and 4-7, derived from the same plant, show these isolates to be considerably more divergent that the PlAMV isolates obtained from a single lily plant.

It has previously been observed that a single amino acid in the polymerase domain of the RdRp of both PVX and PlAMV contributes to necrotic symptoms in *N. benthamiana* (Kagiwada et al., supra; Ozeki at al., supra). However, in both of these cases the levels of replication of necrotic and non-necrotic point mutants were similar, as measured by CP accumulation. In the case of AltMV, exchange of the Pol domain, with its three aa differences, is correlated with increased replication as well as necrosis; the increase in replication levels observed at 15° C. in all isolates is also correlated with necrosis (FIG. 5). Other instances of symptom severity associated with the RdRp and increased replication levels include the tobamoviruses TMV (Lewandowski and Dawson. 1993. *Mol. Plant—Microbe Interact.* 6: 157-160) and Pepper mild mottle virus (Hagiwara et al. 2002. *Arch. Virol.* 147:833-840), although in both of these tobamoviruses the associated residues were between the methyl transferase and helicase domains, rather than the Pol domain as in AltMV. Although an increased level of replication is a probable contributor towards the observed necrosis in AltMV 3-7, 4-7, and chimeric constructs 4-1$_{PRK}$ and 4-1$_{PRKL}$, it is also possible that the changes influence interactions with host cellular factors (Kagiwada et al., supra). The RdRp of CMV induces plant resistance responses in some hosts (Kim and Palukaitis. 1997. *EMBO J.* 16: 4060-4068; Karasawa et al. 1999. *Phytopathology* 89: 1186-1192), and the 126 kDa RdRp of TMV is the elicitor of the N gene in tobacco (Erickson et al. 1999. *Plant J.* 18: 67-75); however, the necrosis induced by AltMV, PVX, and PlAMV RdRps is a form of systemic hypersensitive response rather than resistance, and the necrosis induced by AltMV is due to increased replication rather than the AltMV RdRp acting as an elicitor (see below).

Substitution of TGB1, with a single amino acid change, also affected symptom expression. Whereas AltMV 4-1 was essentially symptomless, substitution of TGB1 [L(88)] in 4-1 L resulted in mosaic symptoms by 20 dpi, and substitution of both Pol and TGB1 (4-1PRKL) resulted in necrosis by 10 dpi with continued severe symptoms (FIG. 5B).

Figure 6A:
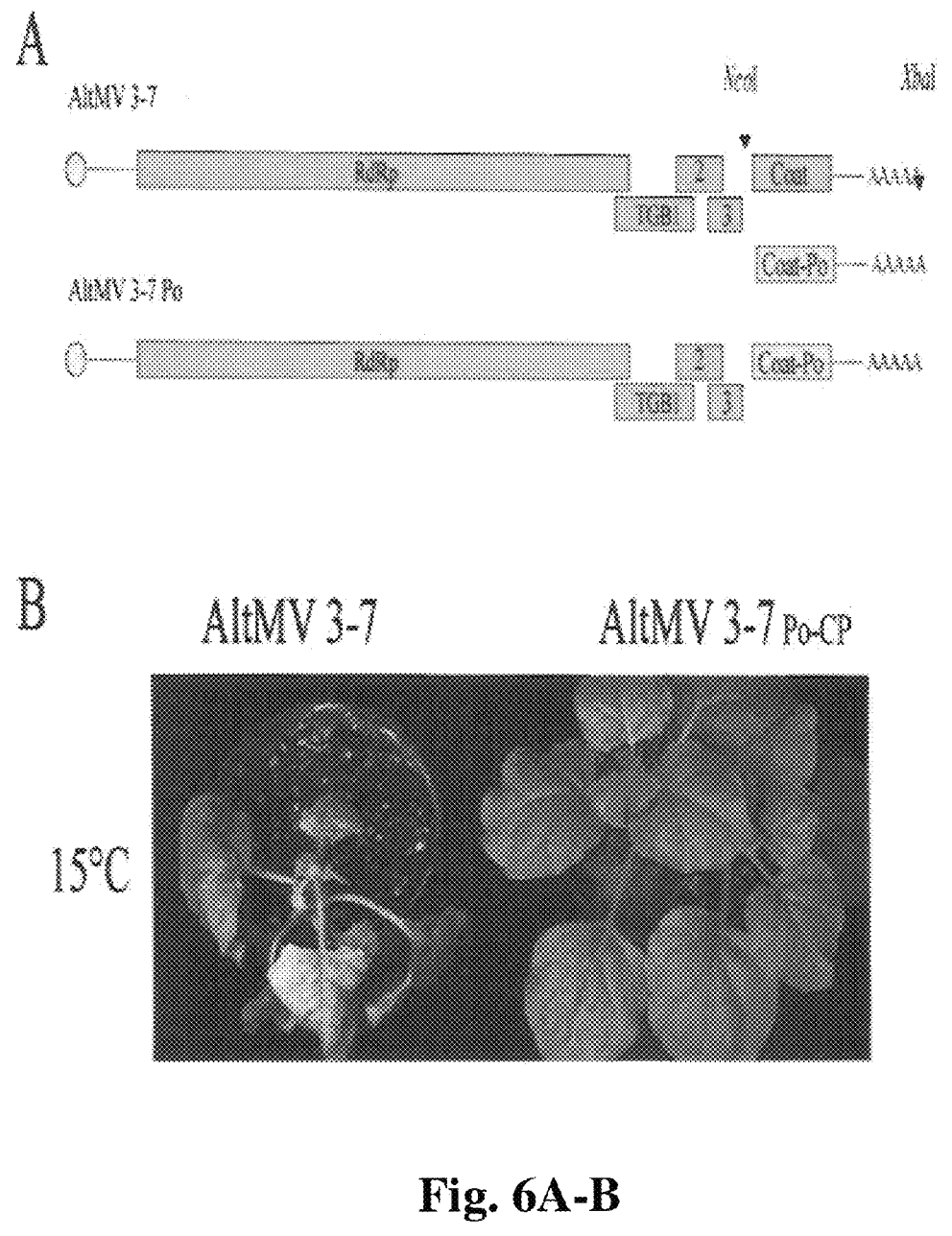

The CP gene of AltMV was identified as a third contributor to symptom expression, and the elicitor of necrosis, in four types of experiment. Although there were no differences between the CP genes of infectious clones 4-7 and 3-1, we had available clones of the 3' region of AltMV-Po, which differs in nine amino acid positions from AltMV-SP (Hammond of al., 2006a,b). Substitution of the AltMV-Po CP (SEQ ID NO:5) into AltMV 3-7 resulted in amelioration of symptom expression including a lack of necrosis, at both 25° C. and 15° C. (FIG. 6), although there was no significant effect on levels of replication. Yeast two hybrid experiments demonstrated a strong interaction between AltMV-SP (3-7) CP subunits, but only a much weaker interaction between AltMV-Po CP subunits (FIG. 7A). The weaker interaction between AltMV-Po CP subunits was confirmed in two additional ways. Co-agroinfiltration of *N. benthamiana* with a GFP:CP fusion together with free CP of AltMV-SP (3-7) resulted in aggregation of the GFP-CP fusion into punctate foci, whereas similar co-infiltration of GFP-CP$_{Po}$ and free CP$_{Po}$ did not result in the formation of punctate foci; the similar levels of GFP-CP fusions, and free CP of the two types was confirmed by western blotting (FIG. 7C). Additionally, electron microscopy of sap extracts of plants infected with AltMV 3-7 revealed a majority of particles in lateral association with other particles, whereas particles in extracts of plants infected with AltMV 3-7$_{Po-CP}$ were primarily not associated with other particles (FIG. 8A). Site-directed mutagenesis of AltMV 3-7 CP to create MN(13,14)ID resulted in loss of necrosis at both 25° C. and 15° C., whereas CP mutant LA(76, 77)IS did not ablate necrosis (FIG. 8B, C). CP mutations that affect subunit:subunit interactions, and thus particle stability as well as symptoms, have been well documented in TMV (e.g. Culver et al. 1994. *J. Mol. Biol.* 242: 130-138), and in other viruses such as Turnip crinkle virus (Heaton and Laakso. 1995. *J. Gen. Virol.* 76: 225-230). However, the N-terminal region of the AltMV CP is presumed to be on the particle exterior, and would not necessarily affect subunit interactions within the virion, though expected to be surface accessible for potential interactions with other viral or host proteins.

Figure 9A:
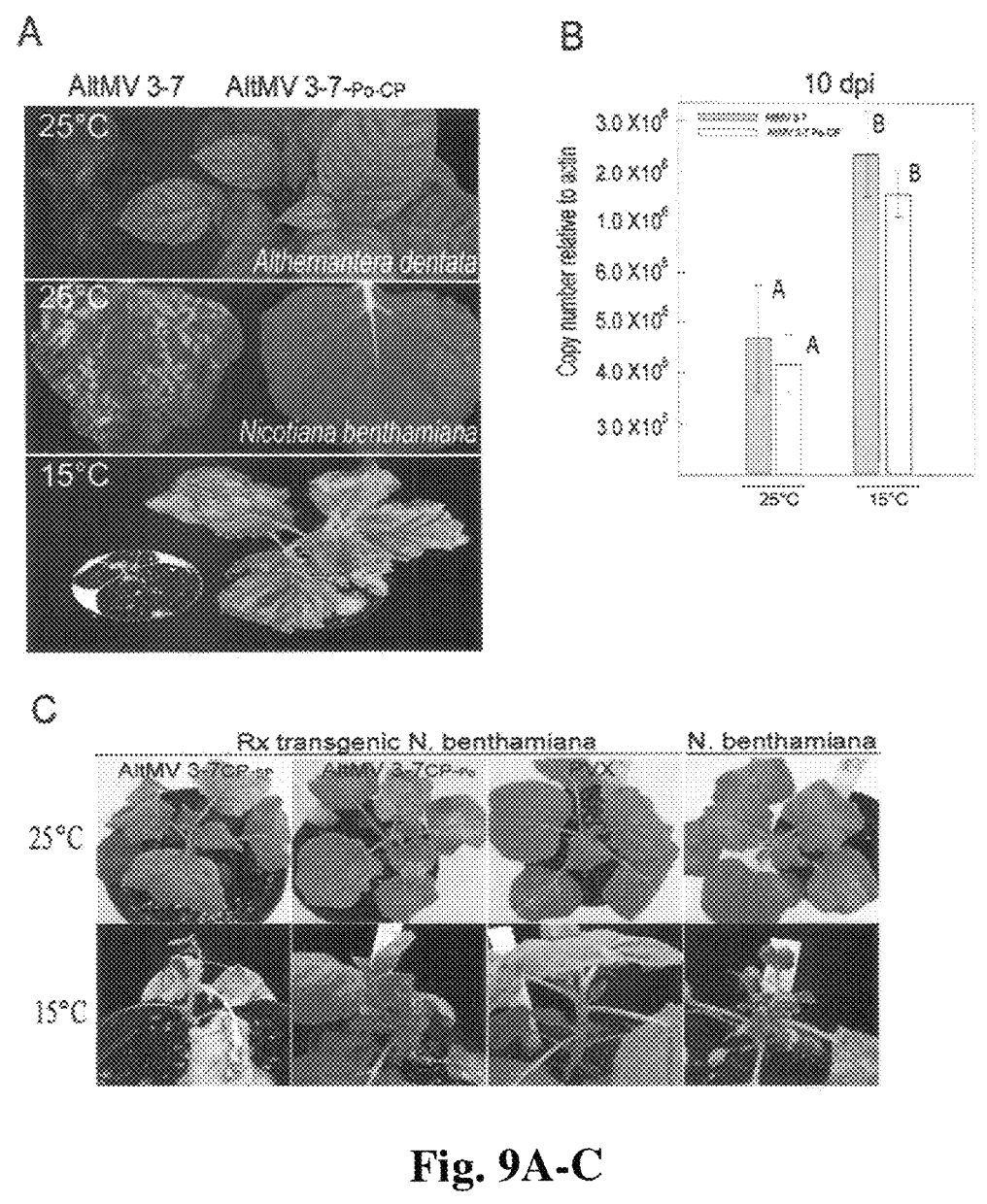

The PVX CP has been reported as a trigger of the hypersensitive reaction (Verchot-Lubicz et al., supra), and when expressed at high levels under control of the 35S promoter, induced hypersensitive response (Bendahmane et al., 2000. *Plant J.* 21: 73-81). Our results suggest that AltMV-SP CP is a determinant of necrosis and hypersensitive response at low temperature, and in the isolates that accumulate to the highest levels, also at 25° C. (FIG. 9A). In contrast, AltMV-Po CP did not induce necrosis even at 15° C., even though the level of replication of AltMV 3-7$_{Po,CP}$ was equivalent to that of 3-7 (FIG. 9B). It is thus apparent that CP subunit interactions— probably not involved directly in virion stabilization—are a major contributor to induction of necrosis. Residues 32-139 of PVX CP were shown to be essential for inducing Rx resistance (Bendahmane et al. 1995, supra), and interactions between PVX CP and Rx involve a conformational change in the Rx protein (Verchot-Lubicz et al., supra). In contrast, the residues of AltMV CP critical to the necrotic response are surface-located, and alignment of the AltMV CP with PVX CP shows a different sequence in the domain including the residues equivalent to PVX CP residues 32-139 (data not shown); and PVX residues K121 and R127, identified by Goulden et al. (1993. *Virology* 197:293-302) as key to the Rx interaction, are S94 and R100 in AltMV CP (conserved amongst all AltMV sequences available; see FIG. 2 of Hammond et al., 2006a, supra). As AltMV replicates and induces systemic symptoms in transgenic line Rx-18 (FIG. 9C), the AltMV CP is presumed not to interact with the Rx protein.

The effect of the [L(88)P] difference in TGB1 was further examined through co-agroinfiltration of each variant with smGFP in *N. benthamiana*, and comparison with AltMV TGB2, TGB3, and CP, as well as the well-characterized suppressors of RNA silencing HC-Pro and TBSV p19. The TGB1 from AltMV 3-7 (L88) shows obvious suppression of GFP silencing comparable to p19 and HC-Pro (FIG. 10A), and appears to act through a mechanism similar to HC-Pro, as siRNAs to GFP were detected with TGB1(L88) and HC-Pro, but not p19 (FIG. 10B). AltMV TGB1(P88). TGB2, TGB3, and CP did not display any obvious silencing suppression activity. The potexvirus TGB1 has been identified previously as a suppressor of RNA silencing, but it is unclear whether TGB1 blocks amplification of the 21 nt siRNAs or acts downstream of the host gene RDR6 in its action to protect the virus against host-directed RNA silencing (Verchot-Lubicz et al., supra). The similarity to the action of HC-Pro, and accumulation of siRNAs only where high-level replication occurs, suggests that AltMV TGB1 acts downstream of RDR6.

We have demonstrated that AltMV TGB1$_{L88}$ is an effective suppressor of RNA silencing, whereas TGB1$_{P88}$ has significantly weaker silencing suppression activity; we have also shown that $TGB1_{L88}$ and $TGB1_{P88}$ interact to interfere with silencing suppression (Lim et al., 2010 supra). In order to better understand these differences, we examined the subcellular localization of GFP:$TGB1_{L88}$ and GFP:$TGB1_{P88}$ following agroinfiltration of pGDG-$TGB1_{L88}$ and pGDG-$TGB1_{P88}$ constructs in N. benthamiana. Single expression of GFP:$TGB1_{L88}$ or GFP:$TGB1_{P88}$ differed in nuclear localization; GFP:$TGB1_{L88}$ was observed largely as discrete aggregates inside the nucleus (presumed to be the nucleolus), as demonstrated by reduced DAPI staining in the area of GFP accumulation (FIG. 11B). In contrast, GFP:$TGB1_{P88}$ accumulated in less ordered aggregates at the periphery of the nucleus (FIG. 11A). To examine interactions between $TGB1_{L88}$ and $TGB1_{P88}$, GFP:$TGB1_{P88}$ was co-expressed with free $TGB1_{L88}$ (pGD-$TGB1_{L88}$), and GFP:$TGB1_{L88}$ was co-expressed with free $TGB1_{P88}$ (pGD-$TGB1_{P88}$). The interaction of GFP:$TGB1_{P88}$ with free $TGB1_{L88}$ yielded aggregates at the periphery of the nucleus (FIG. 11C) as previously observed with GFP:$TGB1_{P88}$ alone (FIG. 11A). However, while co-expression of GFP:$TGB1_{L88}$ with free $TGB1_{P88}$ also resulted in accumulation of aggregates at the periphery of the nucleus (FIG. 11D), formation of the discrete intranuclear aggregates observed with GFP:$TGB1_{L88}$ alone (FIG. 11B) was inhibited.

Further evidence for the inhibition of RNA silencing suppression was obtained by over-expression of either $TGB1_{L88}$ or $TGB1_{P88}$ as added genes from AltMV infectious clone 4-7 (FIG. 11E), which normally produces severe symptoms and plant death by 30 dpi at 15° C. (Lim et al., 2010, supra). Over-expression of $TGB1_{L88}$ resulted in severe symptoms and systemic necrosis prior to 30 dpi, similar to AltMV 4-7, whereas over-expression of $TGB1_{P88}$ resulted in milder symptoms with plants surviving well past 40 dpi (FIG. 11G), similar to the amelioration of symptoms observed in mixed infections of severe clone 4-7 ($TGB1_{L88}$) and mild clone 3-1 ($TGB1_{P88}$) that is presumed to result from interaction of $TGB1_{L88}$ and $TGB1_{P88}$ (Lim et al., 2010 supra).

Figure 11F:
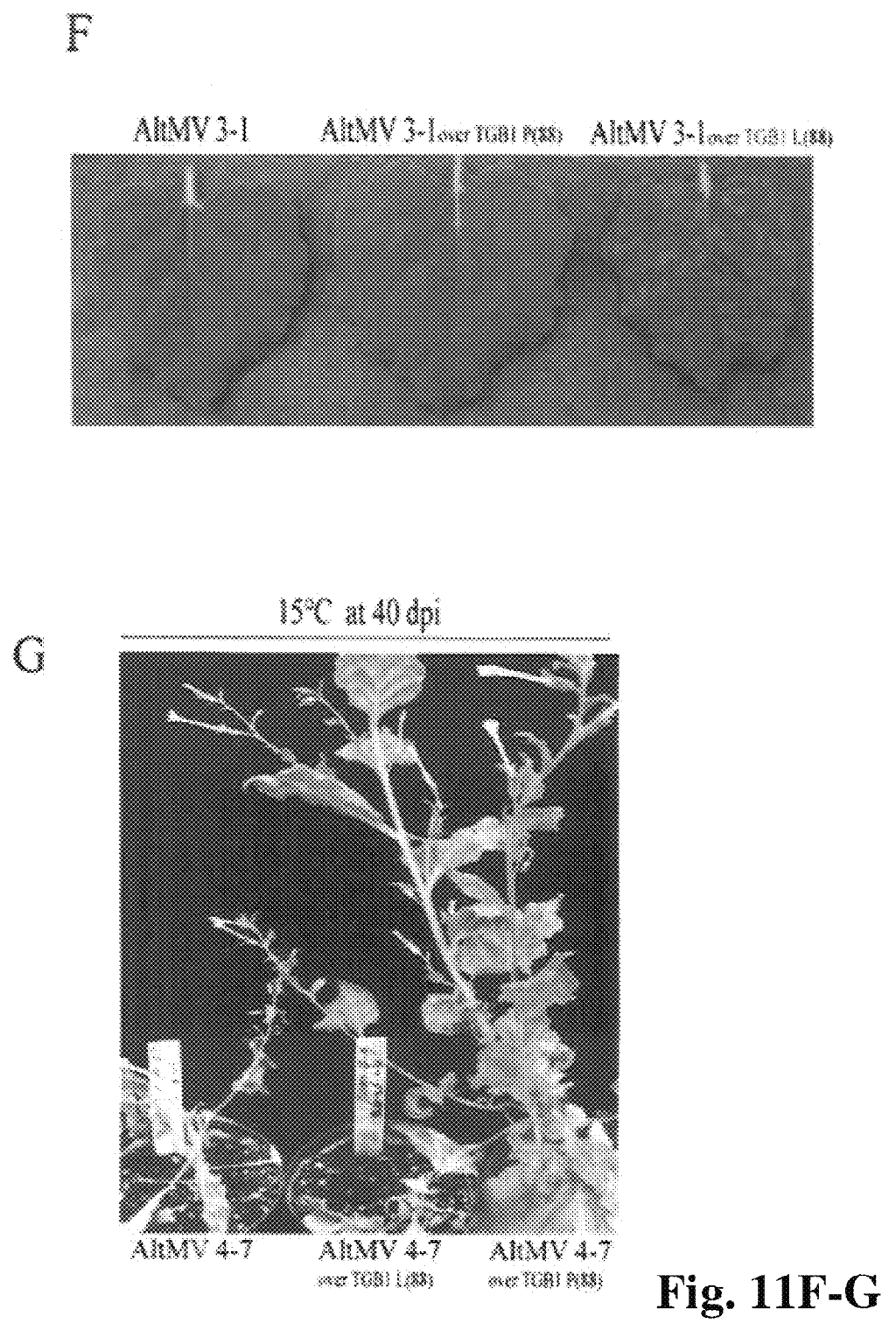

Mild infectious clone 3-1, which has $TGB1_{P88}$ in the genomic position, normally produces mild mosaic (Lim et al., 2010 supra). Over-expression of $TGB1_{P88}$ as an added gene (FIG. 11E) had no effect on symptom severity; in contrast, over-expression of $TGB1_{P88}$ from AltMV 3-1 resulted in a more prominent mosaic (FIG. 11F).

Multiple conserved motifs have been identified within the TGB1 proteins of potexviruses and hordeiviruses, and the C-terminal region of PVX TGB1 has been shown dispensable for ATPase activity (Morosov et al., 1999). Conserved domains I, IA, II, III, IV, V, and VI of AltMV TGB1 were compared with those of PVX (FIG. 22A and pfam01443 (Viral helicase1; NCBI, CDD). Six residues were observed to be absolutely conserved among AltMV and the 72 sequences representing the genera Alfamovirus, Bromovirus, Idaeovirus, Ilarvirus, Marafivirus, Tymovirus, Allexivirus, Carlavirus, Foveavirus, Potexvirus, Vitivirus, Tobamovirus, Tobravirus, Benyvirus, Hordeivirus, Pecluvirus, and Pomovirus (FIG. 22A, and data not shown). Arg substitution mutants were introduced separately at five of these residues in conserved motifs I (G31R and GK33/34RR), II (D81R), and III (Q101R); these helicase domain Arg mutants and an L(88)G mutant detected among a population of TGB1 PCR products from an AltMV-infected plant (in which all other cloned PCR products had L88) were tested for interaction with WT TGB1 in the yeast two-hybrid system (FIG. 12B), and for their efficacy in suppression of RNA silencing (FIG. 12A). Mutants in motifs I (G31R and GK33/34RR) lost both the ability to interact with WT TGB1 (FIG. 12B) and to efficiently suppress RNA silencing (FIG. 12A), whereas mutants in motifs II (D81R) and III (Q101R) retained both interaction with WT TGB1 (FIG. 12B) and silencing suppression activity (FIG. 12A). The natural mutant (L88G) retained interaction with WT TGB1 in the yeast two-hybrid system (FIG. 12B), but showed similar silencing suppression activity to the L88P variant present in mild clone AltMV 3-1 (FIG. 12A).

The subcellular localization of each TGB1 NTPase/helicase domain mutant was then examined by agroinfiltration of GFP:TGB1 fusions (pGDG-$TGB1_X$) to observe nuclear and cell wall localization. The GFP:$TGB1_{G88}$ mutant localized at the nuclear periphery and at the cell wall, where it was retained following plasmolysis (FIG. 12C). The motif I mutants (GFP:$TGB1_{R31}$ and GFP:$TGB1_{RR33/34}$) showed no distinctive localization pattern, with accumulation throughout the nucleus and without retention at the cell wall (FIG. 12C), similar to the behavior of free GFP, although western blotting with GFP antiserum revealed bands of the size expected for GFP:TGB1 (FIG. 12D). The motif II (GFP:$TGB1_{R81}$) and motif III (GFP:$TGB1_{R101}$) mutants differed from the WT TGB1 in nuclear localization, accumulating at the nuclear periphery and into the cytoplasm, as well as associated with an internal nuclear body presumed to be the nucleolus (FIG. 12C); however, these two mutants were retained at the cell wall after plasmolysis (FIG. 12C) as for WT (Lim et al. 2010, supra). Although we have not determined the effects of our site-directed mutants on viral movement, AltMV $TGB1_{D81R}$ and $TGB1_{Q101R}$ correspond to PVX mutants D82G and Q103R that fell into class B (active for silencing suppression but defective for cell-to-cell movement; Bayne et al., 2005). These results together suggest that self-interaction is required for TGB1 to accumulate in discrete aggregates within the nucleus and to localize at the cell wall, and that nuclear localization is necessary but not sufficient for strong suppression of RNA silencing.

Figure 13:
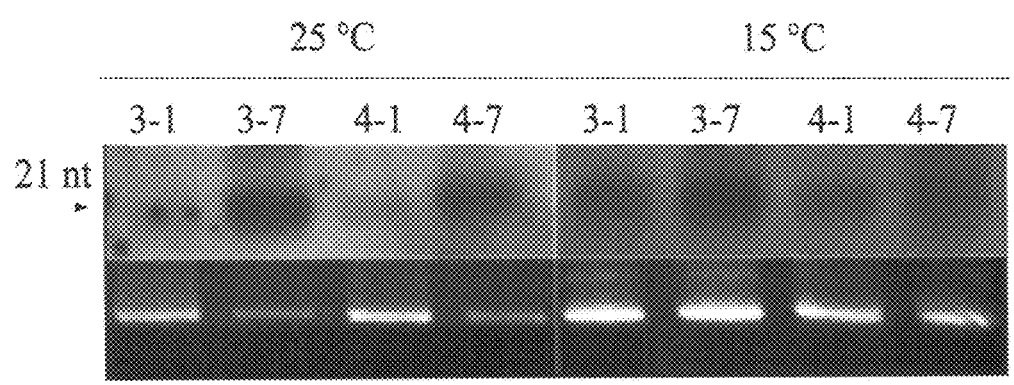
FIG. 13 shows AltMV-related small interfering RNAs (21-23 nt) detected in extracts of *Nicotiana benthamiana* infected with AltMV infectious clones 3-1, 3-7, 4-1, and 4-7 at either 25° C. (left) or 15° C. (right); the position of a 21 nt marker is indicated. The lower panel shows an ethidium bromide-stained image of the ribosomal RNA region of the gel as a loading control for the level of total RNA. At 25° C. little siRNA was detected in plants infected with mild AltMV clones 3-1 and 4-1 (TGB1$_{P88}$) compared to severe clones 3-7 and 4-7 (TGB1$_{L88}$), whereas at 15° C. higher levels of siRNA were detected in plants infected by all clones, with the most prominent increases in the levels of siRNAs with 3-1 and 4-1 reflecting a significantly increased level of replication at 15° C.
Figure 14:
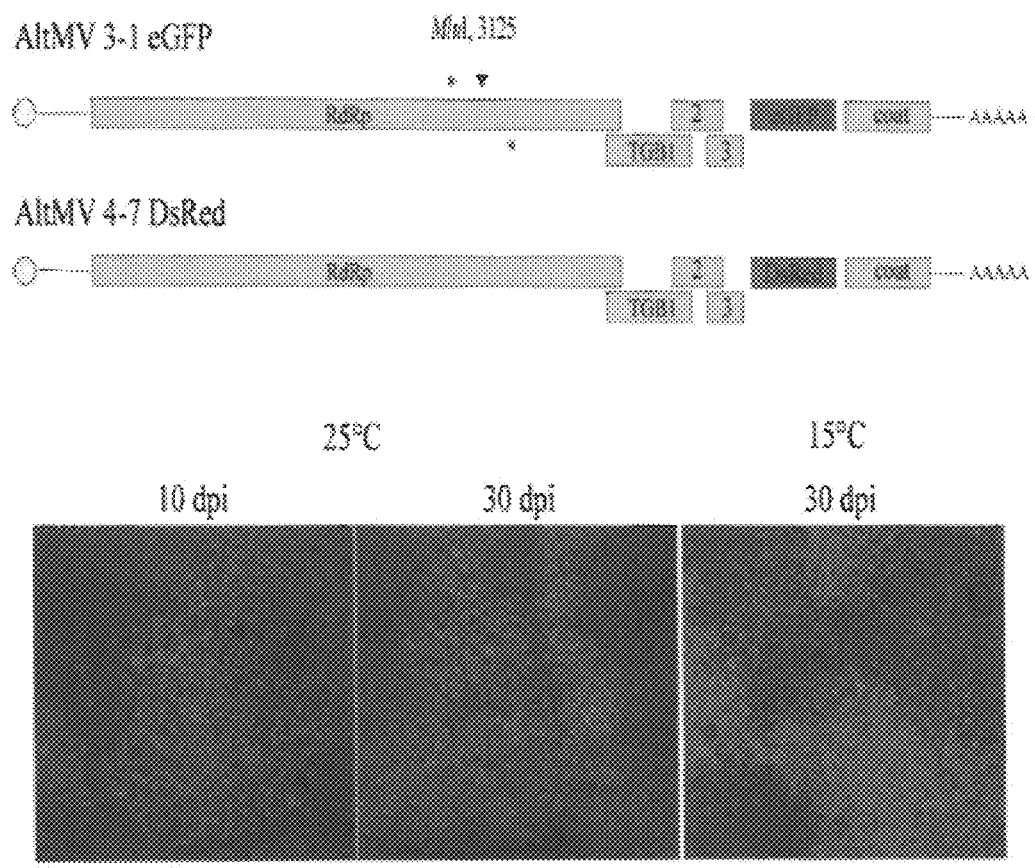
FIG. 14 shows "Mild" clone 3-1 labeled by insertion of eGFP and "Severe" clone 4-7 labeled with DsRed. The youngest expanded leaf was examined by confocal microscopy at 10 dpi and 30 dpi. Both sequences are maintained at 15° C. or 25° C. but appear to replicate mainly in separate areas of the leaf, with areas of co-infected cells.

Necrosis was observed in multiple combinations of CMV isolates and the satellite RNA D-CARNA 5 at 24° C., while necrosis was significantly reduced or absent with some strains, but increased with another at 32° C.; the necrosis was primarily dependent upon increased levels of viral replication (Kaper et al., supra). The effect of temperature on silencing suppressors and plant defense mechanisms has been noted previously (Chellappan et al. 2005. Plant Physiol. 138: 1828-1841; Qu et al. 2005. J. Virol. 79: 15209-15217; Jovel et al. 2007. J. Virol. 81: 12285-12297; Siddiqui et al. 2008. J. Gen. Virol. 89: 1502-1508). The increased symptom severity of all clones at 15° C. compared to 25° C. is presumably due to more effective suppression of RNA silencing (or reduced ability of the plant to activate silencing), as demonstrated by the very marked increase in replication of AltMV 4-1 at the lower temperature (FIG. 3), and the significantly increased levels of siRNAs detected for both AltMV 3-1 and 4-1 at this temperature (FIG. 13). Similarly, in the case of mixed infections of AltMV 3-1:eGFP and 4-7:DsRed, there was a significant difference in the relative areas of tissue affected at 25° C., but little difference at 15° C. (FIG. 14). This presumably reflects the increased ability of 3-1 to replicate at lower temperature, whereas 4-7 was less affected by the temperature differential, as seen by the relative levels of siRNAs (FIG. 13).

Cumulatively, these results suggest that necrotic symptom expression of AltMV is strongly influenced by three viral gene products, the RdRp, TGB1, and CP, with CP acting as the elicitor of necrosis. Although we were able to demonstrate significant differences due to the Pol domain of the RdRp, it is clear that the 45 aa differences in the upstream region (differences between 5' RdRp clones 3 and 4) also exert a significant effect, as clones 3-7 and 3-1 each replicated to a higher level than the equivalent clones with the clone 4 RdRp domain. It is clear that both the Pol domain and TGB1 also contribute significantly to replication efficiency.

The ability of T7 RNA polymerase to direct gene expression in trans from a co-infiltrated binary plasmid was evaluated by co-infiltrating N. benthamiana leaves with pCAM-T7RNAP with pGD-T7eGFP and pGD-PFGe7T, respectively containing eGFP coding sequences inserted in sense and antisense orientations relative to the CaMV 35S and bacteriophage T7 promoters. Infiltration without pCAM-T7RNAP served as a control (FIG. 15). In leaves infiltrated with pGD-T7eGFP either with or without pCAM-T7RNAP, eGFP fluorescence was detected in almost every cell (FIG. 15). In leaves infiltrated with pGD-PFGe7T alone, no eGFP expression was detected, but in leaves infiltrated with both pGD-PFGe7T and pCAM-T7RNAP, eGFP expression was detected in 19 out of 200 epidermal cells examined by LCSM. The expressed T7 RNA polymerase was detected as a 98 kDa band on a western blot (data not shown).

We next demonstrated that constructs of the full length viral clones containing both the CaMV 35S and the T7 promoters were infectious. Each full-length AltMV cDNA including the fused T7 promoter was cloned into the pGD binary vector with the 17 RNA polymerase terminator sequence downstream of AltMV to produce pGD-AltMV (3-7, 4-7, 3-1, and 4-1) (FIG. 16). In vitro transcripts from pGD-AltMV were highly infectious, yielding symptoms at 7 dpi (Table 3). When plants were agroinfiltrated with pGD-AltMV, the majority of plants were infected, but symptom expression was delayed compared to transcript inoculation (Table 3); however, when pGD-AltMV was co-infiltrated with pCAM-T7RNAP, all plants were infected, without significant delay in symptom appearance (Table 3). PCR performed on the plasmid template, and on total RNA extracted from systemically-infected leaves of plants infected by agroinfiltration in the presence of pCAM-T7RNAP clearly indicated lack of non-AltMV 5' sequence in the progeny virus population (FIG. 16).

TABLE 3

Infectivity of pGD-AltMV inoculated to N. benthamiana.

| Inoculation method | pGD-AltMV | Time to symptoms |
| --- | --- | --- |
| Agroinfiltration + pCAM-T7RNAP + pGD-p19$^a$ | 15$^d$/15$^e$ | 8-10 dpi$^f$ |
| Agroinfiltration = pGD-p19$^b$ | 10/15 | 15 dpi |
| In vitro transcription$^c$ | 15/15 | 7 dpi |

$^a$Coinfiltrated with T7 polymerase and p19
$^b$Infiltrated with p19 without T7 polymerase
$^c$XbaI cut linearized pGD-AltMV transcribed in vitro
$^d$Number of plants developing systemic symptoms
$^e$Number of plants inoculated
$^f$Days post inoculation Direct mechanical inoculation of N. benthamiana with pGD-AltMV 3-7 plasmid DNA did not result in infection under conditions that yielded infection with in vitro RNA transcripts from the same vector construct.

Since Tobacco rattle virus and PVX expression vectors were stable with a duplicated homologous subgenomic promoter (Ratcliff et al., 2001; Chapman et al., 1992), we inserted a copy of the AltMV CP-subgenomic promoter region upstream of the MCS containing eGFP as described (Lim et al, 2010, supra). In N. benthamiana and A. thaliana plants inoculated with AltMV 3-7-eGFP (TGB1$_{L88}$) or AltMV 3-1-eGFP (TGB1$_{P88}$), expression of eGFP was detected by LCSM in systemically infected leaves at 10 dpi (data not shown). At 30 dpi eGFP fluorescence was detected in styles, and petals of N. benthamiana (FIG. 17A, B). In addition, high levels of eGFP fluorescence were observed in immature seeds (FIG. 17C, D)

CP3C) consisted of an in-frame translational fusion of N- and C-terminal domains of RdRp, which overlaps TGB1. Two features of this construct were important; it has previously been demonstrated that accumulation of a defective RNA of ClYMV required maintenance of the fusion ORF (White et al., 1992), and although the minimal origin of assembly of PapMV was shown to occur within the 5' 38-47 nt (Sit et al., 1994), the initiation complexes observed by Abouhaidar & Bancroft (1978) encapsidated about 200 nt.

We created two additional 3' region constructs; pGD-5TGB123-CP3A (FIG. 19B) eliminated RdRp sequence entirely, whereas pGD-5TGB123-CP3B (FIG. 19C) provides no initiation codon within the remaining C-terminal RdRp ORF fragment (nt 4484-4720). As the 5' sequence of both of these constructs is limited to the 5' UTR, nt 1-95, they may also truncate a critical structural element identified in PVX; 5' stem-loop 1 (SL1; nt 32-106) of PVX and interactions between SL1 and the sgRNA promoter regions are required for plus-strand genomic RNA and sgRNA accumulation (Miller et al., 1998; Kim & Hemenway, 1999). SL1 has also been shown to be required for infectivity, and to bind host proteins (Kwon & Kim, 2006).

No infection was observed with [pGD-5RdRp3+pGD-5TGB123-CP3A] either with or without pCAM-T7RNAP (Table 4). Within 20 dpi, systemic symptoms were detected from [pGD-5RdRp3+pGD-5TGB123-CP3B] plus pCAM-T7RNAP, but no symptoms were detected in the absence of pCAM-T7RNAP (Table 4). When each combination was co-infiltrated with pCAM-T7RNAP, [pGD-5RdRp3+pGD-5TGB123-CP3C] produced a much higher incidence of symptomatic plants than with [pGD-5RdRp3+pGD-5TGB123-CP3B] (Table 4).

TABLE 4

Infectivity of bipartite AltMV constructs agroinfiltrated to N. benthamiana.

| 3' construct | 5' construct | | Time to visible symptoms |
| --- | --- | --- | --- |
| | RdRp + T7 polymerase[a] | RdRp only[b] | (RdRp + T7 polymerase) |
| pGD-5TGB123-CP3A | 0[c]/15[d] | 0/15 | N.A.[e] |
| pGD-5TGB123-CP3B | 1/15 | 0/15 | 15 dpi[f] |
| pGD-5TGB123-CP3C | 10/15 | 0/15 | 8-10 dpi |

[a]3' construct coinfiltrated with pGD-5RdRp3, pCAM-T7RNAP and pGD-p19
[b]3' construct coinfiltrated with pGD-5RdRp3 and pGD-p19
[c]Number of plants developing systemic symptoms
[d]Number of N. benthamiana infiltrated
[e]Not applicable
[f]Days post inoculation No plants of N. benthamiana inoculated with in vitro RNA transcripts of any combination of pGD-5RdRp3 and the various pGD-5TGB123-CP3 variants developed infection.

Because the full-length pGD-AltMV construct was about 13 Kb, there were no enzyme sites that could be used to directly insert foreign sequences. Thus, as shown in FIG. 21 it was necessary to insert the desired sequences into a 3' region subclone and then reconstruct full-length AltMV clones. In contrast, when we used bipartite constructs, five enzyme sites were available that could be used directly (FIG. 21A). We have previously shown that three amino acids in the RdRp Pol domain (P(1110), R(1121), K(1255)) and one amino acid in TGB1 (P(88)L) significantly affect AltMV RNA replication and gene silencing in infected N. benthamiana (Lim et al 2010 supra). TGB1 (P88) (AltMV 3-1 TGB1; SEQ ID NO:86 and AltMV 4.1 TGB1; SEQ ID NO:90) has very weak gene silencing suppressor function, while TGB1 (L88) (AltMV 4-7 TGB1; SEQ ID NO:84 and AltMV 3-7 TGB1; SEQ ID NO:88) acts as a strong suppressor. We therefore created two bipartite constructs differing only in TGB1 residue P(88)L (FIG. 21A), and used eGFP and PDS inserts to examine efficacy of protein expression and VIG.S respectively. Constructs pGD-5TGB1(P88)23-PDS-CP3 and pGD-5TGB1(L88)23-PDS-CP3 were separately co-infiltrated together with pGD-5RdRp3 and pCAM-T7RNAP. Construct TGB1(P88)23-PDS-CP produced the PDS silencing phenotype throughout entire leaves, while TGB1(L88)23-PDS-CP developed the silencing phenotype only in parts of the leaf (FIG. 21B). When eGFP was inserted in the MCS, the youngest leaves were observed by confocal microscopy at 30 dpi; TGB1(L88)23-eGFP-CP produced a much stronger eGFP signal than TGB1(P88)23-eGFP-CP at the same laser settings (FIG. 21C), and western blotting of systemically infected leaves confirmed the higher eGFP expression in plants infected with the $TGB1_{L88}$ construct (FIG. 21D). Symptom expression of plants infected with the GFP-expressing derivative was similar to that in plants infected with equivalent AltMV constructs without GFP (data not shown).

Expression of eGFP from an infection initiated using the binary launch system was readily detected through four passages in N. benthamiana by mechanical inoculation of sap from systemically infected tissues, by confocal microscopy; following the fifth passage, faint expression of eGFP could be detected in initially infected leaves, but not in upper leaves showing typical AltMV symptoms.

We further demonstrated that the critical substitution of Proline for Leucine at AltMV TGB1 residue 88, with its effects on efficacy of RNA silencing suppression, can be duplicated at the equivalent residues of other potexvirus TGB1 proteins. Leu residues equivalent to AltMV TGB1 residue 88 were identified by alignment of multiple potexvirus TGB1 amino acid sequences (FIG. 22B); we chose PVX and NMV for experimental manipulation, as we had isolates of these viruses available. PVX TGB1 residue 86 and NMV TGB1 residues 86 and 89 (double mutant) were mutated from Leu to Pro in cDNA clones obtained by PCR. Both the WT and mutant PVX and NMV TGB1 clones were then expressed as GFP:TGB1 fusions (pGDG-TGB1$_x$) for localization studies, and as free proteins (pGD-TGB1$_x$) to examine RNA silencing suppression.

PVX $TGB1_{P86}$ was observed to accumulate around the periphery of the nucleus and into the cytoplasm, whereas PVX $TGB1_{L86}$ yielded discrete aggregates within the nucleus (FIG. 23A); NMV $TGB1_{P86/P89}$ also accumulated adjacent to, but without apparent accumulation within, the nucleus, while NMV $TGB1_{L86/L89}$ aggregated within the nucleus (FIG. 23B), in a similar pattern to WT AltMV $TGB1_{L88}$ (FIG. 11B). Western blotting with GFP-specific antibodies revealed that WT and mutant forms of both PVX and NMV TGB1s were of the expected size (FIG. 23C). Whereas PVX $TGB1_{L86}$ and NMV $TGB1_{L86/L89}$ both showed obvious suppression of RNA silencing, both PVX $TGB1_{P86}$ and NMV $TGB1_{P86/P89}$ showed much weaker silencing suppression activity (FIG. 23D).

NMV $TGB1_{P86/P89}$ and NMV $TGB1_{L86/L89}$ were separately over-expressed from mild infectious clone AltMV 4-1 (AltMV $TGB1_{P88}$; FIG. 23E). Whereas 4-1+NMV $TGB1_{P86/P89}$ remained almost asymptomatic (as for 4-1; Lim et al., 2010 supra), 4-1+NMV $TGB1_{L86/L89}$ showed increased symptoms compared to AltMV 4-1 (FIG. 23E), suggesting that WT NMV TGB1 enhanced silencing suppression when over-expressed in the heterologous virus.

A new infectious clone of PVX, under the control of the T7 promoter, was produced in the TOPO vector (TOPO-PVX), and in vitro transcripts were shown to be infectious on *N. benthamiana*. The PVX genome, including the T7 promoter, was then transferred to pGD-T7ttr. The resulting clone, pGD-PVX, was infectious by both in vivo transcription following agroinfiltration in the presence of pCAM-T7RNAP, or from in vitro transcripts (data not shown), as previously demonstrated with pGD-AltMV variants. The PVX $TGB1_{P86}$ was substituted into pGD-PVX, and WT ($TGB1_{L86}$) and mutant ($TGB1_{P86}$) clones were agroinoculated separately to *N. benthamiana*. Symptoms of the WT ($TGB1_{L86}$) were typical mosaic, whereas the $TGB1_{P86}$ mutant induced significantly milder mottle symptoms, and western blotting of equivalent leaf extracts with PVX-specific antibodies revealed a significantly lower amount of coat protein, consistent with lower levels of replication (FIG. 23F), and the differences in RNA silencing suppression observed in the agroinfiltration assay. (FIG. 23D).

In a preferred embodiment of the present invention, a host cell containing the nucleotide sequences of the invention is a bacterial cell, in particular, an *Agrobacterium tumefaciens* cell.

For both direct gene transfer and *Agrobacterium*-mediated transfer, transformation is usually (but not necessarily) undertaken with a selectable marker which may provide resistance to an antibiotic (kanamycin, hygromycin or methatrexate) or a herbicide (sulfonylurea, imidazolinone, or basta). The choice of selectable marker is not, however, critical to the invention.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, operably linked to a promoter and/or other regulatory sequences.

As used herein, the term "express" or "expression" is defined to mean transcription alone. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences here may include promoters: T7 promoter, CaMV 35S promoter and sub-genomic promoters (two, on either side of the MCS), translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. One exemplification here is the native AltMV coat protein sub-genomic promoter which has been duplicated and is positioned on each side of MCS; however, sub-genomic promoters from other viruses can be used. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. Cloning Vectors: A Laboratory Manual; Weissbach and Weissbach. 1989. *Methods for Plant Molecular Biology*, Academic Press, New York; and Flevin at al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to a polypeptide that is substantially free of other proteins, lipids, carbohydrates or other materials with which it is naturally associated. One skilled in the art can purify proteins using standard techniques for protein purification. The purity of the polypeptide can also be determined by amino-terminal amino acid sequence analysis.

The invention includes functional polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. Functional fragments, for example, can vary in size from a polypeptide fragment as small as an epitope capable of binding an antibody molecule, to a large polypeptide capable of participating in the characteristic induction or programming of phenotypic changes within a cell.

A heterologous coding sequence refers to coding sequences which encode peptides or proteins, unrelated to, or, other than, the polypeptides provided above and which are not intrinsically found in the position provided in the chimeric gene construct.

Genes encoding the AltMV and Flexiviridae viral proteins and enzymes of the bipartite vector as well as proteins and enzymes included in the multiple cloning site can be cloned using a variety of techniques according to the invention. The simplest procedure for the cloning of such genes requires the cloning of complementary DNA from viral genomic RNA, or of genomic DNA from an organism identified as producing said protein(s), and the transfer of the cloned DNA on a suitable plasmid or vector to a host organism which does not produce the protein, followed by the identification of transformed hosts to which the ability to produce the protein has been conferred. The transforming protein function-conferring DNA can be cleaved into smaller fragments and the smallest which maintains the protein function-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode AltMV polypeptides and which hybridize under stringent conditions to the sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith at al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Unless otherwise indicated, sequence alignments and percent identity calculations were performed using the Megalign program of the LASERGENE bioinformatics computing suite (DNASTAR Inc., Madison, Wis.), or any equivalent program. Multiple alignment of the sequences was performed using the Clustal W method of alignment (Higgins and Sharp (1989. *CABIOS* 5:151-153) with the default parameters (GAP PENALTY=10, GAP LENGTH PENALTY=1.0), while default parameters for pairwise alignments using the Clustal W method were GAP PENALTY=10, GAP LENGTH PENALTY=1.0, Slow-Accurate unless otherwise indicated.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties. (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides, is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence, AltMV. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have AltMV protein-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the AltMV viral polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein. Such variants may result from, for example, genetic polymorphism or from human manipulation. Biologically active variants of a native AltMV viral protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even one amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired AltMV viral activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of AltMV viral protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

EXAMPLES

Having now generally described this invention, the same will be better understood by reference to certain specific examples, which are included herein only to further illustrate the invention and are not intended to limit the scope of the invention as defined by the claims.

Example 1

Plant Material

Seed of *N. benthamiana* were sown in 10 cm pots and grown either in a greenhouse, or in plant growth chambers at 22° C. with a 16 h/8 h light/dark regime. Three- to four-week old *N. benthamiana* plants were used for virus infection and agroinfiltration. Alternanthera dentate 'Purple Knight' was raised from seed and propagated by cuttings. For temperature treatments, inoculated plants were grown in greenhouses maintained at 15° C. and 25° C. under a 14 h light regime.

Example 2

Virus Isolates

Construction of AltMV Infectious Clones

AltMV-SP was isolated from *Phlox stolonifera* cv. Sherwood Purple by mechanical transmission to *N. benthamiana*, and serially passaged in this host over several years; AltMV-Po was isolated from *Portulaca grandiflora* and maintained in *N. benthamiana* (Hammond et al. 2006a,b, supra). Tissue of *N. benthamiana* infected with AltMV-SP and stored frozen at −70° C. from various timepoints (serial passages) was used to re-initiate the culture; total RNA was isolated from leaves of *N. benthamiana* using the RNeasy Mini Kit (Qiagen, Valencia, Calif.). Two micrograms of total RNA were used to generate cDNA using SuperScript III RNase H-Reverse Transcriptase (Invitrogen, Carlsbad, Calif.) separately with an oligo (dT)20 primer and an internal reverse primer (MluI-R) containing an Mlu I site that is unique in the sequence of AltMV-PA (Hammond et al. 2006a, supra) at nt3125. Two cDNAs were amplified by a) a 5' non coding region primer including a T7 promoter sequence upstream of AltMV nt1 (PstI-F; CTGCAGTAATACGACTCACTATAGAAAAGT AAAGCAAAGCA; SEQ ID NO:6) paired with MluI-R (AGAGCAGAATTTGCACGCGTGGGGCTG; SEQ ID NO:7), and b) MluI-F (CAGCCCC ACGCGTGCAAATTCTGCTCTCA; SEQ ID NO:8) and XbaI-R1 (GAGAGTCTAGATTTTTTTTTTTTTTTTTTTT; SEQ ID NO:9) respectively; the two PCR products were separately cloned to the TOPO vector (Invitrogen, Carlsbad, Calif.), yielding four clones containing the 5' portion of the genome (nt 1-3143), and seven clones containing the 3' region (nt3117 to the poly(A) tail); each clone contains an MluI site at nt3125. The seven 3' region clones were each digested individually with MluI and XbaI, and each insert individually ligated into each of the 5' region clones similarly cleaved with MluI and XbaI to create 28 distinct full-length AltMV clones. Each of the full-length clones was linearized with XbaI for in vitro T7 RNA transcript production (see below); transcripts were inoculated to young plants of *N. benthamiana* (3 plants per transcribed clone). Inoculated plants were tested for infection by RT-PCR using AltMV-specific primers PP12 (AATCCTTGCCCTGCTGTC; SEQ ID NO:10) and PP15 (TCAGAAGCACTATGTGACAT; SEQ ID NO:11).

Example 3

Substitution of Pol and TGB1 in Chimeric AltMV Clones

3' region TOPO clones 1 and 7 were used for preparation of chimeric vectors. The Pol domain of mild symptom 3' region clone 1 was digested with Mlu I (at nt3125) and Bam HI (at nt4484) and the Pol domain exchanged with the Mlu I/Bam HI Pol fragment of severe symptom clone 7. To replace both the Pol and TGB1 domains, clone 1 was digested with Mlu I (nt3125) and Xma I (nt5480) and this fragment replaced with the clone 7 Mlu I/Xma I Pol+TGB1 fragment. The Clone 1 TGB1 fragment was substituted by the clone 7 TGB1 fragment using the Bam HI/Xma I fragment of clone 7, and the TGB1 fragment of clone 7 similarly substituted by the Bam HI/Xma I fragment of clone 1. Because the Bam HI/Xma I fragment also included the P(1535)S difference between clones 1 and 7, P(1535) was altered to S(1535) so that the differences due to TGB1 residue 88 could be evaluated independently. Overlap PCR (Wurch et al. 1998. Biotech. Techniques 12: 653-657) was used to substitute S(1535) into clone 1 using primers Pol-F (GGAGTTCTGTGGATACAGGAT-TACGCCCA [SEQ ID NO:12])/(P to S)-R (TTCATCTTTG-GAAGAAAAGTTTT [SEQ ID NO:13]) and (P to S)-F (CCCAAAGAT GAATCACTTTACT [SEQ ID NO:14])/ Pol-R (TAGGGACCTCCAAAGGGCAGTTGATG AATATT [SEQ ID NO:15]). The structures of all chimeric clones were confirmed by sequence analysis. The chimeric 3' subclones were then digested with Mlu I and Xba I and combined with appropriate Mlu I/Xba I cleaved 5' region TOPO clones to create chimeric full-length clones 4-1$_{PRK}$ (4-1 with Pol from clone 7); 4-1L (4-1 with TGB1 from clone 7); 4-1$_{PRKL}$ (4-1 with Pol+TGB1 from clone 7); and 3-7$_{Pol 4-1}$ (3-7 with Pol from clone 1).

Example 4

In Vitro Transcription Reactions and Plant Inoculations

Full-length AltMV cDNA clones were linearized with Xba I and transcript RNA was generated using T7 RNA polymerase as described by Petty et al. (1989). The transcribed RNAs were precipitated and resuspended in 20 µl of GKP buffer (50 mM glycine, 30 mM KHPO4, pH9.2, 1% bentonite, 1% celite) per 50 µl transcription reaction and 10 µl used per leaf to inoculate *Nicotiana benthamiana* (Petty et al. 1989. *Virology* 171:342-349).

Example 5

Quantitative Real-Time Reverse Transcription PCR (Q-RTPCR)

Total RNA was isolated from leaves of *N. benthamiana* using the RNeasy Mini Kit (Qiagen, Valencia, Calif.) and the extracted RNA was treated with DNase I according to manufacturer's recommendation. Two micrograms of total RNA were used to generate cDNA in a 20 µl reaction using Super-Script III RNase H-Reverse Transcriptase (Invitrogen, Carlsbad, Calif.) with 0.5 µg of an oligo (dT)$_{20}$ primer: Q-RTPCR was performed with the selected primer sets (Coat: Coat-F=ATCATCTGGAACCTCAG AACAGAC [SEQ ID NO:16], Coat-R=TGAAAGAGGTTTACCTGCTTGTTAG [SEQ ID NO:17]; RdRp: RdRp-F=AAGAGGTCCAAACTTCAATACTTCC [SEQ ID NO:18], RdRp-R=GAAGGAAGTGTAGTGTGTCTCCAAT [SEQ ID NO:19]; Actin: Actin-F=GTTGGCTTACATTGCTCTTGACTAT [SEQ ID NO:20], Actin-R=GTTTCCGTACAG ATCCTTTCTGAT [SEQ ID NO:21]) using an Mx3005P® QPCR System and Brilliant® SYBR® Green QPCR Master Mix (Stratagene, La Jolla, Calif.) as described by Bae et al. (2006. *Plant Physiol.* 141:1056-1057). Each 25 µl Q-RTPCR reaction contained 12.5 µL of 2× Brilliant SYBR® Green QPCR Master Mix, 5 µl of ten-fold diluted cDNA, 2.5 pM of each gene-specific primer and diluted reference dye (final concentration=300 nM). The conditions used for Q-RTPCR reactions were: 95° C. for 10 min, followed by 40 cycles of 95° C. for 30 sec, 60° C. for 1 min, and 72° C. for 30 sec. A putative EST sequence encoding a chlorophyll a-b binding protein 50 (LHCII type I CAB-50, LHCP) was obtained from the "The DFCI *Nicotiana benthamiana* Gene Index (NbGI)" (http://compbio.dfci.harvard.edu/tgi/cgi-bin/tgi/gireport.pl?gudb=N. benthamiana) and used as an internal control. Relative transcript levels of each target (AltMV CP or RdRp, LHCP) were normalized with respect to *N. benthamiana* ACTIN (accession no. AY179605) transcript levels (% of ACTIN), which is a constitutively expressed gene. Four biological replications were used to calculate mean values.

Example 6

Identification of the Original AltMV-SP Sequence from *N. benthamiana*

RNA was extracted and cDNA produced as described above, from an infection established from the oldest available tissue stored at −70° C. (frozen approximately 3 years prior to the passage from which the infectious clones were produced). A PCR product spanning the nt3125 MluI site junction of the 5' and 3' region clones was amplified with primers PP3 (CCCCCACGAAGCCCACAGTCATC [SEQ ID NO:22])/ PP20 (CATTTGCACAAAGGTATCCTC [SEQ ID NO:23]). The PCR products were cloned into the TOPO vector, and 15 clones were sequenced using sequencing primers M13F and M13F (Invitrogen).

Example 7

Construction of AltMV 3-1:eGFP, 4-1:eGFP, 3-7:DxRed, and 4-7:DsRed

A multiple cloning site (MCS) including Nco I, Bam HI, Mlu I, Bgl II and Nhe I restriction sites was inserted immediately upstream of the CP gene in a 3'-terminal subclone of full-length clone 3-1 by overlap PCR (Wurch et al., supra). The TGB21TGB3 region was amplified using a forward primer (TGB2/3-F; GAGAAGCTTTCCCTCGCCC GGG-GACAATATT; SEQ ID NO:24) introducing a Hind III site (to aid subcloning) upstream of the Xma I site at nt5480, and reverse primer MCS-R (CATAGATCTACG CGT GGATCCCATGGGATGACTTCAACTAGGA; SEQ ID NO:25) that added Bgl II, M/u I, Bam HI, and Nco I sites at the end of the TGB3/CP intergenic region; the CP-3'UTR fragment was amplified with forward primer MCS-F (G GGATCCACGCGTAGATCTAT GCTAGCATGTCTA-CACCATTTCCT; SEQ ID NO:26) adding Bam HI, Mlu I, Bgl II, and Nhe I sites immediately upstream of the CP gene, and reverse primer XbaI-R1 (see Example 2 above). These two fragments were then combined by amplification using the flanking. (TGB2./3-F and XbaI-R1[see just above]) primers, and the product cloned into the Hind III and Xba I sites of pUC18 to form pAltMV:MCS.

The CP subgenomic (sg) promoter was duplicated by amplification (from AltMV 3-1) of a fragment containing the sg promoter, CP, and 3' UTR using Nhe I-modified forward primer NheI-F (GCTAGCCACCAGAGACCATCAGGG; SEQ ID NO:27) and reverse primer XbaI-R2 ( TCTAGATTTTTTTTTTTTTTTTT; SEQ ID NO:28). The PCR product was digested with Nhe I and Xba I, and substituted for the Nhe I/Xba I CP-3' UTR fragment of pAltMV: MCS to yield pAltMV:MCS:sg.

The eGFP and DsRed genes were amplified from pGDG and pGDR (Goodin et al. 2002. *Plant J.* 31: 375-383) respectively, using primers to introduce 5' Nco 1 and 3' Nu I or Nhe I sites (eGFP NcoI-F(GAGAA CCATGGGTAAAGGAGAAGAACTTTT; SEQ ID NO:29)/ eGFP MluI-R (AAAAAGATTAGTCTTCACCATGG ACGCGT; SEQ ID NO:30); and DsRed NcoI-F(GAGAA CCATGGCCTCCTCCGAGAACGTCAT [SEQ ID NO:31])/DsRed NheI-R (GACTA GCTAGCTTATCTCAGGAACAGGT [SEQ ID NO:32]), respectively, and separately inserted into the MCS of pAltM-V:MCS:sg. The eGFP-containing 3' region of the AltMV genome was then substituted into full-length mild clones 3-1 and 4-1 as an Xma I/Xba I fragment to form 3-1:eGFP and 4-1:eGFP, and the Xma I/Xba I fragment containing DsRed similarly substituted to the severe clones 3-7 and 4-7 to form 3-7:DsRed and 4-7:DsRed.

Example 8

Construction of a Bipartite AltMV Delivery System

First we generated an AltMV RdRp construct with homologous AltMV 5' and 3' non-coding region. The AltMV 3' non-coding region from nt 6482-6607 and poly(A) tail was amplified from pGD:AltMV using Spe I forward (AAAAAC-TAGTACTAGCATAAC CCCTTGGGG; SEQ ID NO:33) and Xba I reverse (XbaI-R1, see above) primers, and inserted into pGD-T7ttr digested with the same enzymes. The T7 promoter, AltMV 5' non-coding region and complete RdRp coding sequence were amplified from pGD:AltMV using PstI forward (GAGCTGCAGTAATACGACTCACTATA-GAAAAGTAA AGCAAAGCA; SEQ ID NO:34) and Spe I reverse (GAGACTAGTTAAGTAAAGTGAT TCATCTTTG; SEQ ID NO:35) primers, and inserted into the Pst I/Spe I digested pGD-T7ttr derivative already containing the 3' non-coding region, creating pGD:5RdRp3. A construct containing the Triple Gene Block and CP gene between the 5' and 3' non-coding regions (pGD-5TGB123-CP3C) was prepared by digesting pGD:AltMV with Bam HI and religation lacking a Bam HI fragment (nt 224-4484); the resulting pGD-5TGB123-CP3C has an in-frame translational fusion of N- and C-terminal domains of RdRp, which overlaps TGB1. Each of constructs pGD:5RdRp3 and pGD-5TGB123-CP3C has both CaMV 35S and T7 promoters upstream of the AltMV sequence. Co-agroinfiltration of a susceptible host in the presence of pCAM:T7RNAP and pGD:p19 results in in vivo transcription and recombination to yield a full-length AltMV genome. Derivatives of pGD-5TGB123-CP3C with a multiple cloning site are suitable for expression of additional sequences for protein expression (with $TGB1_{L88}$) or VIGS (with $TGB1_{P88}$).

Example 9

Substitution of TGB1 Residues of AltMV, PVX or PlAMV-NMV to Reduce Efficacy of Silencing Suppression Substitution of a naturally occurring variant of AltMV TGB1, with residue Pro88 ($TGB1_{P88}$) instead of Leu88 ($TGB1_{L88}$) into pGD:$AltMV_{3-7}$ (creating pGD:$AltMV_{3-7P}$) resulted in a significant decrease in the efficacy of RNA silencing, milder symptoms, and a lower level of viral replication. Reduced silencing suppression efficacy of $TGB1_{L88}$ was demonstrated in an in vivo silencing suppression assay.

Substitution by site-directed mutagenesis by overlap PCR (Wurch et al., supra) of PVX TGB1 residue Leu86 (PVX $TGB1_{L86}$) with Pro86 (PVX $TGB1_{P86}$) (PVX TGB1 L>P top=AGTATACTCCGGACAACACCACAAGG [SEQ ID NO:36], PVX TGB1 L>P bottom=TGTTGTCCGGAGTATACTCATCGAGGAT [SEQ ID NO:37], PVXTGB1 L(86)P forward=TAATGCACAGATTTTCCTAGGCACGTTATC [SEQ ID NO:38], PVXTGB1 L(86)P reverse=ACTAGTTTTTTTTTTTTTATTTATATTATTCAT [SEQ ID NO:39]), and of PlAMV-NMV TGB1 residues Leu (86,89) (NMV $TGB1_{L86,89}$) with Pro(86,89) (NMV TGB1 LL>PP top=GCGCCCCAACCGCTCAAGGGCTCTT [SEQ ID NO:40], NMV TGB1 LL>PP bottom=CTTGGGCGGTTGGGGCGCTGCGTAT [SEQ ID NO:41], NMV TGB1-F=GAGA CTCGAGAAATGGACGCAATTATTTCAACACTGA [SEQ ID NO:42], NMV TGB1-R=GAGA GGATCCTCAGTAGGTGGGGGTGAGGTG GTG [SEQ ID NO:43]) (NMV $TGB1_{P86,89}$) had similar effect on efficacy of RNA silencing suppression activity in the in vivo silencing suppression assay, and the substitution of PVX $TGB1_{P86}$ into an infectious clone of PVX demonstrated to have similar effects as for AltMV on symptom expression and viral replication. For each of the AltMV, PVX, and PlAMV-NMV TGB1 mutants, GFP:TGB1 fusions of TGB1 mutants with lower efficiency of RNA silencing suppression (Pro substitutions) were demonstrated to accumulate primarily at the periphery of the nucleus, whereas the efficient suppressors with wild-type Leu at the critical residue(s) accumulated to a significant extent within the nucleus, and particularly at the nucleolus.

Substitution of PVX $TGB1_{P86}$ into an infectious clone of PVX reduced RNA silencing suppression activity, creating a vector more suitable for VIGS usage. The PVX $TGB1_{P86}$ was substituted into pGD-PVX, and WT ($TGB1_{L86}$) and mutant ($TGB1_{P86}$) clones were agroinoculated separately to *N. benthamiana*. Symptoms of the WT ($TGB1_{L86}$) were typical mosaic, whereas the $TGB1_{P86}$ mutant induced significantly milder mottle symptoms, and western blotting of equivalent leaf extracts with PVX-specific antibodies revealed a significantly lower amount of coat protein, consistent with lower levels of replication, and the differences in RNA silencing suppression observed in the agroinfiltration assay.

Example 10

Use of Co-Expressed T7 Polymerase to Increase Efficiency and Speed of AltMV Infection via Agroinfiltration

Required for Infectivity of the Bipartite Delivery System

When pGD:AltMV was co-agroinfiltrated with pGD:p19 alone, only 10 of 15 *N. benthamiana* plants were infected, with visible symptoms appearing at about 15 days post inoculation (dpi). When construct pCAM:T7RNAP was included in addition to pGD:AltMV and pGD:p19, 15 of 15 agroinfiltrated plants were infected, with visible symptoms appearing at 7 dpi.

*Nicotiana benthamiana* was co-infiltrated with pGD-5RdRp3 paired with pGD-5TGB123-CP3C, in the presence or absence of pCAM-T7TRNAP. Symptoms of infection were observed within 8-10 dpi when pCAM-T7RNAP was included; no symptoms were detected in the absence of pCAM-T7RNAP. To determine whether the bipartite nature of the virus was maintained in infected plants, total RNA was purified from symptomatic leaves of systemically infected plants, and amplified using primers specific for the 5' (CTG-CAGTAATACGACTCACTATAG; SEQ ID NO:44) and 3' (GAGAGTCTAGATTTTTTTTTTTTTTTTTTTT; SEQ ID NO:45) UTRs. A single large PCR product equivalent to that from plants infected with pGD-AltMV was detected, without significant products representing the RdRp and TGB123-CP genome fragments, indicated that the two RNAs had recombined in planta. Sequence analysis of progeny virus across the RdRp:TGB1 junction revealed an identical sequence to the parental full-length clone in all six PCR clones examined, indicating that precise recombination had occurred in the region of overlap between the RdRp and TGB123-CP constructs.

Example 11

Construction of AltMV 3-$7_{Po-CP}$ and CP Mutants

The CP gene and 3' UTR of *portulaca* isolate AltMV-Po (Hammond et al., 2006a,b) was amplified using primer Po-CP-F (GAGCCATGGCCATGTCCACTC CATTTCCT-CAAGTC; SEQ ID NO:46) adding an Nco I site immediately upstream of the CP gene, paired with vector primer XbaI-R1

(see [0148] above), and substituted into pAltMV:MCS; the Xma I/Xba I fragment of pAltMV:MCS:Po-CP was then substituted into full-length clone 3-7 to form AltMV 3-7$_{Po\text{-}CP}$.

Overlap PCR (Wurch et al., supra) was utilized to mutate selected residues of the AltMV 3-7 CP to the residues present in AltMV-Po. Thus mutants MN(13,14)ID, T(66)A, LA(76, 77)IS, T(154)A, and MN(13,14)ID+LA(76,77)IS were produced using the primers indicated (for CP MN(13,14)ID: TGB2start F=ATGTCCGGGCTCCCCCACT CCCTGA [SEQ ID NO:47], (MN to ID)-R=GT ctATCTGTTCCTGGGTGACTTG [SEQ ID NO:48], (MN to ID)-F=GAACAGATagACGCCTTCACCCC [SEQ ID NO:49], and XbaI-R1 [see 0148]; for CP (T66 to A):TGB2start F (see just above), (T66 to A)-R=GGcACT GGAGCCATTGTCATAAC [SEQ ID NO:50], (T66 to A)-F=GGCTCCAGTgCCTACAC AGCGGT [SEQ ID NO:51], XbaI-R1 [see 0148]; for CP(LA76,77 to IS): TGB2start F (see just above), (LA to IS)-R=GagAtTGAAGAAGGGCCCACCACC [SEQ ID NO:52], (LA to IS)-F=CCCTTCTTCAaTctCAGAGGTCT [SEQ ID NO:53], XbaI-R1 (see [0148]; for CP(T154 to A): TGB2start F (see just above), (T154 to A)-R=GAGcCCTAACCAA CCCTCCTGGTGG [SEQ ID NO:54], (T154 to A)-F=TTGGTTAGGgCTCCCAGCCAAG CAG [SEQ ID NO:55], XbaI-R1 (see [0148]).

Example 12

Substitution of AltMV-Po CP in AltMV Infectious Clones Reduces Symptom Severity

Plants of N. benthamiana inoculated with pGD:AltMV$_{3-7}$, pGD:AltMV$_{4-7}$, developed severe mosaic, and if grown at 15° C., developed systemic necrosis and typically died within 30 days. Inoculated plants of Alternanthera 'Purple Knight' developed premature anthocyanin coloration at 25° C., and stunting. In contrast, when the AltMV-Po CP was substituted for the AltMV-SP CP of severe clones 3-7 or 4-7 (AltMV 3-7$_{CP\text{-}Po}$, AltMV 4-7$_{CP\text{-}Po}$), plants of N. benthamiana developed mild mosaic, even if grown at 15° C., and no necrosis developed; plants of Alternanthera 'Purple Knight' did not develop premature anthocyanin coloration, and were not stunted. Thus substitution of AltMV-Po CP reduces symptom severity in N. benthamiana and Alternanthera 'Purple Knight'.

Example 13

Substitution of AltMV-Po CP in AltMV Infectious Clones Prevents Death of Soybean Soybean plants inoculated with pGD:AltMV$_{3-7}$, pGD: AltMV$_{4-7}$, or pGD:AltMV$_{4-1}$, plants either died as a result of apical necrosis, or the inoculated leaves became necrotic and abscised without systemic infection occurring. Soybean plants inoculated with AltMV 3-7$_{CP\text{-}Po}$ or AltMV 4-7$_{CP\text{-}Po}$ became systemically infected, with mild mosaic symptoms. Thus substitution of AltMV-Po CP allows AltMV to be used as a vector in soybean, as well as reducing symptom severity in N. benthamiana and Alternanthera 'Purple Knight'.

Example 14

Infectious clones Containing the AltMV or PVX Genome Downstream of Both CaMV 35S and T7 Promoter Sequences Offer Flexibility of Usage The infectious clone pGD:AltMV contains the AltMV sequence immediately downstream of the bacteriophage T7 polymerase, with the CaMV 35S promoter an additional 54 nucleotides upstream. Agroinfiltration of N. benthamiana with pGD:AltMV in the presence of pGD:p19 resulted in infection of 10 of 15 plants, with visible infection by 15 dpi. When pGD:AltMV was agroinfiltrated in the presence of both pGD:p19 and pCAM:T7RNAP, 15/15 plants were infected, with visible symptoms at 7 dpi. In vitro RNA transcripts from pGD:AltMV inoculated to N. benthamiana resulted in infection of 15/15 plants with visible symptoms at 7 dpi.

A new infectious clone of PVX, under the control of the T7 promoter, was produced in the TOPO vector (TOPO-PVX), and in vitro transcripts were shown to be infectious on N. benthamiana. The PVX genome, including the T7 promoter, was then transferred to pGD-T7ttr. The resulting clone, pGD-PVX, was infectious by both in vivo transcription following agroinfiltration in the presence of pCAM-T7RNAP, or from in vitro transcripts (data not shown), as previously demonstrated with pGD-AltMV variants.

This contrast with reports for other viruses, where separate constructs have proven necessary for 35S (in vivo) transcription and 17, T3 or SP6 in vitro transcription (e.g. Baulcombe, 1995, supra), or where non-viral nucleotides between the promoter and the 5' end of the viral sequence have significant compromised or abolished transcript infectivity (e.g. Boyer and Haenni, 1994, *Virology* 198: 415-426).

Example 15

Agrobacterium Infiltration, AltMV Constructs, Subcellular Localization, and Silencing Suppression Assays All binary vectors used in these studies were derived from pGD or pGDG as previously described (Goodin et al., supra). The TGB1 gene of AltMV 3-1 and 3-7 (TGB1 XhoI-F=GAGA CTCGAGAAATGAATCACTTTACTAACCTCA[SEQ ID NO:56], TGB1 BamHI-R=GAGA GGATCCTTTATTACTAAAGCTAAACTAACT [SEQ ID NO:57]), and TGB2 (TGB2 XhoI-F=GAGA CTCGAGAAATGTCCGGGCTCCCCCA [SEQ ID NO:58], TGB2 BamHI-R=GGATCCCTAAGAGCAGCAAGGA [SEQ ID NO:59]) and TGB3 (TGB3 XhoI-F=CTCGAGAAATGCCCTATCTTGTAGAG [SEQ ID NO:60], TGB3 BamHI-R= GGATCCCTAAAACCTAAGCCAAAGCAGAG [SEQ ID NO:61]) of 3-7 were separately amplified and inserted to the Xho I and Bam HI sites of pGD. Constructs pGD:smGFP (soluble modified GFP), and pGD:p19 (Tomato bushy stunt virus p19) were a gift of Andy Jackson (Bragg and Jackson. 2004. *Molecular Plant Path.* 5: 465-481). pGD:HC-Pro (Soybean mosaic virus [SMV] HC-Pro) was created by amplification of HC-Pro using HC-Pro XhoI-F (GAT CTCGAGAAATGTTTTTCCGT GGTTGGAAAAAG-GTGT [SEQ ID NO:62])/HC-Pro XmaI-R (GAG CCCGGGTAG AATTTCATCTCACTCTG [SEQ ID NO:63]) from pG5-Hc-Pro (Lim et al. 2005. *Plant Physiol. Biochem.* 43: 1014-1021). AltMV-SP CP and AltMV-Po CP were separately amplified (Coat XhoI-F=GAGA CTCGAGATATGTCTACACCATTTCCT [SEQ ID NO:64], Coat BamHI-R=GAGA GGATCCTCA CTCAGGTC-CTGGGAG [SEQ ID NO:65]), and each inserted into both pGD (as free CP) and pGDG (as a GFP:CP fusion) vectors at the Xho I and Bam HI sites.

*Agrobacterium tumefaciens* infiltrations of N. benthamiana leaves were performed essentially as described by Johansen and Carrington (2001. *Plant Physiol.* 126:930-938). *Agrobacterium* EHA105 was separately transformed with each of the pGD-derived constructs; colonies were scraped from fresh plates and diluted to approximately $A_{600}$=0.4 in infiltration buffer (10 mM MES pH 5.6, 10 mM $MgCl2$) containing 150 μM 3',5'-dimethoxy-4'-hydroxyacetophenone (Aldrich, Milwaukee, Wis.). When more than one culture was used for co-agroinfiltration, each culture was diluted to $OD_{600}$=0.4 before adding to the mixture. The bacteria were then incubated at room temperature for 2 to 3 h before pressure infiltration with a 1-cc syringe at the underside of the leaf.

To test silencing suppressor activity, we used an smGFP suppression assay as described (Bragg and Jackson, supra). Because 35S promoter-controlled GFP induces silencing of GFP expression (Silhavy and Burgyán. 2004. *Trends Plant Sci.* 9:76-83; Shiboleth et al. 2007. *J. Virol.* 81: 13135-13148), we used only pGD:smGFP co-infiltrated with the silencing suppressor. Construct pGD:smGFP was co-infiltrated with pGD:AltMV TGB1(3-7[88(L)]; and 3-1 [88(P)]), pGD: TGB2, pGD:TGB3, pGD:CP (AltMV-SP, 3-7) and pGD:p19, respectively.

Example 16

Western Blotting

AltMV infections were confirmed as necessary using western blotting as previously reported (Hammond et al. 2006b, supra) using a 1:2000 dilution of AltMV-specific antibody (a gift of Andrew Geering; Geering and Thomas, supra). PVX infections were detected using a 1:400 dilution of PVX-specific antibody (Agdia). GFP fusion proteins were detected using anti-GFP Living Colors monoclonal antibody diluted as recommended by the manufacturer (Clontech). T7 RNA polymerase was detected using anti-T7 RNA polymerase monoclonal antibody diluted as recommended by the manufacturer (Novagen).

Example 17

Detection of Fluorescence in *N. benthamiana* Epidermal Cells

Expression of smGFP in leaves of whole plants was detected using a Fujifilm LAS-1000 imaging system (Fujifilm USA, Stamford, Conn.). Fluorescence in epidermal cells of *N. benthamiana* leaves was visualized by laser scanning confocal microscopy (LSCM) using a Zeiss LSM 410 or a Zeiss LSM 710 microscope (Carl Zeiss MicroImaging, Inc., Thornwood, N.Y.). For the Zeiss LSM 410, an Argon laser was used to excite GFP at 488 nm and an emission band pass was detected between 500 to 520 nm. DsRed was excited at 543 nm, and the emission was passed to the PMT detector through the same filter as used for GFP, as well as through a LP570 nm emission filter.

For the Zeiss LSM 710, an Argon laser was used to excite eGFP at 488 nm and emission was monitored between 500 to 520 nm. The images were observed using an AxioObserver inverted microscope with a 40×1.2 NA water immersion Plan Apochromatic objective. A photomultiplier tube captured the light emitted from a 488 nm argon laser with a pin hole of 3.7 μm passing through a MBS 488 filter with limits set between 492-543 nm. The Zeiss Zen software package was used to obtain the images. Cell wall staining experiments utilized 70 μg/ml of Calcofluor Blue (Sigma-Aldrich) that was added to 0.7 M sucrose and infiltrated for 30 min before observing with the microscope. Nuclear localization was confirmed as necessary by staining nuclei with DAPI (Deng et al., 2007).

Example 18

Yeast Two-Hybrid Assays

Yeast two-hybrid vectors (James et al. 1996. *Genetics* 144: 1425-1436), were designed to produce fusions of either the Gal4 activation domain (AD) or the Gal4 binding domain (BD) to the N-terminus of the proteins to be tested for interactions. To construct fusions to the AD (pGAD:Coat, pGAD: Coat-Po) and the BD (pGBDU:Coat, pGBDUCoat-Po), CP sequences were amplified using primers Y2H EcoRI-F (ATC GAATTCATGTCTACACCATTTCCTCAA; SEQ ID NO:66) and Y2H BamHI-R (GAGA GGATCCTCACTCAGGTCCTGGGAG; SEQ ID NO: 67) and introduced into the EcoRI and BamHI sites of pGDBU, and of pGAD. The yeast strain PJ69-4A was transformed with LEU2 selected activation domain (AD) and URA3 selected binding domain (BD) constructs as previously described (Becker et al. 1991. *Proc. Natl. Acad. Sci. USA* 88: 1968-1972). To select for transformants containing both the AD and BD plasmids, transformed yeast were plated on SD-glucose medium containing 20 mg/L Ade, Met, Trp, and His, and 30 mg/L Lys and were grown for 3 days at 28° C. Yeast colonies were tested for interactions through expression of the reporter genes ADE2 and HIS by streaking on SD-glucose medium containing 20 mg/L Met and Trp, and 30 mg/L Lys and growing for three to five days at 28° C. or at room temperature.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An Alternanthera mosaic virus (AltMV) bipartite launch system comprising:
   (a) a first construct comprising an AltMV RNA-dependent RNA polymerase (RdRp), operably linked to a CaMV 35S promoter or other suitable plant promoter and a T7 promoter or other suitable bacteriophage promoter;
   (b) a second construct comprising in order an AltMV partial RdRp, shown schematically in FIG. 19D, an AltMV Triple Gene Block 1 (TGB1), an AltMV Triple Gene Block 2 (TGB2), an AltMV Triple Gene Block 3 (TGB3), a subgenomic promoter operably linked to a multiple cloning site (MCS), and a subgenomic promoter operably linked to an AltMV Coat Protein (CP); and
   (c) a third construct encoding a T7 RNA polymerase (T7RNAP);
   wherein the second construct is operably linked to a CaMV 35S promoter or other suitable plant promoter and a T7 promoter or other suitable bacteriophage promoter,
   the TGB1 amino acid sequence is the sequence set forth in SEQ ID NO: 84 or SEQ ID NO: 88,
   the first and second construct undergo recombination in planta within a short overlap of a common sequence of the partial RdRp present in both constructs,
   and the AltMV bipartite launch system is capable of high level protein expression in a plant.

2. The AltMV bipartite launch system of claim 1 wherein the AltMV CP is any one of the sequences set forth in SEQ ID NOs: 5, 81, or 82.

3. The AltMV bipartite launch system of claim 1 wherein the AltMV RdRp is encoded for by SEQ ID NO: 4, and wherein the AltMV amino acid sequence encoded for by SEQ ID NO: 4 comprises a substitution from arginine to proline at amino acid position 1110 of the encoded AltMV RdRp, a substitution from lysine to arginine at amino acid position 1121 of the encoded AltMV RdRp, a substitution from arginine to lysine at amino acid position 1255 of the encoded AltMV RdRp, and substitution from serine to proline at amino acid position 1535 of the encoded AltMV RdRp.

4. The AltMV bipartite launch system of claim 1 wherein said AltMV bipartite launch system further comprises a fourth construct encoding a heterologous viral silencing suppressor.

5. The AItMV bipartite launch system of claim 4 wherein the heterologous viral silencing suppressor is a tombusvirus p19 (TBSVp19) protein.

6. An Alternanthera mosaic virus (AItMV) bipartite launch system comprising:
(a) a first construct comprising an AItMVRdRp, operably linked to a CaMV 35S promoter or other suitable plant promoter and a T7 promoter or other suitable bacteriophage promoter;
(b) a second construct comprising in order an AItMV partial RdRp, shown schematically in FIG. 19D, AItMV TGB1, an AItMV TGB2, an AItMV TGB3, a subgenomic promoter operably linked to a MCS, and a subgenomic promoter operably linked to an AItMV CP; and
(c) a third construct encoding a T7RNAP;
wherein the second construct is operably linked to a CaMV 35S promoter or other suitable plant promoter and a T7 promoter or other suitable bacteriophage promoter,
the TGB1 amino acid sequence is the sequence set forth in SEQ ID NO: 86 or SEQ ID NO: 90,
the first and second construct undergo recombination in planta within a short overlap of a common sequence of the partial RdRp present in both constructs, and
the AItMV bipartite launch system is capable of virus-induced gene silencing in a plant.

7. The AItMV bipartite launch system of claim 6 wherein the AItMV CP is any one of the sequences set forth in SEQ ID NOs: 5, 81, or 82.

8. The AItMV bipartite launch system of claim 6 wherein the AItMV RdRp is encoded for by SEQ ID NO: 4, and wherein the AItMV amino acid sequence encoded for by SEQ ID NO: 4 comprises a substitution from arginine to proline at amino acid position 1110 of the encoded AItMV RdRp, a substitution from lysine to arginine at amino acid position 1121 of the encoded AItMV RdRp, a substitution from arginine to lysine at amino acid position 1255 of the encoded AItMV RdRp, and substitution from serine to proline at amino acid position 1535 of the encoded AItMV RdRp.

9. The AItMV bipartite launch system of claim 6 wherein said AItMV bipartite launch system further comprises a fourth construct encoding a heterologous viral silencing suppressor.

10. The AItMV bipartite launch system of claim 9 wherein the heterologous viral silencing suppressor is a tombusvirus p19 (TBSVp19) protein.

11. A host cell comprising the AItMV bipartite launch system of claim 1 or claim 6.

12. A plant, plant cell, plant part, or plant seed comprising the AItMV bipartite launch system of claim 1 or claim 6.

13. A method of advantageously manipulating and analyzing one or more genes or gene fragments for expression of phenotypic characteristics comprising:
(a) inserting one or more genes or gene fragments into the MCS of the AItMV bipartite launch system of claim 1; and
(b) introducing the AItMV bipartite launch system into a plant;
wherein recombination of the first construct and the second construct of the AItMV bipartite launch system occurs in planta at the overlap of a common sequence of the partial RdRp that is present in both constructs, and
said genes or gene fragments are expressed in the plant.

14. A method of advantageously manipulating and analyzing one or more genes or gene fragments for silencing effects comprising:
(a) inserting one or more genes or gene fragments into the MCS of the AItMV bipartite launch system of claim 6; and
(b) introducing the AItMV bipartite launch system into a plant;
wherein recombination of the first construct and the second construct of the AItMV bipartite launch system occurs in planta at the overlap of a common sequence of the partial RdRp that is present in both constructs, and
said genes or gene fragments induce gene silencing in the plant.

15. A method of obtaining high levels of expression of one or more heterologous genes in planta comprising:
(a) infecting a plant with the AItMV bipartite launch system of claim 4 or claim 5, wherein said AItMV bipartite launch system comprises said one or more heterologous genes inserted in the MCS of said AItMV bipartite launch system;
wherein recombination of the first construct and the second construct of the AItMV bipartite launch system occurs in planta at the overlap of a common sequence of the partial RdRp that is present in both constructs, and
said genes or gene fragments are expressed in the plant at a level that is higher than expression from said AItMV bipartite launch system that does not comprise the heterologous viral silencing suppressor.

16. A method of increasing replication and levels of protein expression of one or more heterologous genes in planta comprising:
(a) infecting a plant with the AItMV bipartite launch system according to the method of claim 11 or claim 12; and
(b) growing said plant at a temperature between 15 degrees Celsius and 25 degrees Celsius.

* * * * *

SEQUENCE LISTING

<160> NUMBER OF SEQ ID NOS: 90

<210> SEQ ID NO 1
<211> LENGTH: 6607
<212> TYPE: DNA
<213> ORGANISM: Alternanthera mosaic virus

<400> SEQUENCE: 1

```
gaaaagtaaa gcaaagcaaa gcaaagcaaa gaaactgaaa gtctatattt gcccttcgag        60
gagatcgatt acccatcccg gctagatcaa cagtatggca cactttcgtt ctgttcttga       120
ccaaatgaac gatcccagcc tccgggcggt cattcaagaa gaagcttacc gcgaaattaa       180
aaaaaccatc gcggaaacca acagtacaa tccttacgcc caggatccag cggcggctga       240
ctcattagag aaattaggaa tagaatctaa ccccttctca gtccgcgccc atacacacgc       300
ggccgcgaag tctatagaat tagacatgta caaaatcacg ggttactccc tcccaaagga       360
gaatccaatt acttttcttt tcatgaagag gtccaaactt caatacttcc acagaggacc       420
acagcatgga gacttgttcc ttaacgcttg gattgagcca aggacgtca ccaggtacaa        480
cttagaagac ctcttcaaac cttccatcac cccagaaatc caaactagag tggcattcat       540
tggagacaca ctacacttcc ttcccctagg ggctatcaga gagatattta caagctccca       600
aaaacttcaa actctctatg caacaatggt actgcccccc gaagccatgc acagaatgca       660
ctcaattcac cccagcattt acgagctaga attccatgaa agaaatttca tatacaagcc       720
gggaggacat gcaggggcgt cctattgcca cgagtactca caacttcagt ggctcaaggt       780
cgggaaattc gagtggtgcg acaaaagata tcagaagcac tacgtgacat cacagattct       840
ggaaaccaag ggtgcaaatc accttttcgt attccagcgc ggcaatttcg ccaccccta       900
ctaccgaact ttcggggtag agacaaaatt tgtcacactc ccacccatat tcctcccaaa       960
gaaatacaac gcgcggtacc caataaagaa aactgtggca cagcaactat ttctctacat      1020
caagtcggtg aaaacagtca cggagagaga catttgggcc aaagtgagac agatcataaa      1080
gaccgctgag ctccaaagct actcggcgaa agaactcgca ctcattgtca actactactt      1140
gctcatctcc aagctggact ctgtcacctg ttttgacaat gtgcttacag ggggtgcgct      1200
caagaagctc ttcaaaccca ttgtggcttg gtggtccacc ttcaaaggcg cgcttttcgg      1260
gaaagaggag ttcgaacaac ttatggaagc gctcgagtgg gttgacgtgt cactgtccta      1320
caaagtggac acatacagcc aagctaaccc aaacaatcaa cccaaggtga tgttcgggta      1380
tgagtggctc agcacagaaa cgggagctcc aggaacagag gaggacgtcg cccccgagaa      1440
tccacaagag gacgaggatc cacatgaaaa gtacatccag gccctccaaa cactaacgaa      1500
ggccctcgat ccagagaacg ccccaccaca acagaaccaa gctcaaagct ccagcatcaa      1560
tgatccacaa caggagggagc atccccgctc acccccacgac ctccacactg atgaatcccc      1620
aagctgctca ggaagcttga attcttatgc ttgccactgc ccatgcggca ttgagctaaa      1680
aattttttca gccgagtttc cacccattcc cccactatcg cacggtgatc ggctaaaaaa      1740
tagggaagcc ttcttcttct caagagatgg cactccctac agctacactg ggggttccca      1800
cgtatccaga ggatggccgg ctttcctcga ccagatccta gccactgctg agttggtgag      1860
gcctatcccc catttcaacc agtgcctcat ccaaaaatac caaagggggcg cctccatccc      1920
cttccacagc gacgatgagc catgctacga tgtggaccac caagtgctca caatcaacct      1980
cactggcgaa gcggaattca aaactagctg caaagccggt tcagggagtt gcacgctggc      2040
agagaaccag tttcacctgt ccccccccagg tttccaaaag acgcataagc acagtgtggt      2100
ctcactcagc gcggggcgag tctccctcac atttcgctct accgtcaagc agggtgttac      2160
ctctgaagag ggcgattatg tagagcccga caatctgcca tggaaggcct ggctcgagaa      2220
attgagaaac ctgggattca ggggcacaca gctgcaatat gatccaaatg gagccttgat      2280
ctcaccaatc gaaagcatca agtcacttcc gaagtgctcc ccggaaaagg tcaaccccct      2340
```

```
cctcctcaag atgctgaatg atcaggctcg tgcaccaact ccattctcgc cgagccccat    2400
cagagcaaaa gcctactcct cagacgttaa gaactcccga attggcgcat tactccgaca    2460
gcagggcaag gactgggggcc accgtttcga ttcactcgtg gagaatgggc agagacagct   2520
agccatcagc gtgatccatg ggctggcgg ctctgggaaa tcgagggcgt tgcaaatgta    2580
cttaaaagac aatccagatg ctgatgtcac gatagtgttg ccaactaacg agcttaggct    2640
cgactggttg aagaaattac ccaccttccc agctgaccag atcaaaacct tcgagaaggc    2700
cttgctggcc cccataaaac ccacagtcat cttcgatgat tacggcaaac tgccggccgg    2760
gtacattgaa gccttctcgt gctacatgtc atcggttgaa cttctggtgc tcaccggtga    2820
ttctaagcaa agtgtgcacc atgagtctaa cgagaatgcg atgagcagcc tcattgaacc    2880
cttcaccctg gaagctgaca gtactcacg ctactatatt aatgccacac acagaaacaa    2940
gcgtgatttg gctaacaaac tagggggtcta ctcggaggtc acgggaataa catccatcac    3000
ccaaggcaac caccctgtgc cgggacttca cctgctcgtc ccctcactct acaagaagga    3060
agctttcagc gagatgggcc acaaggtttc cacttatgcg ggctgtcagg gtctcacagc    3120
cccacgcgtg caaattctgc tctcagaaga gactagcatg tgttcccgcg aagtcattta    3180
caccgccctc tcccgagccg ttcactccat tcactttgtc aactgcggcc caaacaatca    3240
ggctttctgg gccaagctgg agcacacc ttacctgaaa gctttcctct ccacgctccg    3300
agaagacgcg gcacctgtcg tgaaaccgaa agaggaagca ccagctccag ttgatccccc    3360
aaagacccac atcccagttg actcagccat gccaatttat gaggacttac tggatcagat    3420
gccggaaaag catgagaggg agatcttttc agaaaggcat gggcacagca attgcgtgca    3480 aacgaggat accttttgtgc aaatgttcag tcaccagcag gctaaggacg aaaccctcct    3540
ctgggctacc atcgaggcga gactggtcat ttccaaccc aaggccaatt ggcaagaatt    3600
catggagaaa agaccgattg gagatgtgct ctttgggttttc tacagagaag cgatggggct    3660
gcccactgaa cctattgcct ttgaaccaca gctttgggag tcttgcatcc atgaggtcca    3720
gcgtacctac ttggcaaagc ccatcaacat gctgaagaat ggacaggctc ggcaatcccc    3780
cgattatgat ccaaacatga tatctctctt tctgaagtcc cagtgggtga agaaaatgga    3840
gaagttgggc gccctaaaga tcaagcccgg acaaactatt gcctccttcc accaggccac    3900
tgtcatgctg ttcggcacga tggctaggta catgaggaga atgcgggaaa ttttccagcc    3960
taagaacatt gccatcaact gcgagatgac cccagaagat ctcacagatt gggccgtggg    4020
ttctgccggc cagtggaaat tcgccggccc ttctttagcc aatgacttca cagcattcga    4080
tcagtcacaa gatggggcga tgcttcagtt tgaggtcctc aaagccaaac accacagcat    4140
tccagaggat gtcttggacg cttacctaca catcaaaaca aactcgaaga tcttcttggg    4200
tacattgacc attatgagac tcacgggtga aggccccact ttcgatgcaa acactgagtg    4260
caacatcgct ttcacccatg caaaatttca gattccaaag ggtacagccc agctttacgc    4320
gggggatgac tcggcaattg atggcaaccc cccagtgaga gagagtttca gattggttga    4380
gcagaaattg aagctgaggt caaaaccggc gatcgcgatg caggaaaaag gagactgggc    4440
agaattctgt ggatacagga ttacgcccaa aggtttcatc aaggatccaa agaaacttca    4500
cgcgagtctg gtgcttgaaa agaagagagg taatttgaag aatgtgctga ggtcctatga    4560
gcttgacctg gccttggcat atcagcaccg ggatgaactt cacgaattac tctctgagga    4620
ggagctgcgt cttcactacg acacggttcg tacgctagtt aagtcaggtg gagggagaggt    4680 tttgaaaact tttcttccca aagatgaatc actttactaa cctcctcatt gaagagggtt    4740
```

```
acgtccggac gaacgaaatc ctctcagata ctctagtcgt ccatgctgta gctggcgctg    4800
gcaagtccac cctcatccgc aaattcatcc atcagcatcc acaggcccgc gcgtacaccc    4860
acggagtccc tgacccccca aatcttgaag gccgattcat tcaggctttt aagaaccctg    4920
acccaaacca cttcaacatc cttgacgagt attgtgcaga acctctaagc ggcagttgga    4980
acgtgctcat cgccgacccc ctgcaacata gatctcaagc tcttcgaccc cactacatca    5040
aaagagagtc ccacaggcta ggagtagcca cgtgtgaact tctcaccaga gtggggctcc    5100
cagttttgtc caacaagact gaggatcaag ttgattacca gggcattttc gaagggcccc    5160 tttttcggcac cgtgattgct ctggactcca ctgtcagagc cctcctcgta aagcacggaa    5220
ttccaccact ctgcccagct gaggtcctcg ggtctgagtt tgagcaaacg acagtagtct    5280
cggaggttcc gcttagccag gtcaagttca agcacgctct gtacatcgct ctcacccgcc    5340
acaagaagtc tctccatgtc cgggctcccc cactccctga cacccccgc cgattactct    5400 aagccagtgc ttgcagcagc agtaggagtt agtttagctt tagtaataaa ctctttcttg    5460
gtctataggc ttccctcgcc cggggacaat attcatcaac tgccctttgg aggttcctac    5520
cgggacggaa ctaagagcat ccactacaat tcgcctaggg cccagagtca gatctcaggt    5580
gcgtcaccgt tcctgataat cctgatactc tcagccctca tctatgccct atcttgtaga    5640
ggcggccatc accgtgctcg cttgcatagg tgtccttgct gctcttaggc cagggtccca    5700
tccttgcacc attctgctaa ctggacactc tgcgaccatt agcggaaact gcggacctgt    5760
cgcaccagag accatcaggg ctcttggaga ctacttaacc gggcttaggt tttagcatta    5820
gtttgattat cctattgtca tcctagttga agtcatcatg tctacaccat ttcctcaagt    5880
cactcaggaa cagatgaacg ccttcactcc acataccaca tccaatctcc ttccatcacc    5940
ggagcagttg accaccattg ccaacctctt ggttgctgcc aaggtgcctg ccgcctcaac    6000
cacgaccatc gccctggagc ttgttaactt ctgttatgac aatggctcca gtacctacac    6060
agcggtggtg ggcccttctt cacttgcaga ggtctcactc tcccaggtcg ctaacatcgt    6120
caaagcctca ggcacctctc tccgcaaatt ctgcagattc tttgctccaa tcatctggaa    6180
cctcagaaca gacaagacgc ccccagccaa ctgggaagcc aatgggttca aaccgacaga    6240
gaagtttgca gccttcgatt tcttcgatgg agtggagaat ccggcggcca tgcagccacc    6300
aggagggttg gttaggactc ccagccaagc agaaaggatc gccaacgcta ctaacaagca    6360
ggtaaacctc tttcaggccg cggcacagga taataacttc gccagcaact ctgcattcat    6420
caccaagggc caattgtcct ccaactcacc aaccattcaa tacctcccac cacctgagtg    6480
atttctccac ccagtccaag cccgttgttt tcgcaattt gttggggcta tcgagttttc    6540
aaaattgctt ccgcttctgt agacctaaat tacagcctag tgtgcggttt aatacctatt    6600
tacgcac                                                              6607
```

<210> SEQ ID NO 2
<211> LENGTH: 6607
<212> TYPE: DNA
<213> ORGANISM: Alternanthera mosaic virus

<400> SEQUENCE: 2

```
gaaaagtaaa gcaaagcaaa gcaaagcaaa ggaaccgaaa gtccatattt gcccttcgag      60
gagatcgatt acccatcccg gctagatcaa cagtatggcc cactttcgtt ccgttcttga     120
ccaaatgaat gaccccagcc ttcgggcggt catccaggaa gaagcttacc gcgaaataaa     180
gaaaaccatc gcggaaacca aacagtacaa cccttacgcc caggatccag cggcggctga     240
```

```
ctcattagaa aaattaggaa tagaatctaa cccccttctca gtccgcgctc atacacacgc      300
ggccgcgaag tcaatagaat tagacatgta caaaatcacg ggttactccc tcccgaagga      360
gaatccaatt actttccttt tcatgaagag gtccaaactt caatacttcc acagaggccc      420
acagcatgga gacttattcc ttaatgcttg tattgagcca aaggacgtca ccaggtacgc      480
cttagaagac ctctttaaac cctccacaac cccagaaatc caaaccagag tggcattcat      540
tggagacaca ctacacttcc ttcctctagg ggccatcaga gagatattta caagctcaca      600
aaagctccaa actctctatg caacaatggt actaccccc gaagccatgc acagaatgca       660
ctcaattcac cccagcatct acgagctaga attccatgaa aaaatttta tatacaagcc       720
gggaggacat gccggggcgt cttattgcca cgaatactca caacttcagt ggctcaaggt      780
cggaaaattt gagtggtgcg acaagaaata tcagaagcac tacgtgacat cacagattct      840
ggaaaccaag ggtgcaaatc accttttttgt gttccagcgc ggcaatttcg ccaccccctac      900
ctaccgaact ttcggggtag agacaaaatt tgtcacactc ccacccatat tcctcccaaa      960
gaaatacaac gcgcggtacc cgataaagaa aactgtggcg cagcagctat ttctttacat     1020
caagtccgtg aaaacagtca cggagagaga catctgggcc aaagttagac agatcataaa     1080
gaccgctgag ctccaaagct actcggcaaa agagctcgca ctcattgtca actactactt     1140
gctcatctct aagctggact cggtcacatg ttttgacaat gtgctcacag ggggtgtgct     1200
caagaagctc tttaaaccca tcgtggcttg gtggtccacc ttcaaaggga gatcttcgg      1260
gaaggaggag ttcgaacaac ttatggaggc gcttgagtgg gtcgacgtgt cactgtccta     1320
caaagtggag acatacagcc aggccaaccc aaacaatcag cccaaggtga tgttcgggta     1380
cgagtggctc agcacagaaa cgggaacccc aggaacagag gaggacgccg ctcccgaaac     1440
cccacaagag gacgaggacc cacatgaaag atatatccag gccctccaaa cactgacgaa     1500
ggccctcgac caggagagtg ctccaccacc aacagaacca gcccagtgct ccagcaccag     1560
taatccacaa caggaggagc acttccgccc accccacaac ctccacactg atgaaacccc     1620
aagctgctca ggaagctcga attcctttgc ttgccactgc ccgtgcggca cggaactcaa     1680
agttttctca gccgagtttc cacccattcc cccactatcg cacggcgatc ggctcaagaa     1740
cagggaagca ttcttctttt cgagagatgg tactccctac agctcactg ggggttccca      1800
cgcatccaga ggatggccga cttctcttga ccagatcctg gccactgctg agttggtgag     1860
gccccctccc cacttcaacc aatgcctcat ccaaaaatac caaagaggcg cctccatccc     1920
cttccacaga gacgacgagc catgctacga tgcggaccac caagtgctca caatcaacct     1980
caccggtgaa gcagaattca aaatcagctg caaagctggt tcagggagtt gcacgttagt     2040
agagaaccag ttccacctgt cccccccgg tttccaaaag acacacaagc acagtgtggt      2100
ctcacttagc gcgggggcgag tctccctcac attccgctcc actgtcaagc agagcgttac     2160
ctctgaagag ggtgactgtg tagaacccga caatctgccg tggaaggcct ggctcggaaa     2220
gctgagaaac ctgggcttca ggggcatgca gctgcaatac gatccaaatg gggccttgat     2280
ctcaccaatc gaaagcgtca agtcactccc gaagtgctcc ccggaaaagg tcgacccctc     2340
cctcctcaaa atgctagata atcaggctcg cgcaccaact ccattctcgc ccagccccat     2400
cagggcaaaa gcttactcct cagacgtcaa aaactctcga attggcgcat tactccgaca     2460
gcagggcaaa gattgggggcc accgcttcga ttcacttgtg gagaatgggc agaggcagct     2520
agccatcagt gtgatccatg gggccggtgg ctctgggaaa tcgagggcgt tgcagatgta     2580
cctgaaggac aacccagatg ctgatgtcac gatagtgcta ccaactaacg agctgaggct     2640
```

```
cgactggctg aagaagttgc ccaccttccc ggcagaccag atcaaaacct tcgagaaggc   2700
cctgctggct cccacaaagc ccacagttat cttcgatgac tacggcaaac tgccagccgg   2760
gtacattgaa tccttctcat tctacatgtc atcagctgag cttctggtgc tcaccggtga   2820
ctccaagcag agcgtgcatc acgagtctaa tgagaatgcg atgagcagcc tcatcgaacc   2880
cttcactctg gaagctgata agtactcacg ctattacatc aatgccacac acagaaacaa   2940
gcgtgatttg gccaacaagc tagggtctcta ctcagaggtc acggggataa catccatcac   3000
ccaaggcaac caccctgtgc cgggacttca cctgctcgtc ccctcactct acaagaagga   3060
ggctttcagc gaaatgggtc acaaggtttc cacttatgcg ggctgtcagg gcctcacagc   3120
cccacgcgtg caaattctgc tctcagaaga gactagcatg tgttcccgcg aagtcattta   3180
caccgccctc tcccgagccg ttcactccat tcactttgtc aactgcggcc caaacaatca   3240
ggctttctgg gccaagctgg agagcacacc ttacctgaaa gctttcctct ccacgctccg   3300
agaagacgcg gcacctgtcg tgaaaccgaa agaggaagca ccagctccag ttgatccccc   3360
aaagacccac atcccagttg actcagccat gccaatttat gaggacttac tggatcagat   3420
gcgggaaaag catgagaggg agatcttttc agaaaagcat gggcacagca attgcgtgca   3480
aacggaggat acctttgtgc aaatgttcag tcaccagcag gctaaggacg aaaccccttct   3540 ctgggctacc atcgaggcga gactggtcat ttccaacccc aaggccaatt ggcaagaatt   3600
catgagaaaa agaccgattg gagatgtgct ctttggtttc tacagagaag cgatggggct   3660
gcccactgaa cctattgcct ttgaaccaca gctttgggag tcttgcatcc atgaggtcca   3720
gcgtacctac ttggcaaagc ccatcaacat gctgaagaat ggacaggctc ggcaatcccc   3780
cgattatgat ccaaacatga tatctctctt tctgaagtcc cagtgggtga agaaaatgga   3840
gaagttgggc gccctaagga tcaagcccgg acaaactatt gcctccttcc accaggccac   3900
tgtcatgctg ttcggcacga tggctaggta catgaggaga atgcgggaaa tcttccagcc   3960
taagaacatt gccatcaact gcgagatgac cccagaagat ctcacagatt gggccgtggg   4020
ttctgccggc cagtggaaat tcgccggccc ttctttagcc aatgacttca cagcattcga   4080
tcagtcacaa gatggggcga tgcttcagtt tgaggtcctc aaagccaaac accacagcat   4140
tccagaggat gtcttggacg cttacctaca catcaaaaca aactcgaaga tcttcttggg   4200
tacattgacc attatgagac tcacgggtga gggccccact ttcgatgcaa acactgagtg   4260
caacatcgct ttcacccatg caaaatttca gattccaaag ggtacagccc agctttacgc   4320
gggggatgac tcggcaattg atggcaaccc cccagtgaga gagagcttca gattggttga   4380
gcagaaattg aagctgaggt caaaaccggc gatcgcgatg caggaaaaag gagactgggc   4440
agaattctgt ggatacagga ttacgcccaa aggtttcatc aaggatccaa agaaacttca   4500
cgcgagtctg gtgcttgaaa agaagagagg taatttgaag aatgtgctga ggtcctatga   4560
gcttgacctg gcattggcat atcagcaccg ggatgaactt cacgaattac tctctgagga   4620
ggagctgcgt cttcactacg acacggttcg tacgctagtt aagtcaggtg gaggagaggt   4680
tttgaaaact tttctttcca agatgaatc actttactaa cctcctcatt gaagagggtt   4740
acgtccggac gaacgaaatc ctctcagata ctctagtcgt ccatgctgta gctggcgctg   4800
gcaagtccac cctcatccgc aaattcatcc atcagcatcc acaggccgt gcgtacaccc    4860 acggagtccc tgaccccca aatctcgaag gccgattcat tcaggctttt aagaaccctg   4920
acccaaacca cttcaacatc cttgacgagt attgcgcaga acctccaagc ggcagttgga   4980
acgtgctcat cgccgacccc ctgcaacata gatctcaagc tcttcgaccc cactacatca   5040
```

```
aaagagagtc ccacaggcta ggagtagcca cgtgtgaact tctcaccaga gtggggcttc    5100
cagttttgtc caacaagact gaggatcaag tcgattacca gggcattttc gaagggcccc    5160
ttttcggcac cgtgattgct ctggactcca ctgtcagagc cctcctcgta aagcacggaa    5220
ttccaccact ctgccctgct gaggtcctcg ggtctgagtt tgagcaaacg acagtagtct    5280
cggaggttcc gcttagccag gtcaagttca agcacgctct gtacatcgct ctcacccgcc    5340
acaagaagtc tctccatgtc cgggctcccc cactccctga cacccccgc cgattactct     5400 aagccagtgc ttgcagcagc agtaggagtt agtttagctt tagtaataaa ctctttcttg    5460
gtctataggc ttccctcgcc cggggacaat attcatcaac tgcccttttgg aggttcctac   5520 cgggacggaa ctaagagcat ccactacaat tcgcctaggg cccagagtca gatctcaggt    5580
gcgtcaccgt tcctgataat cctgatactc tcagccctca tctatgccct atcttgtaga    5640
ggcggccatc accgtgctcg cttgcatagg tgtccttgct gctcttaggc cagggtccca    5700
tccttgcacc attctgctaa ctggacactc tgcgaccatt agcggaaact gtggacctgt    5760
cgcaccagag accatcaggg ctcttggaga ctacttaacc gggcttaggt tttagcatta    5820
gtttgattat cctatcgtca tcctagttga agtcatcatg tctacaccat tcctcaagt     5880 cactcaggaa cagatgaacg ccttcactcc ataccaca tccaatctcc ttccatcacc       5940
ggagcagttg accaccattg ccaacctctt ggttgctgcc aaggtgcctg ccgcctcaac    6000
cacgaccatt gccctggagc ttgttaactt ctgttatgac aatggctcca gtacttacac    6060
agcggtggtg ggcccttctt cacttgcaga ggtctcactc tcccaggtcg ctaacatcgt    6120
caaagcctca ggcacctctc tccgcaaatt ctgcagattc tttgctccaa tcatctggaa    6180
cctcagaaca gacaagacgc cccagccaa ctgggaagcc aatgggttca aaccgacaga     6240
gaagtttgca gccttcgatt tcttcgatgg agtggaaaat ccggcggcca tgcagccacc    6300
aggagggttg gttaggactc ccagccaagc agaaaggatc gccaacgcca ctaacaagca    6360
ggtaaacctc tttcaggccg cggcacagga taataacttc gccagcaact ctgcattcat    6420
caccaagggc caattgtcct ccaactcacc aaccattcaa tacctcccac cacctgagtg    6480
atttctccac ccagttcaag cccgttgttt tcgcaattt gttggggcta tcgagttttc    6540
aaaattgctt ccgcttctgt agacctaaat tacagcctag tgtgcggttt aatacctatt    6600
tacgcac                                                              6607
```

<210> SEQ ID NO 3
<211> LENGTH: 6607
<212> TYPE: DNA
<213> ORGANISM: Altemanthera mosaic virus

<400> SEQUENCE: 3

```
gaaaagtaaa gcaaagcaaa gcaaagcaaa ggaaccgaaa gtccatattt gcccttcgag      60
gagatcgatt acccatcccg gctagatcaa cagtatggcc cactttcgtt ccgttcttga     120
ccaaatgaat gaccccagcc ttcgggcggt catccaggaa gaagcttacc gcgaaataaa     180
gaaaaccatc gcggaaacca acagtacaa cccttacgcc caggatccag cggcggctga     240
ctcattagaa aaattaggaa tagaatctaa ccccttctca gtccgcgctc atacacacgc     300
ggccgcgaag tcaatagaat tagacatgta caaaatcacg ggttactccc tcccgaagga    360
gaatccaatt actttccttt tcatgaagag gtccaaactt caatacttcc acagaggccc    420
acagcatgga gacttattcc ttaatgcttg tattgagcca aaggacgtca ccaggtacgc    480
cttagaagac ctcttaaac cctccacaac cccagaaatc caaaccagag tggcattcat     540
```

```
tggagacaca ctacacttcc ttcctctagg ggccatcaga gagatattta caagctcaca        600
aaagctccaa actctctatg caacaatggt actacccccc gaagccatgc acagaatgca        660
ctcaattcac cccagcatct acgagctaga attccatgaa aaaaatttta tatacaagcc        720
gggaggacat gccggggcgt cttattgcca cgaatactca caacttcagt ggctcaaggt        780
cggaaaattt gagtggtgcg acaagaaata tcagaagcac tacgtgacat cacagattct        840
ggaaaccaag ggtgcaaatc acctttttgt gttccagcgc ggcaatttcg ccacccctac        900
ctaccgaact ttcggggtag agacaaaatt tgtcacactc ccacccatat tcctcccaaa        960
gaaatacaac gcgcggtacc cgataaagaa aactgtggcg cagcagctat ttctttacat       1020
caagtccgtg aaaacagtca cggagagaga catctgggcc aaagttagac agatcataaa       1080
gaccgctgag ctccaaagct actcggcaaa agagctcgca ctcattgtca actactactt       1140
gctcatctct aagctggact cggtcacatg ttttgacaat gtgctcacag ggggtgtgct       1200
caagaagctc tttaaaccca tcgtggcttg gtggtccacc ttcaaaggga agatcttcgg       1260
gaaggaggag ttcgaacaac ttatggaggc gcttgagtgg gtcgacgtgt cactgtccta       1320
caaagtggag acatacagcc aggccaaccc aaacaatcag cccaaggtga tgttcgggta       1380
cgagtggctc agcacagaaa cgggaacccc aggaacagag gaggacgccg ctcccgaaac       1440
cccacaagag gacgaggacc cacatgaaag atatatccag gccctccaaa cactgacgaa       1500
ggccctcgac caggagagtg ctccaccacc aacagaacca gcccagtgct ccagcaccag       1560
taatccacaa caggaggagc acttccgccc accccacaac ctccacactg atgaaacccc       1620
aagctgctca ggaagctcga attccttttgc ttgccactgc ccgtgcggca cggaactcaa       1680
agttttctca gccgagtttc cacccattcc cccactatcg cacggcgatc ggctcaagaa       1740
cagggaagca ttcttctttt cgagagatgg tactccctac agctacactg ggggttccca       1800
cgcatccaga ggatggccga ctttccttga ccagatcctg gccactgctg agttggtgag       1860
gcccctcccc cacttcaacc aatgcctcat ccaaaaatac aaagaggcg cctccatccc       1920 cttccacaga gacgacgagc catgctacga tgcggaccac caagtgctca caatcaacct       1980
caccggtgaa gcagaattca aaatcagctg caaagctggt tcagggagtt gcacgttagt       2040
agagaaccag ttccacctgt ccccccccgg tttccaaaag acacacaagc acagtgtggt       2100
ctcacttagc gcggggcgag tctccctcac attccgctcc actgtcaagc agagcgttac       2160
ctctgaagag ggtgactgtg tagaacccga caatctgccg tggaaggcct ggctcggaaa       2220
gctgagaaac ctgggcttca ggggcatgca gctgcaatac gatccaaatg gggccttgat       2280
ctcaccaatc gaaagcgtca agtcactccc gaagtgctcc ccggaaaagg tcgacccctc       2340
cctcctcaaa atgctagata tcaggctcg cgcaccaact ccattctcgc ccagccccat       2400
cagggcaaaa gcttactcct cagacgtcaa aaactctcga attggcgcat tactccgaca       2460
gcagggcaaa gattggggcc accgcttcga ttcacttgtg gagaatgggc agaggcagct       2520
agccatcagt gtgatccatg gggccggtgg ctctgggaaa tcgagggcgt tgcagatgta       2580
cctgaaggac aacccagatg ctgatgtcac gatagtgcta ccaactaacg agctgaggct       2640
cgactggctg aagaagttgc ccaccttccc ggcagaccag atcaaaacct tcgagaaggc       2700
cctgctggct cccacaaagc ccacagttat cttcgatgac tacggcaaac tgccagccgg       2760
gtacattgaa tccttctcat tctacatgtc atcagctgag cttctggtgc tcaccggtga       2820
ctccaagcag agcgtgcatc acgagtctaa tgagaatgcg atgagcagcc tcatcgaacc       2880
cttcactctg gaagctgata agtactcacg ctattacatc aatgccacac acagaaacaa       2940
```

```
gcgtgatttg gccaacaagc tagggtcta ctcagaggtc acggggataa catccatcac   3000
ccaaggcaac caccctgtgc cgggacttca cctgctcgtc ccctcactct acaagaagga   3060
ggctttcagc gaaatgggtc acaaggtttc acttatgcg ggctgtcagg gcctcacagc    3120
cccacgcgtg caaattctgc tctcagaaga gactagcatg tgttcccgcg aagtcattta   3180
caccgccctc tcccgagccg ttcactccat tcactttgtc aactgcggcc caaacaatca   3240
ggctttctgg gccaagctgg agagcacacc ttacctgaaa gctttcctct ccacgctccg   3300
agaagacgcg gcacctgtcg tgaaaccgaa agaggaagca ccagctccag ttgatccccc   3360
aaagacccac atcccagttg actcagccat gccaatttat gaggacttac tggatcagat   3420
gccggaaaag catgagaggg agatcttttc agaaaggcat gggcacagca attgcgtgca   3480
aacggaggat acctttgtgc aaatgttcag tcaccagcag gctaaggacg aaacccttct   3540
ctgggctacc atcgaggcga gactggtcat ttccaacccc aaggccaatt ggcaagaatt   3600
catggagaaa agaccgattg gagatgtgct ctttggtttc tacagagaag cgatgggct    3660 gcccactgaa cctattgcct ttgaaccaca gctttgggag tcttgcatcc atgaggtcca   3720
gcgtacctac ttggcaaagc ccatcaacat gctgaagaat ggacaggctc ggcaatcccc   3780
cgattatgat ccaaacatga tatctctctt tctgaagtcc cagtgggtga agaaaatgga   3840
gaagttgggc gccctaaaga tcaagcccgg acaaactatt gcctccttcc accaggccac   3900
tgtcatgctg ttcggcacga tggctaggta catgaggaga atgcgggaaa ttttccagcc   3960
taagaacatt gccatcaact gcgagatgac cccagaagat ctcacagatt gggccgtggg   4020
ttctgccggc cagtggaaat tcgccggccc ttctttagcc aatgacttca cagcattcga   4080
tcagtcacaa gatggggcga tgcttcagtt tgaggtcctc aaagccaaac accacagcat   4140
tccagaggat gtcttggacg cttacctaca catcaaaaca aactcgaaga tcttcttggg   4200
tacattgacc attatgagac tcacgggtga aggccccact ttcgatgcaa acactgagtg   4260
caacatcgct ttcacccatg caaaatttca gattccaaag ggtacagccc agctttacgc   4320
gggggatgac tcggcaattg atggcaaccc cccagtgaga gagagtttca gattggttga   4380
gcagaaattg aagctgaggt caaaaccggc gatcgcgatg caggaaaaag gagactgggc   4440
agaattctgt ggatacagga ttacgcccaa aggtttcatc aaggatccaa agaaacttca   4500
cgcgagtctg gtgcttgaaa agaagagagg taatttgaag aatgtgctga ggtcctatga   4560
gcttgacctg gccttggcat atcagcaccg ggatgaactt cacgaattac tctctgagga   4620
ggagctgcgt cttcactacg acacggttcg tacgctagtt aagtcaggtg gaggagaggt   4680
tttgaaaact tttcttccca agatgaatc actttactaa cctcctcatt gaagagggtt    4740
acgtccggac gaacgaaatc ctctcagata ctctagtcgt ccatgctgta gctggcgctg   4800
gcaagtccac cctcatccgc aaattcatcc atcagcatcc acaggcccgc gcgtacaccc   4860
acggagtccc tgacccccca aatcttgaag gccgattcat tcaggctttt aagaaccctg   4920
acccaaacca cttcaacatc cttgacgagt attgtgcaga acctctaagc ggcagttgga   4980
acgtgctcat cgccgacccc ctgcaacata gatctcaagc tcttcgaccc cactacatca   5040
aaagagagtc ccacaggcta ggagtagcca cgtgtgaact tctcaccaga gtggggctcc   5100
cagttttgtc caacaagact gaggatcaag ttgattacca gggcattttc gaagggcccc   5160
ttttcggcac cgtgattgct ctggactcca ctgtcagagc cctcctcgta agcacggaa    5220 ttccaccact ctgcccagct gaggtcctcg ggtctgagtt tgagcaaacg acagtagtct   5280
cggaggttcc gcttagccag gtcaagttca agcacgctct gtacatcgct ctcacccgcc   5340
```

```
acaagaagtc tctccatgtc cgggctcccc cactccctga cacccccgc cgattactct      5400 aagccagtgc ttgcagcagc agtaggagtt agtttagctt tagtaataaa ctctttcttg      5460
gtctataggc ttccctcgcc cggggacaat attcatcaac tgcccttttgg aggttcctac     5520 cgggacggaa ctaagagcat ccactacaat tcgcctaggg cccagagtca gatctcaggt      5580
gcgtcaccgt tcctgataat cctgatactc tcagccctca tctatgccct atcttgtaga      5640
ggcggccatc accgtgctcg cttgcatagg tgtccttgct gctcttaggc cagggtccca      5700
tccttgcacc attctgctaa ctggacactc tgcgaccatt agcggaaact gcggacctgt      5760
cgcaccagag accatcaggg ctcttggaga ctacttaacc gggcttaggt tttagcatta      5820
gtttgattat cctattgtca tcctagttga agtcatcatg tctacaccat ttcctcaagt      5880
cactcaggaa cagatgaacg ccttcactcc acataccaca tccaatctcc ttccatcacc      5940
ggagcagttg accaccattg ccaacctctt ggttgctgcc aaggtgcctg ccgcctcaac      6000
cacgaccatc gccctggagc ttgttaactt ctgttatgac aatggctcca gtacctacac      6060
agcggtggtg ggcccttctt cacttgcaga ggtctcactc tcccaggtcg ctaacatcgt      6120
caaagcctca ggcacctctc tccgcaaatt ctgcagattc tttgctccaa tcatctggaa      6180
cctcagaaca gacaagacgc ccccagccaa ctgggaagcc aatgggttca aaccgacaga      6240
gaagtttgca gccttcgatt tcttcgatgg agtggagaat ccggcggcca tgcagccacc      6300
aggagggttg gttaggactc cagccaagc agaaaggatc gccaacgcta ctaacaagca      6360
ggtaaacctc tttcaggccg cggcacagga taataacttc gccagcaact ctgcattcat      6420
caccaagggc caattgtcct ccaactcacc aaccattcaa tacctcccac cacctgagtg      6480
atttctccac ccagtccaag cccgttgttt tcgcaatttt gttggggcta tcgagttttc      6540
aaaattgctt ccgcttctgt agacctaaat tacagcctag tgtgcggttt aatacctatt      6600
tacgcac                                                              6607

<210> SEQ ID NO 4
<211> LENGTH: 6607
<212> TYPE: DNA
<213> ORGANISM: Altemanthera mosaic virus

<400> SEQUENCE: 4
gaaaagtaaa gcaaagcaaa gcaaagcaaa gaaactgaaa gtctatattt gcccttcgag       60
gagatcgatt acccatcccg gctagatcaa cagtatggca cactttcgtt ctgttcttga      120
ccaaatgaac gatcccagcc tccgggcggt cattcaagaa gaagcttacc gcgaaattaa      180
aaaaaccatc gcggaaacca aacagtacaa tccttacgcc caggatccag cggcggctga      240
ctcattagag aaattaggaa tagaatctaa ccccttctca gtccgcgccc atacacacgc      300
ggccgcgaag tctatagaat tagacatgta caaaatcacg ggttactccc tcccaaagga      360
gaatccaatt acttttcttt tcatgaagag gtccaaactt caatacttcc acagaggacc      420
acagcatgga gacttgttcc ttaacgcttg gattgagcca aaggacgtca ccaggtacaa      480
cttagaagac ctcttcaaac cttccatcac cccagaaatc caaactagag tggcattcat      540
tggagacaca ctacacttcc ttcccctagg ggctatcaga gagatattta caagctccca      600
aaaacttcaa actctctatg caacaatggt actgccccc gaagccatgc acagaatgca      660
ctcaattcac cccagcattt acgagctaga attccatgaa agaaatttca tatacaagcc      720
gggaggacat gcagggcgt cctattgcca cgagtactca caacttcagt ggctcaaggt      780
cgggaaattc gagtggtgcg acaaaagata tcagaagcac tacgtgacat cacagattct      840
```

```
ggaaaccaag ggtgcaaatc accttttcgt attccagcgc ggcaatttcg ccaccCctac    900
ctaccgaact ttcggggtag agacaaaatt tgtcacactc ccacccatat tcctcccaaa    960
gaaatacaac gcgcggtacc caataaagaa aactgtggca cagcaactat ttctctacat   1020
caagtcggtg aaaacagtca cggagagaga catttgggcc aaagtgagac agatcataaa   1080
gaccgctgag ctccaaagct actcggcgaa agaactcgca ctcattgtca actactactt   1140
gctcatctcc aagctggact ctgtcacctg ttttgacaat gtgcttacag ggggtgcgct   1200
caagaagctc ttcaaaccca ttgtggcttg gtggtccacc ttcaaaggcg cgcttttcgg   1260
gaaagaggag ttcgaacaac ttatggaagc gctcgagtgg gttgacgtgt cactgtccta   1320
caaagtggag acatacagcc aagctaaccc aaacaatcaa cccaaggtga tgttcgggta   1380
tgagtggctc agcacagaaa cgggagctcc aggaacagag gaggacgtcg cccccgagaa   1440
tccacaagag gacgaggatc cacatgaaaa gtacatccag gccctccaaa cactaacgaa   1500
ggccctcgat ccagagaacg ccccaccaca aacagaacca gctcaaagct ccagcatcaa   1560
tgatccacaa caggaggagc atccccgctc accccacgac ctccacactg atgaatcccc   1620
aagctgctca ggaagcttga attcttatgc ttgccactgc ccatgcggca ttgagctaaa   1680
aattttttca gccgagtttc cacccattcc cccactatcg cacggtgatc ggctaaaaaa   1740
tagggaagcc ttcttcttct caagagatgg cactccctac agctacactg ggggttccca   1800
cgtatccaga ggatggccgg cttcctcga ccagatccta gccactgctg agttggtgag   1860
gcctatcccc catttcaacc agtgcctcat ccaaaaatac caaggggcg cctccatccc   1920 cttccacagc gacgatgagc catgctacga tgtggaccac caagtgctca caatcaacct   1980
cactggcgaa gcggaattca aaactagctg caaagccggt tcagggagtt gcacgctggc   2040
agagaaccag tttcacctgt ccccccagg tttccaaaag acgcataagc acagtgtggt   2100
ctcactcagc gcgggggcgag tctccctcac atttcgctct accgtcaagc agggtgttac   2160
ctctgaagag ggcgattatg tagagcccga caatctgcca tggaaggcct ggctcgagaa   2220
attgagaaac ctgggattca ggggcacaca gctgcaatat gatccaaatg gagccttgat   2280
ctcaccaatc gaaagcatca agtcacttcc gaagtgctcc ccggaaaagg tcaacccctc   2340
cctcctcaag atgctgaatg atcaggctcg tgcaccaact ccattctcgc cgagccccat   2400
cagagcaaaa gcctactcct cagacgttaa gaactcccga attggcgcat tactccgaca   2460
gcagggcaag gactgggggcc accgtttcga ttcactcgtg gagaatgggc agagacagct   2520
agccatcagc gtgatccatg gggctggcgg ctctgggaaa tcgagggcgt tgcaaatgta   2580
cttaaaagac aatccagatg ctgatgtcac gatagtgttg ccaactaacg agcttaggct   2640
cgactggttg aagaaattac ccaccttccc agctgaccag atcaaaacct tcgagaaggc   2700
cttgctggcc cccataaaac ccacagtcat cttcgatgat tacggcaaac tgccggccgg   2760
gtacattgaa gccttctcgt gctacatgtc atcggttgaa cttctggtgc tcaccggtga   2820
ttctaagcaa agtgtgcacc atgagtctaa cgagaatgcg atgagcagcc tcattgaacc   2880
cttcaccctg gaagctgaca agtactcacg ctactatatt aatgccacac acagaaacaa   2940
gcgtgatttg gctaacaaac taggggtcta ctcggaggtc acgggaataa catccatcac   3000
ccaaggcaac caccctgtgc cgggacttca cctgctcgtc ccctcactct acaagaagga   3060
agctttcagc gagatgggcc acaaggtttc cacttatgcg ggctgtcagg gtctcacagc   3120
cccacgcgtg caaattctgc tctcagaaga gactagcatg tgttcccgcg aagtcatta   3180 caccgcccctc tcccgagccg ttcactccat tcactttgtc aactgcggcc caaacaatca   3240
```

```
ggctttctgg gccaagctgg agagcacacc ttacctgaaa gctttcctct ccacgctccg    3300
agaagacgcg gcacctgtcg tgaaaccgaa agaggaagca ccagctccag ttgatccccc    3360
aaagacccac atcccagttg actcagccat gccaatttat gaggacttac tggatcagat    3420
gcgggaaaag catgagaggg agatcttttc agaaaagcat gggcacagca attgcgtgca    3480
aacggaggat accttttgtgc aaatgttcag tcaccagcag gctaaggacg aaacccttct    3540
ctgggctacc atcgaggcga gactggtcat ttccaacccc aaggccaatt ggcaagaatt    3600
catgagaaaa agaccgattg agatgtgct ctttggttc tacagagaag cgatggggct    3660
gcccactgaa cctattgcct ttgaaccaca gctttgggag tcttgcatcc atgaggtcca    3720
gcgtacctac ttggcaaagc ccatcaacat gctgaagaat ggacaggctc ggcaatcccc    3780
cgattatgat ccaaacatga tatctctctt tctgaagtcc cagtgggtga agaaaatgga    3840
gaagttgggc gccctaagga tcaagcccgg acaaactatt gcctccttcc accaggccac    3900
tgtcatgctg ttcggcacga tggctaggta catgaggaga atgcgggaaa tcttccagcc    3960
taagaacatt gccatcaact gcgagatgac cccagaagat ctcacagatt gggccgtggg    4020
ttctgccggc cagtggaaat cgccggccc ttctttagcc aatgacttca cagcattcga    4080
tcagtcacaa gatggggcga tgcttcagtt tgaggtcctc aaagccaaac accacagcat    4140
tccagaggat gtcttggacg cttacctaca catcaaaaca aactcgaaga tcttcttggg    4200
tacattgacc attatgagac tcacgggtga gggccccact ttcgatgcaa acactgagtg    4260
caacatcgct ttcacccatg caaaatttca gattccaaag ggtacagccc agctttacgc    4320 ggggatgac tcggcaattg atggcaaccc cccagtgaga gagagcttca gattggttga    4380
gcagaaattg aagctgaggt caaaaccggc gatcgcgatg caggaaaaag agactgggc    4440 agaattctgt ggatacagga ttacgcccaa aggtttcatc aaggatccaa agaaacttca    4500
cgcgagtctg gtgcttgaaa agaagagagg taatttgaag aatgtgctga ggtcctatga    4560
gcttgacctg gcattggcat atcagcaccg ggatgaactt cacgaattac tctctgagga    4620
ggagctgcgt cttcactacg acacggttcg tacgctagtt aagtcaggtg aggagaggt    4680 tttgaaaact tttctttcca agatgaatc actttactaa cctcctcatt gaagagggtt    4740
acgtccggac gaacgaaatc ctctcagata ctctagtcgt ccatgctgta gctggcgctg    4800
gcaagtccac cctcatccgc aaattcatcc atcagcatcc acaggcccgt gcgtacaccc    4860
acggagtccc tgacccccca aatctcgaag gccgattcat tcaggctttt aagaaccctg    4920
acccaaacca cttcaacatc cttgacgagt attgcgcaga acctccaagc ggcagttgga    4980
acgtgctcat cgccgacccc ctgcaacata gatctcaagc tcttcgaccc cactacatca    5040
aaagagagtc ccacaggcta ggagtagcca cgtgtgaact tctcaccaga gtggggcttc    5100
cagttttgtc caacaagact gaggatcaag tcgattacca gggcatttc gaagggcccc    5160 ttttcggcac cgtgattgct ctggactcca ctgtcagagc cctcctcgta aagcacggaa    5220
ttccaccact ctgccctgct gaggtcctcg ggtctgagtt tgagcaaacg acagtagtct    5280
cggaggttcc gcttagccag gtcaagttca agcacgctct gtacatcgct ctcacccgcc    5340
acaagaagtc tctccatgtc cgggctcccc cactccctga cacccccgc cgattactct    5400 aagccagtgc ttgcagcagc agtaggagtt agtttagctt tagtaataaa ctctttcttg    5460
gtctataggc ttccctcgcc cggggacaat attcatcaac tgccctttgg aggttcctac    5520
cgggacggaa ctaagagcat ccactacaat tcgcctaggg cccagagtca gatctccaggt    5580 gcgtcaccgt tcctgataat cctgatactc tcagccctca tctatgccct atcttgtaga    5640
```

```
ggcggccatc accgtgctcg cttgcatagg tgtccttgct gctcttaggc cagggtccca    5700
tccttgcacc attctgctaa ctggacactc tgcgaccatt agcggaaact gtggacctgt    5760
cgcaccagag accatcaggg ctcttggaga ctacttaacc gggcttaggt tttagcatta    5820
gtttgattat cctatcgtca tcctagttga agtcatcatg tctacaccat tccctcaagt    5880
cactcaggaa cagatgaacg ccttcactcc atacaccaca tccaatctcc ttccatcacc    5940
ggagcagttg accaccattg ccaacctctt ggttgctgcc aaggtgcctg ccgcctcaac    6000
cacgaccatt gccctggagc ttgttaactt ctgttatgac aatggctcca gtacttacac    6060
agcggtggtg ggcccttctt cacttgcaga ggtctcactc tcccaggtcg ctaacatcgt    6120
caaagcctca ggcacctctc tccgcaaatt ctgcagattc tttgctccaa tcatctggaa    6180
cctcagaaca gacaagacgc ccccagccaa ctgggaagcc aatgggttca aaccgacaga    6240
gaagtttgca gccttcgatt tcttcgatgg agtggaaaat ccggcggcca tgcagccacc    6300
aggagggttg gttaggactc ccagccaagc agaaggatc gccaacgcca ctaacaagca    6360
ggtaaacctc tttcaggccg cggcacagga taataacttc gccagcaact ctgcattcat    6420
caccaagggc caattgtcct ccaactcacc aaccattcaa tacctcccac cacctgagtg    6480
atttctccac ccagttcaag cccgttgttt tcgcaatttt gttggggcta tcgagttttc    6540
aaaattgctt ccgcttctgt agacctaaat tacagcctag tgtgcggttt aatacctatt    6600
tacgcac                                                             6607

<210> SEQ ID NO 5
<211> LENGTH: 748
<212> TYPE: DNA
<213> ORGANISM: Altemanthera mosaic virus-Portulaca

<400> SEQUENCE: 5
atgtccactc catttcctca agtcacccag gaacagatag acgctttcac cccacatacc     60
acatccaatc tccttccatc accggagcag ttgaccacca ttgctagtct cctggttgct    120
gccaaggtgc ctgccgcctc aaccacaacc attgccttgg aacttgtcaa cttttgttat    180
gacaatggct ccagtgccta cacagtggtg gtgggccctt cttcaatctc agggtgtca    240 ctctcccagg ttgctaacat cgtcaaagcc tcaggcacct ctctccgcaa attctgcaga    300
ttctttgccc caattatttg gaacctcaga acagacaaga cacccccagc taactgggaa    360
gctaatgggt tcaaacctac agagaagttt gcagccttcg atttcttcga cggagtggag    420
aatccggcgg ccatgcagcc accaggaggg ttggttaggg ctcccagcca agcagagaga    480
atcgccaacg ccaccaacaa gcaggtgaac ctctttcagg ccgcggcaca ggacaacaac    540
ttcgccagca actctgcatt catcaccaag ggccaactgt cctccaactc accaactatt    600
caatacctcc caccaccgga gtgatttctc cacccagtcc aagcccgttg ttttcgcaat    660
tttgttgggg ctattgagtt tcaaaattg ctttcgcttc tgtagaccta aattacagcc    720
tagtttgcgg tttaatacct atttacgc                                      748

<210> SEQ ID NO 6
<211> LENGTH: 41
<212> TYPE: DNA
<213> ORGANISM: Artificial Sequence
<220> FEATURE:
<223> OTHER INFORMATION: Chemically Synthesized

<400> SEQUENCE: 6
ctgcagtaat acgactcact atagaaaagt aaagcaaagc a                         41
```

<210> SEQ ID NO 7
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 7
agagcagaat ttgcacgcgt ggggctg                               27

<210> SEQ ID NO 8
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 8
cagccccacg cgtgcaaatt ctgctctca                             29

<210> SEQ ID NO 9
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 9
gagagtctag atttttttttt tttttttttt t                         31

<210> SEQ ID NO 10
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 10
aatccttgcc ctgctgtc                                         18

<210> SEQ ID NO 11
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 11
tcagaagcac tatgtgacat                                       20

<210> SEQ ID NO 12
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 12
ggagttctgt ggatacagga ttacgccca                             29

<210> SEQ ID NO 13
<211> LENGTH: 23
<212> TYPE: DNA
<213> ORGANISM: Artificial Sequence
<220> FEATURE:
<223> OTHER INFORMATION: Chemically Synthesized

```
<400> SEQUENCE: 13
ttcatctttg gaagaaaagt ttt                                              23

<210> SEQ ID NO 14
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 14
cccaaagatg aatcacttta ct                                               22

<210> SEQ ID NO 15
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 15
tagggacctc caaagggcag ttgatgaata tt                                    32

<210> SEQ ID NO 16
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 16
atcatctgga acctcagaac agac                                             24

<210> SEQ ID NO 17
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 17
tgaaagaggt ttacctgctt gttag                                            25

<210> SEQ ID NO 18
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 18
aagaggtcca aacttcaata cttcc                                            25

<210> SEQ ID NO 19
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 19
gaaggaagtg tagtgtgtct ccaat                                            25

<210> SEQ ID NO 20
<211> LENGTH: 25
```

```
<212> TYPE: DNA
<213> ORGANISM: Artificial Sequence
<220> FEATURE:
<223> OTHER INFORMATION: Chemically Synthesized

<400> SEQUENCE: 20
gttggcttac attgctcttg actat                                           25

<210> SEQ ID NO 21
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 21
gtttccgtac agatcctttc tgat                                            24

<210> SEQ ID NO 22
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 22
cccccacgaa gcccacagtc atc                                             23

<210> SEQ ID NO 23
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 23
catttgcaca aagtatcct c                                                21

<210> SEQ ID NO 24
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 24
gagaagcttt ccctcgcccg gggacaatat t                                    31

<210> SEQ ID NO 25
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 25
catagatcta cgcgtggatc ccatgggatg acttcaacta gga                       43

<210> SEQ ID NO 26
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 26
gggatccacg cgtagatcta tgctagcatg tctacaccat ttcct                     45
```

-continued

<210> SEQ ID NO 27
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 27
gctagccacc agagaccatc aggg                                          24

<210> SEQ ID NO 28
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 28
tctagatttt ttttttttt ttt                                            23

<210> SEQ ID NO 29
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 29
gagaaccatg ggtaaaggag aagaactttt                                    30

<210> SEQ ID NO 30
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 30
aaaaagatta gtcttcacca tggacgcgt                                     29

<210> SEQ ID NO 31
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 31
gagaaccatg gcctcctccg agaacgtcat                                    30

<210> SEQ ID NO 32
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 32
gactagctag cttatctcag gaacaggt                                      28

<210> SEQ ID NO 33
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 33
aaaaactagt actagcataa ccccttgggg                               30

<210> SEQ ID NO 34
<211> LENGTH: 44
<212> TYPE: DNA
<213> ORGANISM: Artificial Sequence
<220> FEATURE:
<223> OTHER INFORMATION: Chemically Synthesized

<400> SEQUENCE: 34
gagctgcagt aatacgactc actatagaaa agtaaagcaa agca               44

<210> SEQ ID NO 35
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 35
gagactagtt aagtaaagtg attcatcttt g                             31

<210> SEQ ID NO 36
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 36
agtatactcc ggacaacacc acaagg                                   26

<210> SEQ ID NO 37
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 37
tgttgtccgg agtatactca tcgaggat                                 28

<210> SEQ ID NO 38
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 38
taatgcacag attttcctag gcacgttatc                               30

<210> SEQ ID NO 39
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 39
actagttttt tttttttat ttatattatt cat                            33

<210> SEQ ID NO 40
<211> LENGTH: 25

```
<212> TYPE: DNA
<213> ORGANISM: Artificial Sequence
<220> FEATURE:
<223> OTHER INFORMATION: Chemically Synthesized

<400> SEQUENCE: 40
gcgccccaac cgctcaaggg ctctt                                    25

<210> SEQ ID NO 41
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 41
cttgggcggt tggggcgctg cgtat                                    25

<210> SEQ ID NO 42
<211> LENGTH: 37
<212> TYPE: DNA
<213> ORGANISM: Artificial Sequence
<220> FEATURE:
<223> OTHER INFORMATION: Chemically Synthesized

<400> SEQUENCE: 42
gagactcgag aaatggacgc aattatttca acactga                       37

<210> SEQ ID NO 43
<211> LENGTH: 34
<212> TYPE: DNA
<213> ORGANISM: Artificial Sequence
<220> FEATURE:
<223> OTHER INFORMATION: Chemically Synthesized

<400> SEQUENCE: 43
gagaggatcc tcagtaggtg ggggtgaggt ggtg                          34

<210> SEQ ID NO 44
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 44
ctgcagtaat acgactcact atag                                     24

<210> SEQ ID NO 45
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 45
gagagtctag atttttttttt tttttttttt t                            31

<210> SEQ ID NO 46
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 46
gagccatggc catgtccact ccatttcctc aagtc                         35
```

<210> SEQ ID NO 47
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 47
atgtccgggc tcccccactc cctga                                            25

<210> SEQ ID NO 48
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 48
gtctatctgt tcctgggtga cttg                                             24

<210> SEQ ID NO 49
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 49
gaacagatag acgccttcac ccc                                              23

<210> SEQ ID NO 50
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 50
ggcactggag ccattgtcat aac                                              23

<210> SEQ ID NO 51
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 51
ggctccagtg cctacacagc ggt                                              23

<210> SEQ ID NO 52
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 52
gagattgaag aagggcccac cacc                                             24

<210> SEQ ID NO 53
<211> LENGTH: 23
<212> TYPE: DNA
<213> ORGANISM: Artificial Sequence
<220> FEATURE:
<223> OTHER INFORMATION: Chemically Synthesized -continued

<400> SEQUENCE: 53
cccttcttca atctcagagg tct                                           23

<210> SEQ ID NO 54
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 54
gagccctaac caaccctcct ggtgg                                         25

<210> SEQ ID NO 55
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 55
ttggttaggg ctcccagcca agcag                                         25

<210> SEQ ID NO 56
<211> LENGTH: 34
<212> TYPE: DNA
<213> ORGANISM: Artificial Sequence
<220> FEATURE:
<223> OTHER INFORMATION: Chemically Synthesized

<400> SEQUENCE: 56
gagactcgag aaatgaatca ctttactaac ctca                               34

<210> SEQ ID NO 57
<211> LENGTH: 34
<212> TYPE: DNA
<213> ORGANISM: Artificial Sequence
<220> FEATURE:
<223> OTHER INFORMATION: Chemically Synthesized

<400> SEQUENCE: 57
gagaggatcc tttattacta aagctaaact aact                               34

<210> SEQ ID NO 58
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 58
gagactcgag aaatgtccgg gctcccccca                                    29

<210> SEQ ID NO 59
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 59
ggatccctaa gagcagcaag ga                                            22

<210> SEQ ID NO 60
<211> LENGTH: 26

```
<212> TYPE: DNA
<213> ORGANISM: Artificial Sequence
<220> FEATURE:
<223> OTHER INFORMATION: Chemically Synthesized

<400> SEQUENCE: 60
ctcgagaaat gccctatctt gtagag                                          26

<210> SEQ ID NO 61
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 61
ggatccctaa aacctaagcc aaagcagag                                       29

<210> SEQ ID NO 62
<211> LENGTH: 39
<212> TYPE: DNA
<213> ORGANISM: Artificial Sequence
<220> FEATURE:
<223> OTHER INFORMATION: Chemically Synthesized

<400> SEQUENCE: 62
gatctcgaga aatgtttttc cgtggttgga aaaaggtgt                            39

<210> SEQ ID NO 63
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 63
gagcccgggt agaatttcat ctcactctg                                       29

<210> SEQ ID NO 64
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 64
gagactcgag atatgtctac accatttcct                                      30

<210> SEQ ID NO 65
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 65
gagaggatcc tcactcaggt cctgggag                                        28

<210> SEQ ID NO 66
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 66
atcgaattca tgtctacacc atttcctcaa                                      30
```

<210> SEQ ID NO 67
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 67
gagaggatcc tcactcaggt cctgggag                                         28

<210> SEQ ID NO 68
<211> LENGTH: 226
<212> TYPE: PRT
<213> ORGANISM: Artificial Sequence
<220> FEATURE:
<223> OTHER INFORMATION: Chemically Synthesized

<400> SEQUENCE: 68

Met Asp Ile Leu Ile Ser Ser Leu Lys Ser Leu Gly Tyr Ser Arg Thr
1               5                   10                  15

Ser Lys Ser Leu Asp Ser Gly Pro Leu Val His Ala Val Ala Gly
            20                  25                  30

Ala Gly Lys Ser Thr Ala Leu Arg Lys Leu Ile Leu Arg His Pro Thr
        35                  40                  45

Phe Thr Val His Thr Leu Gly Val Pro Asp Lys Val Ser Ile Arg Thr
    50                  55                  60

Arg Gly Ile Gln Lys Pro Gly Pro Ile Pro Glu Gly Asn Phe Ala Ile
65                  70                  75                  80

Leu Asp Glu Tyr Thr Leu Asp Asn Thr Thr Arg Asn Ser Asn Gln Ala
                85                  90                  95

Leu Phe Ala Asp Pro Tyr Gln Ala Pro Glu Phe Ser Leu Glu Pro His
            100                 105                 110

Phe Tyr Leu Glu Thr Ser Phe Arg Val Pro Arg Lys Val Ala Asp Leu
        115                 120                 125

Ile Ala Gly Cys Gly Phe Asp Phe Glu Thr Asn Ser Pro Glu Glu Gly
    130                 135                 140

His Leu Glu Ile Thr Gly Ile Phe Lys Gly Pro Leu Leu Gly Lys Val
145                 150                 155                 160

Ile Ala Ile Asp Glu Glu Ser Glu Thr Thr Leu Ser Arg His Gly Val
                165                 170                 175

Glu Phe Val Lys Pro Cys Gln Val Thr Gly Leu Glu Phe Lys Val Val
            180                 185                 190

Thr Ile Val Ser Ala Ala Pro Ile Glu Glu Ile Gly Gln Ser Thr Ala
        195                 200                 205

Phe Tyr Asn Ala Ile Thr Arg Ser Lys Gly Leu Thr Tyr Val Arg Ala
    210                 215                 220

Gly Pro
225

<210> SEQ ID NO 69
<211> LENGTH: 232
<212> TYPE: PRT
<213> ORGANISM: Artificial Sequence
<220> FEATURE:
<223> OTHER INFORMATION: Chemically Synthesized

<400> SEQUENCE: 69

Met Asn His Phe Thr Asn Leu Leu Ile Glu Glu Gly Tyr Val Arg Thr
1               5                   10                  15

```
Asn Glu Ile Leu Ser Asp Thr Leu Val His Ala Val Gly Ala
            20                  25                  30

Gly Lys Ser Thr Leu Ile Arg Lys Phe Ile His Gln His Pro Gln Ala
        35                  40                  45

Arg Ala Tyr Thr His Gly Val Pro Asp Pro Asn Leu Glu Gly Arg
    50                  55                  60

Phe Ile Gln Ala Phe Lys Asn Pro Asp Pro Asn His Phe Asn Ile Leu
65                  70                  75                  80

Asp Glu Tyr Cys Ala Glu Pro Pro Ser Gly Ser Trp Asn Val Leu Ile
                85                  90                  95

Ala Asp Pro Leu Gln His Arg Ser Gln Ala Leu Arg Pro His Tyr Ile
            100                 105                 110

Lys Arg Glu Ser His Arg Leu Gly Val Ala Thr Cys Glu Leu Leu Thr
        115                 120                 125

Arg Val Gly Leu Pro Val Leu Ser Asn Lys Thr Glu Asp Gln Val Asp
    130                 135                 140

Tyr Gln Gly Ile Phe Glu Gly Pro Leu Phe Gly Thr Val Ile Ala Leu
145                 150                 155                 160

Asp Ser Thr Val Arg Ala Leu Leu Val Lys His Gly Ile Pro Pro Leu
                165                 170                 175

Cys Pro Ala Glu Val Leu Gly Ser Glu Phe Glu Gln Thr Thr Val Val
            180                 185                 190

Ser Glu Val Pro Leu Ser Gln Val Lys Phe Lys His Ala Leu Tyr Ile
        195                 200                 205

Ala Leu Thr Arg His Lys Lys Ser Leu His Val Arg Ala Pro Pro Leu
    210                 215                 220

Pro Asp Thr Pro Arg Arg Leu Leu
225                 230

<210> SEQ ID NO 70
<211> LENGTH: 56
<212> TYPE: PRT
<213> ORGANISM: Artificial Sequence
<220> FEATURE:
<223> OTHER INFORMATION: Chemically Synthesized

<400> SEQUENCE: 70

Thr Ala Gly Val Pro Gln Asn Pro Thr Leu Asp Gly Ala Tyr Ile Arg
1               5                   10                  15

Lys Leu Thr Ile Pro Glu Ser Asn Lys Leu Asn Ile Leu Asp Glu Tyr
            20                  25                  30

Ala Ala Leu His Pro Leu Lys Gly Ser Trp Asp Val Val Cys Ala Asp
        35                  40                  45

Pro Leu Gln His Pro Asn Thr Ala
    50                  55

<210> SEQ ID NO 71
<211> LENGTH: 56
<212> TYPE: PRT
<213> ORGANISM: Artificial Sequence
<220> FEATURE:
<223> OTHER INFORMATION: Chemically Synthesized

<400> SEQUENCE: 71

Thr Ala Gly Thr Pro Gln Ser Pro Asn Leu Thr Gly Ala Phe Ile Arg
1               5                   10                  15

Lys Leu Thr Cys Pro Glu Ser Asn Lys Ile Asn Leu Leu Asp Glu Tyr
            20                  25                  30
```

Ala Ala Leu Gln Pro Leu Lys Gly Ser Trp Asp Val Val Leu Ala Asp
        35                  40                  45

Pro Leu Gln His Thr Gly Leu Thr
        50                  55

<210> SEQ ID NO 72
<211> LENGTH: 55
<212> TYPE: PRT
<213> ORGANISM: Artificial Sequence
<220> FEATURE:
<223> OTHER INFORMATION: Chemically Synthesized

<400> SEQUENCE: 72

Thr Leu Gly Thr Pro Asp Lys Pro Asn Leu Thr Arg Lys Met Ile Arg
1               5                   10                  15

Glu Tyr Ser Met Pro Lys Ala Asn His Phe Asn Val Leu Asp Glu Tyr
                20                  25                  30

Cys Ala Gln Pro Leu Lys Gly Ser Trp Asp Ala Val Phe Ala Asp Pro
        35                  40                  45

Leu Gln His Pro Asp Phe Thr
        50                  55

<210> SEQ ID NO 73
<211> LENGTH: 55
<212> TYPE: PRT
<213> ORGANISM: Artificial Sequence
<220> FEATURE:
<223> OTHER INFORMATION: Chemically Synthesized

<400> SEQUENCE: 73

Thr His Gly Val Pro Asp Pro Pro Asn Leu Glu Gly Arg Phe Ile Gln
1               5                   10                  15

Ala Phe Lys Asn Pro Asp Pro Asn His Phe Asn Ile Leu Asp Glu Tyr
                20                  25                  30

Cys Ala Glu Pro Pro Ser Gly Ser Trp Asn Val Leu Ile Ala Asp Pro
        35                  40                  45

Leu Gln His Arg Ser Gln Ala
        50                  55

<210> SEQ ID NO 74
<211> LENGTH: 55
<212> TYPE: PRT
<213> ORGANISM: Artificial Sequence
<220> FEATURE:
<223> OTHER INFORMATION: Chemically Synthesized

<400> SEQUENCE: 74

Thr His Gly Val Pro Asp Pro Pro Asn Leu Glu Gly Arg Phe Ile Gln
1               5                   10                  15

Ala Phe Lys Asn Pro Asp Pro Asn His Phe Asn Ile Leu Asp Glu Tyr
                20                  25                  30

Cys Ala Glu Pro Leu Ser Gly Ser Trp Asn Val Leu Ile Ala Asp Pro
        35                  40                  45

Leu Gln His Arg Ser Gln Ala
        50                  55

<210> SEQ ID NO 75
<211> LENGTH: 55
<212> TYPE: PRT
<213> ORGANISM: Artificial Sequence
<220> FEATURE:
<223> OTHER INFORMATION: Chemically Synthesized

<400> SEQUENCE: 75

Thr His Gly Val Pro Asp Pro Pro Asn Leu Glu Gly Arg Phe Ile Gln
1               5                   10                  15

Ala Phe Lys Asn Pro Asp Pro Asn His Phe Asn Ile Leu Asp Glu Tyr
            20                  25                  30

Cys Ala Glu Pro Leu Ser Gly Ser Trp Asn Val Leu Ile Ala Asp Pro
        35                  40                  45

Leu Gln His Arg Ser Gln Ala
    50                  55

<210> SEQ ID NO 76
<211> LENGTH: 55
<212> TYPE: PRT
<213> ORGANISM: Artificial Sequence
<220> FEATURE:
<223> OTHER INFORMATION: Chemically Synthesized

<400> SEQUENCE: 76

Thr His Gly Val Pro Asp Pro Pro Asn Leu Glu Gly Arg Phe Ile Gln
1               5                   10                  15

Ala Phe Lys Ser Pro Asp Pro Asn His Phe Asn Ile Leu Asp Glu Tyr
            20                  25                  30

Cys Ala Glu Pro Leu Ser Gly Gly Trp Asn Val Leu Ile Ala Asp Pro
        35                  40                  45

Leu Gln His Arg Ser Gln Ala
    50                  55

<210> SEQ ID NO 77
<211> LENGTH: 55
<212> TYPE: PRT
<213> ORGANISM: Artificial Sequence
<220> FEATURE:
<223> OTHER INFORMATION: Chemically Synthesized

<400> SEQUENCE: 77

Thr His Cys Arg Ala Asp Pro Pro Asn Leu Glu Gly Arg Phe Ile Gln
1               5                   10                  15

Pro Phe Lys Gly Pro Cys Pro Asp His Phe Asn Ile Leu Asp Glu Tyr
            20                  25                  30

Cys Lys Glu Pro Ile Ser Ala Lys Phe Gln Val Leu Ile Ala Asp Pro
        35                  40                  45

Leu Gln Tyr Arg Thr Gln His
    50                  55

<210> SEQ ID NO 78
<211> LENGTH: 55
<212> TYPE: PRT
<213> ORGANISM: Artificial Sequence
<220> FEATURE:
<223> OTHER INFORMATION: Chemically Synthesized

<400> SEQUENCE: 78

Thr Asn Gly Pro Pro Asp Pro Thr Leu Ala Cys Thr Ser Ile Leu
1               5                   10                  15

Pro Phe Thr Ser Asn Pro Pro Gln His Thr Phe Asn Ile Leu Asp Glu
            20                  25                  30

Tyr Pro Ile Gly Gln Ser Lys Gly Tyr Lys Ala Leu Phe Ala Asp Ile
        35                  40                  45

Leu Gln His Arg Asn Asn His
    50                  55

<210> SEQ ID NO 79
<211> LENGTH: 56
<212> TYPE: PRT
<213> ORGANISM: Artificial Sequence
<220> FEATURE:
<223> OTHER INFORMATION: Chemically Synthesized

<400> SEQUENCE: 79

Thr Leu Gly Val Pro Asp Lys Val Ser Ile Arg Thr Arg Gly Ile Gln
1               5                   10                  15

Lys Pro Gly Pro Ile Pro Glu Gly Asn Phe Ala Ile Leu Asp Glu Tyr
            20                  25                  30

Thr Leu Asp Asn Thr Thr Arg Asn Ser Asn Gln Ala Leu Phe Ala Asp
        35                  40                  45

Pro Tyr Gln Ala Pro Glu Phe Ser
    50                  55

<210> SEQ ID NO 80
<211> LENGTH: 59
<212> TYPE: PRT
<213> ORGANISM: Artificial Sequence
<220> FEATURE:
<223> OTHER INFORMATION: Chemically Synthesized

<400> SEQUENCE: 80

Thr Leu Gly Lys Pro Asp Pro Tyr Ser Leu Ser Asn Pro Thr Ile Lys
1               5                   10                  15

Ala Phe Ala Gln Phe Lys Arg Gly Thr Leu Asp Ile Leu Asp Glu Tyr
            20                  25                  30

Gly Gln Leu Pro Leu Thr Asp Leu Asp Ser Ser Phe Glu Phe Ile Phe
        35                  40                  45

Thr Asp Pro Tyr Gln Ala Pro Thr Asp Asn Leu
    50                  55

<210> SEQ ID NO 81
<211> LENGTH: 207
<212> TYPE: PRT
<213> ORGANISM: Alternanthera mosaic virus

<400> SEQUENCE: 81

Met Ser Thr Pro Phe Pro Gln Val Thr Gln Glu Gln Met Asn Ala Phe
1               5                   10                  15

Thr Pro His Thr Thr Ser Asn Leu Leu Pro Ser Pro Glu Gln Leu Thr
            20                  25                  30

Thr Ile Ala Asn Leu Leu Val Ala Ala Lys Val Pro Ala Ala Ser Thr
        35                  40                  45

Thr Thr Ile Ala Leu Glu Leu Val Asn Phe Cys Tyr Asp Asn Gly Ser
    50                  55                  60

Ser Thr Tyr Thr Ala Val Val Gly Pro Ser Ser Leu Ala Glu Val Ser
65                  70                  75                  80

Leu Ser Gln Val Ala Asn Ile Val Lys Ala Ser Gly Thr Ser Leu Arg
                85                  90                  95

Lys Phe Cys Arg Phe Phe Ala Pro Ile Ile Trp Asn Leu Arg Thr Asp
            100                 105                 110

Lys Thr Pro Pro Ala Asn Trp Glu Ala Asn Gly Phe Lys Pro Thr Glu
        115                 120                 125

Lys Phe Ala Ala Phe Asp Phe Phe Asp Gly Val Glu Asn Pro Ala Ala
    130                 135                 140

Met Gln Pro Pro Gly Gly Leu Val Arg Thr Pro Ser Gln Ala Glu Arg
145                 150                 155                 160

Ile Ala Asn Ala Thr Asn Lys Gln Val Asn Leu Phe Gln Ala Ala Ala
                165                 170                 175

Gln Asp Asn Asn Phe Ala Ser Asn Ser Ala Phe Ile Thr Lys Gly Gln
            180                 185                 190

Leu Ser Ser Asn Ser Pro Thr Ile Gln Tyr Leu Pro Pro Pro Glu
        195                 200                 205

<210> SEQ ID NO 82
<211> LENGTH: 207
<212> TYPE: PRT
<213> ORGANISM: Altemanthera mosaic virus

<400> SEQUENCE: 82

Met Ser Thr Pro Phe Pro Gln Val Thr Gln Glu Gln Ile Asp Ala Phe
1               5                   10                  15

Thr Pro His Thr Thr Ser Asn Leu Leu Pro Ser Pro Glu Gln Leu Thr
                20                  25                  30

Thr Ile Ala Ser Leu Leu Val Ala Ala Lys Val Pro Ala Ala Ser Thr
            35                  40                  45

Thr Thr Ile Ala Leu Glu Leu Val Asn Phe Cys Tyr Asp Asn Gly Ser
50                  55                  60

Ser Ala Tyr Thr Val Val Gly Pro Ser Ile Ser Gly Val Ser
65                  70                  75                  80

Leu Ser Gln Val Ala Asn Ile Val Lys Ala Ser Gly Thr Ser Leu Arg
                85                  90                  95

Lys Phe Cys Arg Phe Phe Ala Pro Ile Ile Trp Asn Leu Arg Thr Asp
            100                 105                 110

Lys Thr Pro Pro Ala Asn Trp Glu Ala Asn Gly Phe Lys Pro Thr Glu
        115                 120                 125

Lys Phe Ala Ala Phe Asp Phe Asp Gly Val Glu Asn Pro Ala Ala
    130                 135                 140

Met Gln Pro Pro Gly Gly Leu Val Arg Ala Pro Ser Gln Ala Glu Arg
145                 150                 155                 160

Ile Ala Asn Ala Thr Asn Lys Gln Val Asn Leu Phe Gln Ala Ala Ala
                165                 170                 175

Gln Asp Asn Asn Phe Ala Ser Asn Ser Ala Phe Ile Thr Lys Gly Gln
            180                 185                 190

Leu Ser Ser Asn Ser Pro Thr Ile Gln Tyr Leu Pro Pro Pro Glu
        195                 200                 205

<210> SEQ ID NO 83
<211> LENGTH: 1541
<212> TYPE: PRT
<213> ORGANISM: Altemanthera mosaic virus

<400> SEQUENCE: 83

Met Ala His Phe Arg Ser Val Leu Asp Gln Met Asn Asp Pro Ser Leu
1               5                   10                  15

Arg Ala Val Ile Gln Glu Glu Ala Tyr Arg Glu Ile Lys Lys Thr Ile
                20                  25                  30

Ala Glu Thr Lys Gln Tyr Asn Pro Tyr Ala Gln Asp Pro Ala Ala Ala
            35                  40                  45

Asp Ser Leu Glu Lys Leu Gly Ile Glu Ser Asn Pro Phe Ser Val Arg
        50                  55                  60

Ala His Thr His Ala Ala Ala Lys Ser Ile Glu Leu Asp Met Tyr Lys

```
             65                  70                  75                  80
Ile Thr Gly Tyr Ser Leu Pro Lys Glu Asn Pro Ile Thr Phe Leu Phe
                     85                  90                  95

Met Lys Arg Ser Lys Leu Gln Tyr Phe His Arg Gly Pro Gln His Gly
                100                 105                 110

Asp Leu Phe Leu Asn Ala Trp Ile Glu Pro Lys Asp Val Thr Arg Tyr
            115                 120                 125

Asn Leu Glu Asp Leu Phe Lys Pro Ser Ile Thr Pro Glu Ile Gln Thr
        130                 135                 140

Arg Val Ala Phe Ile Gly Asp Thr Leu His Phe Leu Pro Leu Gly Ala
145                 150                 155                 160

Ile Arg Glu Ile Phe Thr Ser Ser Gln Lys Leu Gln Thr Leu Tyr Ala
                165                 170                 175

Thr Met Val Leu Pro Pro Glu Ala Met His Arg Met His Ser Ile His
                180                 185                 190

Pro Ser Ile Tyr Glu Leu Glu Phe His Glu Arg Asn Phe Ile Tyr Lys
            195                 200                 205

Pro Gly Gly His Ala Gly Ala Ser Tyr Cys His Glu Tyr Ser Gln Leu
        210                 215                 220

Gln Trp Leu Lys Val Gly Lys Phe Glu Trp Cys Asp Lys Arg Tyr Gln
225                 230                 235                 240

Lys His Tyr Val Thr Ser Gln Ile Leu Glu Thr Lys Gly Ala Asn His
                245                 250                 255

Leu Phe Val Phe Gln Arg Gly Asn Phe Ala Thr Pro Thr Tyr Arg Thr
                260                 265                 270

Phe Gly Val Glu Thr Lys Phe Val Thr Leu Pro Pro Ile Phe Leu Pro
            275                 280                 285

Lys Lys Tyr Asn Ala Arg Tyr Pro Ile Lys Lys Thr Val Ala Gln Gln
        290                 295                 300

Leu Phe Leu Tyr Ile Lys Ser Val Lys Thr Val Thr Glu Arg Asp Ile
305                 310                 315                 320

Trp Ala Lys Val Arg Gln Ile Ile Lys Thr Ala Glu Leu Gln Ser Tyr
                325                 330                 335

Ser Ala Lys Glu Leu Ala Leu Ile Val Asn Tyr Tyr Leu Leu Ile Ser
                340                 345                 350

Lys Leu Asp Ser Val Thr Cys Phe Asp Asn Val Leu Thr Gly Gly Ala
            355                 360                 365

Leu Lys Lys Leu Phe Lys Pro Ile Val Ala Trp Trp Ser Thr Phe Lys
        370                 375                 380

Gly Ala Leu Phe Gly Lys Glu Phe Glu Gln Leu Met Glu Ala Leu
385                 390                 395                 400

Glu Trp Val Asp Val Ser Leu Ser Tyr Lys Val Glu Thr Tyr Ser Gln
                405                 410                 415

Ala Asn Pro Asn Asn Gln Pro Lys Val Met Phe Gly Tyr Glu Trp Leu
                420                 425                 430

Ser Thr Glu Thr Gly Ala Pro Gly Thr Glu Glu Asp Val Ala Pro Glu
            435                 440                 445

Asn Pro Gln Glu Asp Glu Asp Pro His Glu Lys Tyr Ile Gln Ala Leu
        450                 455                 460

Gln Thr Leu Thr Lys Ala Leu Asp Pro Glu Asn Ala Pro Pro Gln Thr
465                 470                 475                 480

Glu Pro Ala Gln Ser Ser Ile Asn Asp Pro Gln Gln Glu Glu His
                485                 490                 495
```

-continued

Pro Arg Ser Pro His Asp Leu His Thr Asp Glu Ser Pro Ser Cys Ser
                500                 505                 510

Gly Ser Leu Asn Ser Tyr Ala Cys His Cys Pro Cys Gly Ile Glu Leu
            515                 520                 525

Lys Ile Phe Ser Ala Glu Phe Pro Ile Pro Pro Leu Ser His Gly
        530                 535                 540

Asp Arg Leu Lys Asn Arg Glu Ala Phe Phe Phe Ser Arg Asp Gly Thr
545                 550                 555                 560

Pro Tyr Ser Tyr Thr Gly Gly Ser His Val Ser Arg Gly Trp Pro Ala
                565                 570                 575

Phe Leu Asp Gln Ile Leu Ala Thr Ala Glu Leu Val Arg Pro Ile Pro
            580                 585                 590

His Phe Asn Gln Cys Leu Ile Gln Lys Tyr Gln Arg Gly Ala Ser Ile
        595                 600                 605

Pro Phe His Ser Asp Asp Glu Pro Cys Tyr Asp Val Asp His Gln Val
    610                 615                 620

Leu Thr Ile Asn Leu Thr Gly Glu Ala Glu Phe Lys Thr Ser Cys Lys
625                 630                 635                 640

Ala Gly Ser Gly Ser Cys Thr Leu Ala Glu Asn Gln Phe His Leu Ser
                645                 650                 655

Pro Pro Gly Phe Gln Lys Thr His Lys His Ser Val Val Ser Leu Ser
            660                 665                 670

Ala Gly Arg Val Ser Leu Thr Phe Arg Ser Thr Val Lys Gln Gly Val
        675                 680                 685

Thr Ser Glu Glu Gly Asp Tyr Val Glu Pro Asp Asn Leu Pro Trp Lys
    690                 695                 700

Ala Trp Leu Glu Lys Leu Arg Asn Leu Gly Phe Arg Gly Thr Gln Leu
705                 710                 715                 720

Gln Tyr Asp Pro Asn Gly Ala Leu Ile Ser Pro Ile Glu Ser Ile Lys
                725                 730                 735

Ser Leu Pro Lys Cys Ser Pro Glu Lys Val Asn Pro Ser Leu Leu Lys
            740                 745                 750

Met Leu Asn Asp Gln Ala Arg Ala Pro Thr Pro Phe Ser Pro Ser Pro
        755                 760                 765

Ile Arg Ala Lys Ala Tyr Ser Ser Asp Val Lys Asn Ser Arg Ile Gly
    770                 775                 780

Ala Leu Leu Arg Gln Gln Gly Lys Asp Trp Gly His Arg Phe Asp Ser
785                 790                 795                 800

Leu Val Glu Asn Gly Gln Arg Gln Leu Ala Ile Ser Val Ile His Gly
                805                 810                 815

Ala Gly Gly Ser Gly Lys Ser Arg Ala Leu Gln Met Tyr Leu Lys Asp
            820                 825                 830

Asn Pro Asp Ala Asp Val Thr Ile Val Leu Pro Thr Asn Glu Leu Arg
        835                 840                 845

Leu Asp Trp Leu Lys Lys Leu Pro Thr Phe Pro Ala Asp Gln Ile Lys
    850                 855                 860

Thr Phe Glu Lys Ala Leu Leu Ala Pro Ile Lys Pro Thr Val Ile Phe
865                 870                 875                 880

Asp Asp Tyr Gly Lys Leu Pro Ala Gly Tyr Ile Glu Ala Phe Ser Cys
                885                 890                 895

Tyr Met Ser Ser Val Glu Leu Leu Val Leu Thr Gly Asp Ser Lys Gln
            900                 905                 910

Ser Val His His Glu Ser Asn Glu Asn Ala Met Ser Ser Leu Ile Glu
        915                 920                 925

```
Pro Phe Thr Leu Glu Ala Asp Lys Tyr Ser Arg Tyr Tyr Ile Asn Ala
    930                 935                 940

Thr His Arg Asn Lys Arg Asp Leu Ala Asn Lys Leu Gly Val Tyr Ser
945                 950                 955                 960

Glu Val Thr Gly Ile Thr Ser Ile Thr Gln Gly Asn His Pro Val Pro
                965                 970                 975

Gly Leu His Leu Leu Val Pro Ser Leu Tyr Lys Lys Glu Ala Phe Ser
            980                 985                 990

Glu Met Gly His Lys Val Ser Thr Tyr Ala Gly Cys Gln Gly Leu Thr
        995                 1000                1005

Ala Pro Arg Val Gln Ile Leu Leu Ser Glu Glu Thr Ser Met Cys
    1010                1015                1020

Ser Arg Glu Val Ile Tyr Thr Ala Leu Ser Arg Ala Val His Ser
    1025                1030                1035

Ile His Phe Val Asn Cys Gly Pro Asn Asn Gln Ala Phe Trp Ala
    1040                1045                1050

Lys Leu Glu Ser Thr Pro Tyr Leu Lys Ala Phe Leu Ser Thr Leu
    1055                1060                1065

Arg Glu Asp Ala Ala Pro Val Val Lys Pro Lys Glu Glu Ala Pro
    1070                1075                1080

Ala Pro Val Asp Pro Pro Lys Thr His Ile Pro Val Asp Ser Ala
    1085                1090                1095

Met Pro Ile Tyr Glu Asp Leu Leu Asp Gln Met Pro Glu Lys His
    1100                1105                1110

Glu Arg Glu Ile Phe Ser Glu Arg His Gly His Ser Asn Cys Val
    1115                1120                1125

Gln Thr Glu Asp Thr Phe Val Gln Met Phe Ser His Gln Gln Ala
    1130                1135                1140

Lys Asp Glu Thr Leu Leu Trp Ala Thr Ile Glu Ala Arg Leu Val
    1145                1150                1155

Ile Ser Asn Pro Lys Ala Asn Trp Gln Glu Phe Met Glu Lys Arg
    1160                1165                1170

Pro Ile Gly Asp Val Leu Phe Gly Phe Tyr Arg Glu Ala Met Gly
    1175                1180                1185

Leu Pro Thr Glu Pro Ile Ala Phe Glu Pro Gln Leu Trp Glu Ser
    1190                1195                1200

Cys Ile His Glu Val Gln Arg Thr Tyr Leu Ala Lys Pro Ile Asn
    1205                1210                1215

Met Leu Lys Asn Gly Gln Ala Arg Gln Ser Pro Asp Tyr Asp Pro
    1220                1225                1230

Asn Met Ile Ser Leu Phe Leu Lys Ser Gln Trp Val Lys Lys Met
    1235                1240                1245

Glu Lys Leu Gly Ala Leu Lys Ile Lys Pro Gly Gln Thr Ile Ala
    1250                1255                1260

Ser Phe His Gln Ala Thr Val Met Leu Phe Gly Thr Met Ala Arg
    1265                1270                1275

Tyr Met Arg Arg Met Arg Glu Ile Phe Gln Pro Lys Asn Ile Ala
    1280                1285                1290

Ile Asn Cys Glu Met Thr Pro Glu Asp Leu Thr Asp Trp Ala Val
    1295                1300                1305

Gly Ser Ala Gly Gln Trp Lys Phe Ala Gly Pro Ser Leu Ala Asn
    1310                1315                1320

Asp Phe Thr Ala Phe Asp Gln Ser Gln Asp Gly Ala Met Leu Gln
```

```
                        1325                1330                1335

Phe Glu  Val Leu Lys Ala Lys  His His Ser Ile Pro  Glu Asp Val
    1340             1345                 1350

Leu Asp  Ala Tyr Leu His Ile  Lys Thr Asn Ser Lys  Ile Phe Leu
    1355             1360                 1365

Gly Thr  Leu Thr Ile Met Arg  Leu Thr Gly Glu Gly  Pro Thr Phe
    1370             1375                 1380

Asp Ala  Asn Thr Glu Cys Asn  Ile Ala Phe Thr His  Ala Lys Phe
    1385             1390                 1395

Gln Ile  Pro Lys Gly Thr Ala  Gln Leu Tyr Ala Gly  Asp Asp Ser
    1400             1405                 1410

Ala Ile  Asp Gly Asn Pro Pro  Val Arg Glu Ser Phe  Arg Leu Val
    1415             1420                 1425

Glu Gln  Lys Leu Lys Leu Arg  Ser Lys Pro Ala Ile  Ala Met Gln
    1430             1435                 1440

Glu Lys  Gly Asp Trp Ala Glu  Phe Cys Gly Tyr Arg  Ile Thr Pro
    1445             1450                 1455

Lys Gly  Phe Ile Lys Asp Pro  Lys Lys Leu His Ala  Ser Leu Val
    1460             1465                 1470

Leu Glu  Lys Lys Arg Gly Asn  Leu Lys Asn Val Leu  Arg Ser Tyr
    1475             1480                 1485

Glu Leu  Asp Leu Ala Leu Ala  Tyr Gln His Arg Asp  Glu Leu His
    1490             1495                 1500

Glu Leu  Leu Ser Glu Glu Leu  Arg Leu His Tyr Asp  Thr Val
    1505             1510                 1515

Arg Thr  Leu Val Lys Ser Gly  Gly Gly Glu Val Leu  Lys Thr Phe
    1520             1525                 1530

Leu Pro  Lys Asp Glu Ser Leu  Tyr
    1535             1540

<210> SEQ ID NO 84
<211> LENGTH: 232
<212> TYPE: PRT
<213> ORGANISM: Alternanthera mosaic virus

<400> SEQUENCE: 84

Met Asn His Phe Thr Asn Leu Leu Ile Glu Glu Gly Tyr Val Arg Thr
1               5                   10                  15

Asn Glu Ile Leu Ser Asp Thr Leu Val Val His Ala Val Ala Gly Ala
                20                  25                  30

Gly Lys Ser Thr Leu Ile Arg Lys Phe Ile His Gln His Pro Gln Ala
            35                  40                  45

Arg Ala Tyr Thr His Gly Val Pro Asp Pro Asn Leu Glu Gly Arg
        50                  55                  60

Phe Ile Gln Ala Phe Lys Asn Pro Asp Pro Asn His Phe Asn Ile Leu
65                  70                  75                  80

Asp Glu Tyr Cys Ala Glu Pro Leu Ser Gly Ser Trp Asn Val Leu Ile
                85                  90                  95

Ala Asp Pro Leu Gln His Arg Ser Gln Ala Leu Arg Pro His Tyr Ile
            100                 105                 110

Lys Arg Glu Ser His Arg Leu Gly Val Ala Thr Cys Glu Leu Leu Thr
        115                 120                 125

Arg Val Gly Leu Pro Val Leu Ser Asn Lys Thr Glu Asp Gln Val Asp
    130                 135                 140

Tyr Gln Gly Ile Phe Glu Gly Pro Leu Phe Gly Thr Val Ile Ala Leu
```

-continued

```
                145                 150                 155                 160
Asp Ser Thr Val Arg Ala Leu Leu Val Lys His Gly Ile Pro Pro Leu
                165                 170                 175

Cys Pro Ala Glu Val Leu Gly Ser Glu Phe Glu Gln Thr Thr Val Val
            180                 185                 190

Ser Glu Val Pro Leu Ser Gln Val Lys Phe Lys His Ala Leu Tyr Ile
        195                 200                 205

Ala Leu Thr Arg His Lys Lys Ser Leu His Val Arg Ala Pro Pro Leu
    210                 215                 220

Pro Asp Thr Pro Arg Arg Leu Leu
225                 230

<210> SEQ ID NO 85
<211> LENGTH: 1541
<212> TYPE: PRT
<213> ORGANISM: Alternanthera mosaic virus

<400> SEQUENCE: 85

Met Ala His Phe Arg Ser Val Leu Asp Gln Met Asn Asp Pro Ser Leu
1               5                   10                  15

Arg Ala Val Ile Gln Glu Glu Ala Tyr Arg Glu Ile Lys Lys Thr Ile
                20                  25                  30

Ala Glu Thr Lys Gln Tyr Asn Pro Tyr Ala Gln Asp Pro Ala Ala Ala
            35                  40                  45

Asp Ser Leu Glu Lys Leu Gly Ile Glu Ser Asn Pro Phe Ser Val Arg
        50                  55                  60

Ala His Thr His Ala Ala Lys Ser Ile Glu Leu Asp Met Tyr Lys
65                  70                  75                  80

Ile Thr Gly Tyr Ser Leu Pro Lys Glu Asn Pro Ile Thr Phe Leu Phe
                85                  90                  95

Met Lys Arg Ser Lys Leu Gln Tyr Phe His Arg Gly Pro Gln His Gly
                100                 105                 110

Asp Leu Phe Leu Asn Ala Cys Ile Glu Pro Lys Asp Val Thr Arg Tyr
            115                 120                 125

Ala Leu Glu Asp Leu Phe Lys Pro Ser Thr Thr Pro Glu Ile Gln Thr
        130                 135                 140

Arg Val Ala Phe Ile Gly Asp Thr Leu His Phe Leu Pro Leu Gly Ala
145                 150                 155                 160

Ile Arg Glu Ile Phe Thr Ser Ser Gln Lys Leu Gln Thr Leu Tyr Ala
                165                 170                 175

Thr Met Val Leu Pro Pro Glu Ala Met His Arg Met His Ser Ile His
            180                 185                 190

Pro Ser Ile Tyr Glu Leu Glu Phe His Glu Lys Asn Phe Ile Tyr Lys
        195                 200                 205

Pro Gly Gly His Ala Gly Ala Ser Tyr Cys His Glu Tyr Ser Gln Leu
    210                 215                 220

Gln Trp Leu Lys Val Gly Lys Phe Glu Trp Cys Asp Lys Lys Tyr Gln
225                 230                 235                 240

Lys His Tyr Val Thr Ser Gln Ile Leu Glu Thr Lys Gly Ala Asn His
                245                 250                 255

Leu Phe Val Phe Gln Arg Gly Asn Phe Ala Thr Pro Thr Tyr Arg Thr
            260                 265                 270

Phe Gly Val Glu Thr Lys Phe Val Thr Leu Pro Pro Ile Phe Leu Pro
        275                 280                 285

Lys Lys Tyr Asn Ala Arg Tyr Pro Ile Lys Lys Thr Val Ala Gln Gln
```

|  |  |  | 290 |  |  |  | 295 |  |  |  | 300 |  |  |  |
|---|---|---|---|---|---|---|---|---|---|---|---|---|---|---|

Leu Phe Leu Tyr Ile Lys Ser Val Lys Thr Val Thr Glu Arg Asp Ile
305             310                 315                 320

Trp Ala Lys Val Arg Gln Ile Ile Lys Thr Ala Glu Leu Gln Ser Tyr
                325                 330                 335

Ser Ala Lys Glu Leu Ala Leu Ile Val Asn Tyr Tyr Leu Leu Ile Ser
                340                 345                 350

Lys Leu Asp Ser Val Thr Cys Phe Asp Asn Val Leu Thr Gly Gly Val
                355                 360                 365

Leu Lys Lys Leu Phe Lys Pro Ile Val Ala Trp Trp Ser Thr Phe Lys
370                 375                 380

Gly Lys Ile Phe Gly Lys Glu Phe Glu Gln Leu Met Glu Ala Leu
385                 390                 395                 400

Glu Trp Val Asp Val Ser Leu Ser Tyr Lys Val Glu Thr Tyr Ser Gln
                405                 410                 415

Ala Asn Pro Asn Gln Pro Lys Val Met Phe Gly Tyr Glu Trp Leu
                420                 425                 430

Ser Thr Glu Thr Gly Thr Pro Gly Thr Glu Glu Asp Ala Ala Pro Glu
                435                 440                 445

Thr Pro Gln Glu Asp Glu Pro His Glu Arg Tyr Ile Gln Ala Leu
450                 455                 460

Gln Thr Leu Thr Lys Ala Leu Asp Gln Glu Ser Ala Pro Pro Thr
465                 470                 475                 480

Glu Pro Ala Gln Cys Ser Ser Thr Ser Asn Pro Gln Gln Glu Glu His
                485                 490                 495

Phe Arg Pro Pro His Asn Leu His Thr Asp Glu Thr Pro Ser Cys Ser
                500                 505                 510

Gly Ser Ser Asn Ser Phe Ala Cys His Cys Pro Cys Gly Thr Glu Leu
                515                 520                 525

Lys Val Phe Ser Ala Glu Phe Pro Pro Ile Pro Pro Leu Ser His Gly
                530                 535                 540

Asp Arg Leu Lys Asn Arg Glu Ala Phe Phe Phe Ser Arg Asp Gly Thr
545                 550                 555                 560

Pro Tyr Ser Tyr Thr Gly Gly Ser His Ala Ser Arg Gly Trp Pro Thr
                565                 570                 575

Phe Leu Asp Gln Ile Leu Ala Thr Ala Glu Leu Val Arg Pro Leu Pro
                580                 585                 590

His Phe Asn Gln Cys Leu Ile Gln Lys Tyr Gln Arg Gly Ala Ser Ile
                595                 600                 605

Pro Phe His Arg Asp Asp Glu Pro Cys Tyr Asp Ala Asp His Gln Val
                610                 615                 620

Leu Thr Ile Asn Leu Thr Gly Glu Ala Glu Phe Lys Ile Ser Cys Lys
625                 630                 635                 640

Ala Gly Ser Gly Ser Cys Thr Leu Val Glu Asn Gln Phe His Leu Ser
                645                 650                 655

Pro Pro Gly Phe Gln Lys Thr His Lys His Ser Val Val Ser Leu Ser
                660                 665                 670

Ala Gly Arg Val Ser Leu Thr Phe Arg Ser Thr Val Lys Gln Ser Val
                675                 680                 685

Thr Ser Glu Glu Gly Asp Cys Val Glu Pro Asp Asn Leu Pro Trp Lys
                690                 695                 700

Ala Trp Leu Gly Lys Leu Arg Asn Leu Gly Phe Arg Gly Met Gln Leu
705                 710                 715                 720

-continued

```
Gln Tyr Asp Pro Asn Gly Ala Leu Ile Ser Pro Ile Glu Ser Val Lys
                725                 730                 735

Ser Leu Pro Lys Cys Ser Pro Glu Lys Val Asp Pro Ser Leu Leu Lys
            740                 745                 750

Met Leu Asp Asn Gln Ala Arg Ala Pro Thr Pro Phe Ser Pro Ser Pro
        755                 760                 765

Ile Arg Ala Lys Ala Tyr Ser Ser Asp Val Lys Asn Ser Arg Ile Gly
    770                 775                 780

Ala Leu Leu Arg Gln Gln Gly Lys Asp Trp Gly His Arg Phe Asp Ser
785                 790                 795                 800

Leu Val Glu Asn Gly Gln Arg Gln Leu Ala Ile Ser Val Ile His Gly
                805                 810                 815

Ala Gly Gly Ser Gly Lys Ser Arg Ala Leu Gln Met Tyr Leu Lys Asp
            820                 825                 830

Asn Pro Asp Ala Asp Val Thr Ile Val Leu Pro Thr Asn Glu Leu Arg
        835                 840                 845

Leu Asp Trp Leu Lys Lys Leu Pro Thr Phe Pro Ala Asp Gln Ile Lys
    850                 855                 860

Thr Phe Glu Lys Ala Leu Leu Ala Pro Thr Lys Pro Thr Val Ile Phe
865                 870                 875                 880

Asp Asp Tyr Gly Lys Leu Pro Ala Gly Tyr Ile Glu Ser Phe Ser Phe
                885                 890                 895

Tyr Met Ser Ser Ala Glu Leu Val Leu Thr Gly Asp Ser Lys Gln
            900                 905                 910

Ser Val His His Glu Ser Asn Ala Met Ser Ser Leu Ile Glu
        915                 920                 925

Pro Phe Thr Leu Glu Ala Asp Lys Tyr Ser Arg Tyr Tyr Ile Asn Ala
    930                 935                 940

Thr His Arg Asn Lys Arg Asp Leu Ala Asn Lys Leu Gly Val Tyr Ser
945                 950                 955                 960

Glu Val Thr Gly Ile Thr Ser Ile Thr Gln Gly Asn His Pro Val Pro
                965                 970                 975

Gly Leu His Leu Leu Val Pro Ser Leu Tyr Lys Lys Glu Ala Phe Ser
            980                 985                 990

Glu Met Gly His Lys Val Ser Thr Tyr Ala Gly Cys Gln Gly Leu Thr
        995                 1000                1005

Ala Pro Arg Val Gln Ile Leu Leu Ser Glu Glu Thr Ser Met Cys
    1010                1015                1020

Ser Arg Glu Val Ile Tyr Thr Ala Leu Ser Arg Ala Val His Ser
    1025                1030                1035

Ile His Phe Val Asn Cys Gly Pro Asn Asn Gln Ala Phe Trp Ala
    1040                1045                1050

Lys Leu Glu Ser Thr Pro Tyr Leu Lys Ala Phe Leu Ser Thr Leu
    1055                1060                1065

Arg Glu Asp Ala Ala Pro Val Val Lys Pro Lys Glu Glu Ala Pro
    1070                1075                1080

Ala Pro Val Asp Pro Pro Lys Thr His Ile Pro Val Asp Ser Ala
    1085                1090                1095

Met Pro Ile Tyr Glu Asp Leu Leu Asp Gln Met Arg Glu Lys His
    1100                1105                1110

Glu Arg Glu Ile Phe Ser Glu Lys His Gly His Ser Asn Cys Val
    1115                1120                1125

Gln Thr Glu Asp Thr Phe Val Gln Met Phe Ser His Gln Gln Ala
    1130                1135                1140
```

```
Lys Asp Glu Thr Leu Leu Trp Ala Thr Ile Glu Ala Arg Leu Val
1145                1150                1155

Ile Ser Asn Pro Lys Ala Asn Trp Gln Glu Phe Met Glu Lys Arg
1160                1165                1170

Pro Ile Gly Asp Val Leu Phe Gly Phe Tyr Arg Glu Ala Met Gly
1175                1180                1185

Leu Pro Thr Glu Pro Ile Ala Phe Glu Pro Gln Leu Trp Glu Ser
1190                1195                1200

Cys Ile His Glu Val Gln Arg Thr Tyr Leu Ala Lys Pro Ile Asn
1205                1210                1215

Met Leu Lys Asn Gly Gln Ala Arg Gln Ser Pro Asp Tyr Asp Pro
1220                1225                1230

Asn Met Ile Ser Leu Phe Leu Lys Ser Gln Trp Val Lys Lys Met
1235                1240                1245

Glu Lys Leu Gly Ala Leu Arg Ile Lys Pro Gly Gln Thr Ile Ala
1250                1255                1260

Ser Phe His Gln Ala Thr Val Met Leu Phe Gly Thr Met Ala Arg
1265                1270                1275

Tyr Met Arg Arg Met Arg Glu Ile Phe Gln Pro Lys Asn Ile Ala
1280                1285                1290

Ile Asn Cys Glu Met Thr Pro Glu Asp Leu Thr Asp Trp Ala Val
1295                1300                1305

Gly Ser Ala Gly Gln Trp Lys Phe Ala Gly Pro Ser Leu Ala Asn
1310                1315                1320

Asp Phe Thr Ala Phe Asp Gln Ser Gln Asp Gly Ala Met Leu Gln
1325                1330                1335

Phe Glu Val Leu Lys Ala Lys His His Ser Ile Pro Glu Asp Val
1340                1345                1350

Leu Asp Ala Tyr Leu His Ile Lys Thr Asn Ser Lys Ile Phe Leu
1355                1360                1365

Gly Thr Leu Thr Ile Met Arg Leu Thr Gly Glu Gly Pro Thr Phe
1370                1375                1380

Asp Ala Asn Thr Glu Cys Asn Ile Ala Phe Thr His Ala Lys Phe
1385                1390                1395

Gln Ile Pro Lys Gly Thr Ala Gln Leu Tyr Ala Gly Asp Asp Ser
1400                1405                1410

Ala Ile Asp Gly Asn Pro Pro Val Arg Glu Ser Phe Arg Leu Val
1415                1420                1425

Glu Gln Lys Leu Lys Leu Arg Ser Lys Pro Ala Ile Ala Met Gln
1430                1435                1440

Glu Lys Gly Asp Trp Ala Glu Phe Cys Gly Tyr Arg Ile Thr Pro
1445                1450                1455

Lys Gly Phe Ile Lys Asp Pro Lys Lys Leu His Ala Ser Leu Val
1460                1465                1470

Leu Glu Lys Lys Arg Gly Asn Leu Lys Asn Val Leu Arg Ser Tyr
1475                1480                1485

Glu Leu Asp Leu Ala Leu Ala Tyr Gln His Arg Asp Glu Leu His
1490                1495                1500

Glu Leu Leu Ser Glu Glu Glu Leu Arg Leu His Tyr Asp Thr Val
1505                1510                1515

Arg Thr Leu Val Lys Ser Gly Gly Gly Glu Val Leu Lys Thr Phe
1520                1525                1530

Leu Ser Lys Asp Glu Ser Leu Tyr
```

<210> SEQ ID NO 86
<211> LENGTH: 232
<212> TYPE: PRT
<213> ORGANISM: Altemanthera mosaic virus

<400> SEQUENCE: 86

```
Met Asn His Phe Thr Asn Leu Leu Ile Glu Glu Gly Tyr Val Arg Thr
1               5                   10                  15

Asn Glu Ile Leu Ser Asp Thr Leu Val Val His Ala Val Ala Gly Ala
            20                  25                  30

Gly Lys Ser Thr Leu Ile Arg Lys Phe Ile His Gln His Pro Gln Ala
        35                  40                  45

Arg Ala Tyr Thr His Gly Val Pro Asp Pro Asn Leu Glu Gly Arg
    50                  55                  60

Phe Ile Gln Ala Phe Lys Asn Pro Asp Pro Asn His Phe Asn Ile Leu
65                  70                  75                  80

Asp Glu Tyr Cys Ala Glu Pro Pro Ser Gly Ser Trp Asn Val Leu Ile
                85                  90                  95

Ala Asp Pro Leu Gln His Arg Ser Gln Ala Leu Arg Pro His Tyr Ile
            100                 105                 110

Lys Arg Glu Ser His Arg Leu Gly Val Ala Thr Cys Glu Leu Leu Thr
        115                 120                 125

Arg Val Gly Leu Pro Val Leu Ser Asn Lys Thr Glu Asp Gln Val Asp
    130                 135                 140

Tyr Gln Gly Ile Phe Glu Gly Pro Leu Phe Gly Thr Val Ile Ala Leu
145                 150                 155                 160

Asp Ser Thr Val Arg Ala Leu Leu Val Lys His Gly Ile Pro Pro Leu
                165                 170                 175

Cys Pro Ala Glu Val Leu Gly Ser Glu Phe Glu Gln Thr Thr Val Val
            180                 185                 190

Ser Glu Val Pro Leu Ser Gln Val Lys Phe Lys His Ala Leu Tyr Ile
        195                 200                 205

Ala Leu Thr Arg His Lys Lys Ser Leu His Val Arg Ala Pro Pro Leu
    210                 215                 220

Pro Asp Thr Pro Arg Arg Leu Leu
225                 230
```

<210> SEQ ID NO 87
<211> LENGTH: 1541
<212> TYPE: PRT
<213> ORGANISM: Altemanthera mosaic virus

<400> SEQUENCE: 87

```
Met Ala His Phe Arg Ser Val Leu Asp Gln Met Asn Asp Pro Ser Leu
1               5                   10                  15

Arg Ala Val Ile Gln Glu Glu Ala Tyr Arg Glu Ile Lys Lys Thr Ile
            20                  25                  30

Ala Glu Thr Lys Gln Tyr Asn Pro Tyr Ala Gln Asp Pro Ala Ala Ala
        35                  40                  45

Asp Ser Leu Glu Lys Leu Gly Ile Glu Ser Asn Pro Phe Ser Val Arg
    50                  55                  60

Ala His Thr His Ala Ala Ala Lys Ser Ile Glu Leu Asp Met Tyr Lys
65                  70                  75                  80

Ile Thr Gly Tyr Ser Leu Pro Lys Glu Asn Pro Ile Thr Phe Leu Phe
                85                  90                  95
```

```
Met Lys Arg Ser Lys Leu Gln Tyr Phe His Arg Gly Pro Gln His Gly
            100                 105                 110

Asp Leu Phe Leu Asn Ala Cys Ile Glu Pro Lys Asp Val Thr Arg Tyr
            115                 120                 125

Ala Leu Glu Asp Leu Phe Lys Pro Ser Thr Thr Pro Glu Ile Gln Thr
        130                 135                 140

Arg Val Ala Phe Ile Gly Asp Thr Leu His Phe Leu Pro Leu Gly Ala
145                 150                 155                 160

Ile Arg Glu Ile Phe Thr Ser Ser Gln Lys Leu Gln Thr Leu Tyr Ala
                165                 170                 175

Thr Met Val Leu Pro Pro Glu Ala Met His Arg Met His Ser Ile His
            180                 185                 190

Pro Ser Ile Tyr Glu Leu Glu Phe His Glu Lys Asn Phe Ile Tyr Lys
            195                 200                 205

Pro Gly Gly His Ala Gly Ala Ser Tyr Cys His Glu Tyr Ser Gln Leu
        210                 215                 220

Gln Trp Leu Lys Val Gly Lys Phe Glu Trp Cys Asp Lys Lys Tyr Gln
225                 230                 235                 240

Lys His Tyr Val Thr Ser Gln Ile Leu Glu Thr Lys Gly Ala Asn His
                245                 250                 255

Leu Phe Val Phe Gln Arg Gly Asn Phe Ala Thr Pro Thr Tyr Arg Thr
            260                 265                 270

Phe Gly Val Glu Thr Lys Phe Val Thr Leu Pro Pro Ile Phe Leu Pro
            275                 280                 285

Lys Lys Tyr Asn Ala Arg Tyr Pro Ile Lys Lys Thr Val Ala Gln Gln
        290                 295                 300

Leu Phe Leu Tyr Ile Lys Ser Val Lys Thr Val Thr Glu Arg Asp Ile
305                 310                 315                 320

Trp Ala Lys Val Arg Gln Ile Ile Lys Thr Ala Glu Leu Gln Ser Tyr
                325                 330                 335

Ser Ala Lys Glu Leu Ala Leu Ile Val Asn Tyr Tyr Leu Leu Ile Ser
            340                 345                 350

Lys Leu Asp Ser Val Thr Cys Phe Asp Asn Val Leu Thr Gly Gly Val
            355                 360                 365

Leu Lys Lys Leu Phe Lys Pro Ile Val Ala Trp Trp Ser Thr Phe Lys
        370                 375                 380

Gly Lys Ile Phe Gly Lys Glu Glu Phe Glu Gln Leu Met Glu Ala Leu
385                 390                 395                 400

Glu Trp Val Asp Val Ser Leu Ser Tyr Lys Val Glu Thr Tyr Ser Gln
                405                 410                 415

Ala Asn Pro Asn Asn Gln Pro Lys Val Met Phe Gly Tyr Glu Trp Leu
            420                 425                 430

Ser Thr Glu Thr Gly Thr Pro Gly Thr Glu Glu Asp Ala Ala Pro Glu
            435                 440                 445

Thr Pro Gln Glu Asp Glu Asp Pro His Glu Arg Tyr Ile Gln Ala Leu
        450                 455                 460

Gln Thr Leu Thr Lys Ala Leu Asp Gln Glu Ser Ala Pro Pro Pro Thr
465                 470                 475                 480

Glu Pro Ala Gln Cys Ser Ser Thr Ser Asn Pro Gln Gln Glu Glu His
                485                 490                 495

Phe Arg Pro Pro His Asn Leu His Thr Asp Glu Thr Pro Ser Cys Ser
            500                 505                 510

Gly Ser Ser Asn Ser Phe Ala Cys His Cys Pro Cys Gly Thr Glu Leu
```

```
                515                 520                 525
Lys Val Phe Ser Ala Glu Phe Pro Pro Ile Pro Leu Ser His Gly
            530                 535                 540

Asp Arg Leu Lys Asn Arg Glu Ala Phe Phe Ser Arg Asp Gly Thr
545                 550                 555                 560

Pro Tyr Ser Tyr Thr Gly Gly Ser His Ala Ser Arg Gly Trp Pro Thr
                565                 570                 575

Phe Leu Asp Gln Ile Leu Ala Thr Ala Glu Leu Val Arg Pro Leu Pro
            580                 585                 590

His Phe Asn Gln Cys Leu Ile Gln Lys Tyr Gln Arg Gly Ala Ser Ile
            595                 600                 605

Pro Phe His Arg Asp Asp Glu Pro Cys Tyr Asp Ala Asp His Gln Val
            610                 615                 620

Leu Thr Ile Asn Leu Thr Gly Glu Ala Glu Phe Lys Ile Ser Cys Lys
625                 630                 635                 640

Ala Gly Ser Gly Ser Cys Thr Leu Val Glu Asn Gln Phe His Leu Ser
                645                 650                 655

Pro Pro Gly Phe Gln Lys Thr His Lys His Ser Val Val Ser Leu Ser
            660                 665                 670

Ala Gly Arg Val Ser Leu Thr Phe Arg Ser Thr Val Lys Gln Ser Val
            675                 680                 685

Thr Ser Glu Glu Gly Asp Cys Val Glu Pro Asp Asn Leu Pro Trp Lys
            690                 695                 700

Ala Trp Leu Gly Lys Leu Arg Asn Leu Gly Phe Arg Gly Met Gln Leu
705                 710                 715                 720

Gln Tyr Asp Pro Asn Gly Ala Leu Ile Ser Pro Ile Glu Ser Val Lys
                725                 730                 735

Ser Leu Pro Lys Cys Ser Pro Glu Lys Val Asp Pro Ser Leu Leu Lys
            740                 745                 750

Met Leu Asp Asn Gln Ala Arg Ala Pro Thr Pro Phe Ser Pro Ser Pro
            755                 760                 765

Ile Arg Ala Lys Ala Tyr Ser Ser Asp Val Lys Asn Ser Arg Ile Gly
            770                 775                 780

Ala Leu Leu Arg Gln Gln Gly Lys Asp Trp Gly His Arg Phe Asp Ser
785                 790                 795                 800

Leu Val Glu Asn Gly Gln Arg Gln Leu Ala Ile Ser Val Ile His Gly
                805                 810                 815

Ala Gly Gly Ser Gly Lys Ser Arg Ala Leu Gln Met Tyr Leu Lys Asp
            820                 825                 830

Asn Pro Asp Ala Asp Val Thr Ile Val Leu Pro Thr Asn Glu Leu Arg
            835                 840                 845

Leu Asp Trp Leu Lys Lys Leu Pro Thr Phe Pro Ala Asp Gln Ile Lys
            850                 855                 860

Thr Phe Glu Lys Ala Leu Leu Ala Pro Thr Lys Pro Thr Val Ile Phe
865                 870                 875                 880

Asp Asp Tyr Gly Lys Leu Pro Ala Gly Tyr Ile Glu Ser Phe Ser Phe
                885                 890                 895

Tyr Met Ser Ser Ala Glu Leu Leu Val Leu Thr Gly Asp Ser Lys Gln
            900                 905                 910

Ser Val His His Glu Ser Asn Glu Asn Ala Met Ser Ser Leu Ile Glu
            915                 920                 925

Pro Phe Thr Leu Glu Ala Asp Lys Tyr Ser Arg Tyr Tyr Ile Asn Ala
            930                 935                 940
```

```
Thr His Arg Asn Lys Arg Asp Leu Ala Asn Lys Leu Gly Val Tyr Ser
945                 950                 955                 960

Glu Val Thr Gly Ile Thr Ser Ile Thr Gln Gly Asn His Pro Val Pro
            965                 970                 975

Gly Leu His Leu Leu Val Pro Ser Leu Tyr Lys Lys Glu Ala Phe Ser
            980                 985                 990

Glu Met Gly His Lys Val Ser Thr Tyr Ala Gly Cys Gln Gly Leu Thr
            995                 1000                1005

Ala Pro Arg Val Gln Ile Leu Leu Ser Glu Glu Thr Ser Met Cys
    1010            1015                1020

Ser Arg Glu Val Ile Tyr Thr Ala Leu Ser Arg Ala Val His Ser
    1025            1030                1035

Ile His Phe Val Asn Cys Gly Pro Asn Asn Gln Ala Phe Trp Ala
    1040            1045                1050

Lys Leu Glu Ser Thr Pro Tyr Leu Lys Ala Phe Leu Ser Thr Leu
    1055            1060                1065

Arg Glu Asp Ala Ala Pro Val Val Lys Pro Lys Glu Glu Ala Pro
    1070            1075                1080

Ala Pro Val Asp Pro Pro Lys Thr His Ile Pro Val Asp Ser Ala
    1085            1090                1095

Met Pro Ile Tyr Glu Asp Leu Leu Asp Gln Met Pro Glu Lys His
    1100            1105                1110

Glu Arg Glu Ile Phe Ser Glu Arg His Gly His Ser Asn Cys Val
    1115            1120                1125

Gln Thr Glu Asp Thr Phe Val Gln Met Phe Ser His Gln Gln Ala
    1130            1135                1140

Lys Asp Glu Thr Leu Leu Trp Ala Thr Ile Glu Ala Arg Leu Val
    1145            1150                1155

Ile Ser Asn Pro Lys Ala Asn Trp Gln Glu Phe Met Glu Lys Arg
    1160            1165                1170

Pro Ile Gly Asp Val Leu Phe Gly Phe Tyr Arg Glu Ala Met Gly
    1175            1180                1185

Leu Pro Thr Glu Pro Ile Ala Phe Glu Pro Gln Leu Trp Glu Ser
    1190            1195                1200

Cys Ile His Glu Val Gln Arg Thr Tyr Leu Ala Lys Pro Ile Asn
    1205            1210                1215

Met Leu Lys Asn Gly Gln Ala Arg Gln Ser Pro Asp Tyr Asp Pro
    1220            1225                1230

Asn Met Ile Ser Leu Phe Leu Lys Ser Gln Trp Val Lys Lys Met
    1235            1240                1245

Glu Lys Leu Gly Ala Leu Lys Ile Lys Pro Gly Gln Thr Ile Ala
    1250            1255                1260

Ser Phe His Gln Ala Thr Val Met Leu Phe Gly Thr Met Ala Arg
    1265            1270                1275

Tyr Met Arg Arg Met Arg Glu Ile Phe Gln Pro Lys Asn Ile Ala
    1280            1285                1290

Ile Asn Cys Glu Met Thr Pro Glu Asp Leu Thr Asp Trp Ala Val
    1295            1300                1305

Gly Ser Ala Gly Gln Trp Lys Phe Ala Gly Pro Ser Leu Ala Asn
    1310            1315                1320

Asp Phe Thr Ala Phe Asp Gln Ser Gln Asp Gly Ala Met Leu Gln
    1325            1330                1335

Phe Glu Val Leu Lys Ala Lys His His Ser Ile Pro Glu Asp Val
    1340            1345                1350
```

```
Leu Asp Ala Tyr Leu His Ile Lys Thr Asn Ser Lys Ile Phe Leu
    1355                1360                1365

Gly Thr Leu Thr Ile Met Arg Leu Thr Gly Glu Gly Pro Thr Phe
    1370                1375                1380

Asp Ala Asn Thr Glu Cys Asn Ile Ala Phe Thr His Ala Lys Phe
    1385                1390                1395

Gln Ile Pro Lys Gly Thr Ala Gln Leu Tyr Ala Gly Asp Asp Ser
    1400                1405                1410

Ala Ile Asp Gly Asn Pro Pro Val Arg Glu Ser Phe Arg Leu Val
    1415                1420                1425

Glu Gln Lys Leu Lys Leu Arg Ser Lys Pro Ala Ile Ala Met Gln
    1430                1435                1440

Glu Lys Gly Asp Trp Ala Glu Phe Cys Gly Tyr Arg Ile Thr Pro
    1445                1450                1455

Lys Gly Phe Ile Lys Asp Pro Lys Lys Leu His Ala Ser Leu Val
    1460                1465                1470

Leu Glu Lys Lys Arg Gly Asn Leu Lys Asn Val Leu Arg Ser Tyr
    1475                1480                1485

Glu Leu Asp Leu Ala Leu Ala Tyr Gln His Arg Asp Glu Leu His
    1490                1495                1500

Glu Leu Leu Ser Glu Glu Leu Arg Leu His Tyr Asp Thr Val
    1505                1510                1515

Arg Thr Leu Val Lys Ser Gly Gly Gly Glu Val Leu Lys Thr Phe
    1520                1525                1530

Leu Pro Lys Asp Glu Ser Leu Tyr
    1535                1540

<210> SEQ ID NO 88
<211> LENGTH: 232
<212> TYPE: PRT
<213> ORGANISM: Alternanthera mosaic virus

<400> SEQUENCE: 88

Met Asn His Phe Thr Asn Leu Leu Ile Glu Glu Gly Tyr Val Arg Thr
1               5                   10                  15

Asn Glu Ile Leu Ser Asp Thr Leu Val Val His Ala Val Ala Gly Ala
            20                  25                  30

Gly Lys Ser Thr Leu Ile Arg Lys Phe Ile His Gln His Pro Gln Ala
        35                  40                  45

Arg Ala Tyr Thr His Gly Val Pro Asp Pro Asn Leu Glu Gly Arg
    50                  55                  60

Phe Ile Gln Ala Phe Lys Asn Pro Asp Pro Asn His Phe Asn Ile Leu
65                  70                  75                  80

Asp Glu Tyr Cys Ala Glu Pro Leu Ser Gly Ser Trp Asn Val Leu Ile
                85                  90                  95

Ala Asp Pro Leu Gln His Arg Ser Gln Ala Leu Arg Pro His Tyr Ile
            100                 105                 110

Lys Arg Glu Ser His Arg Leu Gly Val Ala Thr Cys Glu Leu Leu Thr
        115                 120                 125

Arg Val Gly Leu Pro Val Leu Ser Asn Lys Thr Glu Asp Gln Val Asp
    130                 135                 140

Tyr Gln Gly Ile Phe Glu Gly Pro Leu Phe Gly Thr Val Ile Ala Leu
145                 150                 155                 160

Asp Ser Thr Val Arg Ala Leu Leu Val Lys His Gly Ile Pro Pro Leu
                165                 170                 175
```

```
Cys Pro Ala Glu Val Leu Gly Ser Glu Phe Glu Gln Thr Thr Val Val
            180                 185                 190

Ser Glu Val Pro Leu Ser Gln Val Lys Phe Lys His Ala Leu Tyr Ile
        195                 200                 205

Ala Leu Thr Arg His Lys Lys Ser Leu His Val Arg Ala Pro Pro Leu
    210                 215                 220

Pro Asp Thr Pro Arg Arg Leu Leu
225                 230

<210> SEQ ID NO 89
<211> LENGTH: 1541
<212> TYPE: PRT
<213> ORGANISM: Alternanthera mosaic virus

<400> SEQUENCE: 89

Met Ala His Phe Arg Ser Val Leu Asp Gln Met Asn Asp Pro Ser Leu
1               5                   10                  15

Arg Ala Val Ile Gln Glu Glu Ala Tyr Arg Glu Ile Lys Lys Thr Ile
            20                  25                  30

Ala Glu Thr Lys Gln Tyr Asn Pro Tyr Ala Gln Asp Pro Ala Ala Ala
        35                  40                  45

Asp Ser Leu Glu Lys Leu Gly Ile Glu Ser Asn Pro Phe Ser Val Arg
    50                  55                  60

Ala His Thr His Ala Ala Lys Ser Ile Glu Leu Asp Met Tyr Lys
65                  70                  75                  80

Ile Thr Gly Tyr Ser Leu Pro Lys Glu Asn Pro Ile Thr Phe Leu Phe
                85                  90                  95

Met Lys Arg Ser Lys Leu Gln Tyr Phe His Arg Gly Pro Gln His Gly
            100                 105                 110

Asp Leu Phe Leu Asn Ala Trp Ile Glu Pro Lys Asp Val Thr Arg Tyr
        115                 120                 125

Asn Leu Glu Asp Leu Phe Lys Pro Ser Ile Thr Pro Glu Ile Gln Thr
    130                 135                 140

Arg Val Ala Phe Ile Gly Asp Thr Leu His Phe Leu Pro Leu Gly Ala
145                 150                 155                 160

Ile Arg Glu Ile Phe Thr Ser Ser Gln Lys Leu Gln Thr Leu Tyr Ala
                165                 170                 175

Thr Met Val Leu Pro Pro Glu Ala Met His Arg Met His Ser Ile His
            180                 185                 190

Pro Ser Ile Tyr Glu Leu Glu Phe His Glu Arg Asn Phe Ile Tyr Lys
        195                 200                 205

Pro Gly Gly His Ala Gly Ala Ser Tyr Cys His Glu Tyr Ser Gln Leu
    210                 215                 220

Gln Trp Leu Lys Val Gly Lys Phe Glu Trp Cys Asp Lys Arg Tyr Gln
225                 230                 235                 240

Lys His Tyr Val Thr Ser Gln Ile Leu Glu Thr Lys Gly Ala Asn His
                245                 250                 255

Leu Phe Val Phe Gln Arg Gly Asn Phe Ala Thr Pro Thr Tyr Arg Thr
            260                 265                 270

Phe Gly Val Glu Thr Lys Phe Val Thr Leu Pro Pro Ile Phe Leu Pro
        275                 280                 285

Lys Lys Tyr Asn Ala Arg Tyr Pro Ile Lys Thr Val Ala Gln Gln
    290                 295                 300

Leu Phe Leu Tyr Ile Lys Ser Val Lys Thr Val Thr Glu Arg Asp Ile
305                 310                 315                 320
```

```
Trp Ala Lys Val Arg Gln Ile Ile Lys Thr Ala Glu Leu Gln Ser Tyr
            325                 330                 335

Ser Ala Lys Glu Leu Ala Leu Ile Val Asn Tyr Tyr Leu Leu Ile Ser
            340                 345                 350

Lys Leu Asp Ser Val Thr Cys Phe Asp Asn Val Leu Thr Gly Gly Ala
            355                 360                 365

Leu Lys Lys Leu Phe Lys Pro Ile Val Ala Trp Trp Ser Thr Phe Lys
            370                 375                 380

Gly Ala Leu Phe Gly Lys Glu Phe Glu Gln Leu Met Glu Ala Leu
385                 390                 395                 400

Glu Trp Val Asp Val Ser Leu Ser Tyr Lys Val Glu Thr Tyr Ser Gln
            405                 410                 415

Ala Asn Pro Asn Asn Gln Pro Lys Val Met Phe Gly Tyr Glu Trp Leu
            420                 425                 430

Ser Thr Glu Thr Gly Ala Pro Gly Thr Glu Glu Asp Val Ala Pro Glu
            435                 440                 445

Asn Pro Gln Glu Asp Glu Asp Pro His Glu Lys Tyr Ile Gln Ala Leu
            450                 455                 460

Gln Thr Leu Thr Lys Ala Leu Asp Pro Glu Asn Ala Pro Pro Gln Thr
465                 470                 475                 480

Glu Pro Ala Gln Ser Ser Ile Asn Asp Pro Gln Gln Glu His
            485                 490                 495

Pro Arg Ser Pro His Asp Leu His Thr Asp Glu Ser Pro Ser Cys Ser
            500                 505                 510

Gly Ser Leu Asn Ser Tyr Ala Cys His Cys Pro Cys Gly Ile Glu Leu
            515                 520                 525

Lys Ile Phe Ser Ala Glu Phe Pro Pro Ile Pro Pro Leu Ser His Gly
            530                 535                 540

Asp Arg Leu Lys Asn Arg Glu Ala Phe Phe Phe Ser Arg Asp Gly Thr
545                 550                 555                 560

Pro Tyr Ser Tyr Thr Gly Gly Ser His Val Ser Arg Gly Trp Pro Ala
            565                 570                 575

Phe Leu Asp Gln Ile Leu Ala Thr Ala Glu Leu Val Arg Pro Ile Pro
            580                 585                 590

His Phe Asn Gln Cys Leu Ile Gln Lys Tyr Gln Arg Gly Ala Ser Ile
            595                 600                 605

Pro Phe His Ser Asp Asp Glu Pro Cys Tyr Asp Val Asp His Gln Val
            610                 615                 620

Leu Thr Ile Asn Leu Thr Gly Glu Ala Glu Phe Lys Thr Ser Cys Lys
625                 630                 635                 640

Ala Gly Ser Gly Ser Cys Thr Leu Ala Glu Asn Gln Phe His Leu Ser
            645                 650                 655

Pro Pro Gly Phe Gln Lys Thr His Lys His Ser Val Val Ser Leu Ser
            660                 665                 670

Ala Gly Arg Val Ser Leu Thr Phe Arg Ser Thr Val Lys Gln Gly Val
            675                 680                 685

Thr Ser Glu Glu Gly Asp Tyr Val Glu Pro Asp Asn Leu Pro Trp Lys
            690                 695                 700

Ala Trp Leu Glu Lys Leu Arg Asn Leu Gly Phe Arg Gly Thr Gln Leu
705                 710                 715                 720

Gln Tyr Asp Pro Asn Gly Ala Leu Ile Ser Pro Ile Glu Ser Ile Lys
            725                 730                 735

Ser Leu Pro Lys Cys Ser Pro Glu Lys Val Asn Pro Ser Leu Leu Lys
```

-continued

```
                740                 745                 750
Met Leu Asn Asp Gln Ala Arg Ala Pro Thr Pro Phe Ser Pro Ser Pro
                755                 760                 765
Ile Arg Ala Lys Ala Tyr Ser Ser Asp Val Lys Asn Ser Arg Ile Gly
                770                 775                 780
Ala Leu Leu Arg Gln Gln Gly Lys Asp Trp Gly His Arg Phe Asp Ser
785                 790                 795                 800
Leu Val Glu Asn Gly Gln Arg Gln Leu Ala Ile Ser Val Ile His Gly
                805                 810                 815
Ala Gly Gly Ser Gly Lys Ser Arg Ala Leu Gln Met Tyr Leu Lys Asp
                820                 825                 830
Asn Pro Asp Ala Asp Val Thr Ile Val Leu Pro Thr Asn Glu Leu Arg
                835                 840                 845
Leu Asp Trp Leu Lys Lys Leu Pro Thr Phe Pro Ala Asp Gln Ile Lys
                850                 855                 860
Thr Phe Glu Lys Ala Leu Leu Ala Pro Ile Lys Pro Thr Val Ile Phe
865                 870                 875                 880
Asp Asp Tyr Gly Lys Leu Pro Ala Gly Tyr Ile Glu Ala Phe Ser Cys
                885                 890                 895
Tyr Met Ser Ser Val Glu Leu Leu Val Leu Thr Gly Asp Ser Lys Gln
                900                 905                 910
Ser Val His His Glu Ser Asn Glu Asn Ala Met Ser Ser Leu Ile Glu
                915                 920                 925
Pro Phe Thr Leu Glu Ala Asp Lys Tyr Ser Arg Tyr Tyr Ile Asn Ala
                930                 935                 940
Thr His Arg Asn Lys Arg Asp Leu Ala Asn Lys Leu Gly Val Tyr Ser
945                 950                 955                 960
Glu Val Thr Gly Ile Thr Ser Ile Thr Gln Gly Asn His Pro Val Pro
                965                 970                 975
Gly Leu His Leu Leu Val Pro Ser Leu Tyr Lys Lys Glu Ala Phe Ser
                980                 985                 990
Glu Met Gly His Lys Val Ser Thr Tyr Ala Gly Cys Gln Gly Leu Thr
                995                1000                1005
Ala Pro Arg Val Gln Ile Leu Leu Ser Glu Glu Thr Ser Met Cys
                1010                1015                1020
Ser Arg Glu Val Ile Tyr Thr Ala Leu Ser Arg Ala Val His Ser
                1025                1030                1035
Ile His Phe Val Asn Cys Gly Pro Asn Asn Gln Ala Phe Trp Ala
                1040                1045                1050
Lys Leu Glu Ser Thr Pro Tyr Leu Lys Ala Phe Leu Ser Thr Leu
                1055                1060                1065
Arg Glu Asp Ala Ala Pro Val Val Lys Pro Lys Glu Glu Ala Pro
                1070                1075                1080
Ala Pro Val Asp Pro Lys Thr His Ile Pro Val Asp Ser Ala
                1085                1090                1095
Met Pro Ile Tyr Glu Asp Leu Leu Asp Gln Met Arg Glu Lys His
                1100                1105                1110
Glu Arg Glu Ile Phe Ser Glu Lys His Gly His Ser Asn Cys Val
                1115                1120                1125
Gln Thr Glu Asp Thr Phe Val Gln Met Phe Ser His Gln Gln Ala
                1130                1135                1140
Lys Asp Glu Thr Leu Leu Trp Ala Thr Ile Glu Ala Arg Leu Val
                1145                1150                1155
```

```
Ile Ser Asn Pro Lys Ala Asn Trp Gln Glu Phe Met Glu Lys Arg
1160            1165                1170
Pro Ile Gly Asp Val Leu Phe Gly Phe Tyr Arg Glu Ala Met Gly
1175            1180                1185
Leu Pro Thr Glu Pro Ile Ala Phe Glu Pro Gln Leu Trp Glu Ser
1190            1195                1200
Cys Ile His Glu Val Gln Arg Thr Tyr Leu Ala Lys Pro Ile Asn
1205            1210                1215
Met Leu Lys Asn Gly Gln Ala Arg Gln Ser Pro Asp Tyr Asp Pro
1220            1225                1230
Asn Met Ile Ser Leu Phe Leu Lys Ser Gln Trp Val Lys Lys Met
1235            1240                1245
Glu Lys Leu Gly Ala Leu Arg Ile Lys Pro Gly Gln Thr Ile Ala
1250            1255                1260
Ser Phe His Gln Ala Thr Val Met Leu Phe Gly Thr Met Ala Arg
1265            1270                1275
Tyr Met Arg Arg Met Arg Glu Ile Phe Gln Pro Lys Asn Ile Ala
1280            1285                1290
Ile Asn Cys Glu Met Thr Pro Glu Asp Leu Thr Asp Trp Ala Val
1295            1300                1305
Gly Ser Ala Gly Gln Trp Lys Phe Ala Gly Pro Ser Leu Ala Asn
1310            1315                1320
Asp Phe Thr Ala Phe Asp Gln Ser Gln Asp Gly Ala Met Leu Gln
1325            1330                1335
Phe Glu Val Leu Lys Ala Lys His His Ser Ile Pro Glu Asp Val
1340            1345                1350
Leu Asp Ala Tyr Leu His Ile Lys Thr Asn Ser Lys Ile Phe Leu
1355            1360                1365
Gly Thr Leu Thr Ile Met Arg Leu Thr Gly Glu Gly Pro Thr Phe
1370            1375                1380
Asp Ala Asn Thr Glu Cys Asn Ile Ala Phe Thr His Ala Lys Phe
1385            1390                1395
Gln Ile Pro Lys Gly Thr Ala Gln Leu Tyr Ala Gly Asp Asp Ser
1400            1405                1410
Ala Ile Asp Gly Asn Pro Pro Val Arg Glu Ser Phe Arg Leu Val
1415            1420                1425
Glu Gln Lys Leu Lys Leu Arg Ser Lys Pro Ala Ile Ala Met Gln
1430            1435                1440
Glu Lys Gly Asp Trp Ala Glu Phe Cys Gly Tyr Arg Ile Thr Pro
1445            1450                1455
Lys Gly Phe Ile Lys Asp Pro Lys Lys Leu His Ala Ser Leu Val
1460            1465                1470
Leu Glu Lys Lys Arg Gly Asn Leu Lys Asn Val Leu Arg Ser Tyr
1475            1480                1485
Glu Leu Asp Leu Ala Leu Ala Tyr Gln His Arg Asp Glu Leu His
1490            1495                1500
Glu Leu Leu Ser Glu Glu Glu Leu Arg Leu His Tyr Asp Thr Val
1505            1510                1515
Arg Thr Leu Val Lys Ser Gly Gly Gly Glu Val Leu Lys Thr Phe
1520            1525                1530
Leu Ser Lys Asp Glu Ser Leu Tyr
1535            1540
```

<210> SEQ ID NO 90

```
<211> LENGTH: 232
<212> TYPE: PRT
<213> ORGANISM: Alternanthera mosaic virus

<400> SEQUENCE: 90

Met Asn His Phe Thr Asn Leu Leu Ile Glu Glu Gly Tyr Val Arg Thr
1               5                   10                  15

Asn Glu Ile Leu Ser Asp Thr Leu Val Val His Ala Val Ala Gly Ala
            20                  25                  30

Gly Lys Ser Thr Leu Ile Arg Lys Phe Ile His Gln His Pro Gln Ala
        35                  40                  45

Arg Ala Tyr Thr His Gly Val Pro Asp Pro Pro Asn Leu Glu Gly Arg
    50                  55                  60

Phe Ile Gln Ala Phe Lys Asn Pro Asp Pro Asn His Phe Asn Ile Leu
65                  70                  75                  80

Asp Glu Tyr Cys Ala Glu Pro Pro Ser Gly Ser Trp Asn Val Leu Ile
            85                  90                  95

Ala Asp Pro Leu Gln His Arg Ser Gln Ala Leu Arg Pro His Tyr Ile
            100                 105                 110

Lys Arg Glu Ser His Arg Leu Gly Val Ala Thr Cys Glu Leu Leu Thr
            115                 120                 125

Arg Val Gly Leu Pro Val Leu Ser Asn Lys Thr Glu Asp Gln Val Asp
    130                 135                 140

Tyr Gln Gly Ile Phe Glu Gly Pro Leu Phe Gly Thr Val Ile Ala Leu
145                 150                 155                 160

Asp Ser Thr Val Arg Ala Leu Leu Val Lys His Gly Ile Pro Pro Leu
                165                 170                 175

Cys Pro Ala Glu Val Leu Gly Ser Glu Phe Glu Gln Thr Thr Val Val
            180                 185                 190

Ser Glu Val Pro Leu Ser Gln Val Lys Phe Lys His Ala Leu Tyr Ile
            195                 200                 205

Ala Leu Thr Arg His Lys Lys Ser Leu His Val Arg Ala Pro Pro Leu
    210                 215                 220

Pro Asp Thr Pro Arg Arg Leu Leu
225                 230
```